(12) United States Patent
Heinecke et al.

(10) Patent No.: US 9,604,031 B2
(45) Date of Patent: Mar. 28, 2017

(54) MEDICAL ARTICLE SECUREMENT SYSTEMS AND METHODS OF USING SAME

(71) Applicant: 3M INNOVATIVE PROPERTIES COMPANY, St. Paul, MN (US)

(72) Inventors: Steven B. Heinecke, New Richmond, WI (US); Phong V. Ha, Hudson, WI (US); Donald G. Peterson, Shoreview, MN (US); Daniel P. DeCabooter, Woodbury, MN (US); Matthew H. Fryxell, Minnetonka, MN (US); Jia Hu, Mounds View, MN (US); Peter M. Eisenberg, Minneapolis, MN (US); Thomas G. Skulley, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 309 days.

(21) Appl. No.: 14/014,671

(22) Filed: Aug. 30, 2013

(65) Prior Publication Data

US 2014/0061408 A1 Mar. 6, 2014

Related U.S. Application Data

(60) Provisional application No. 61/695,878, filed on Aug. 31, 2012.

(51) Int. Cl.
*A61M 5/32* (2006.01)
*A61M 25/00* (2006.01)
(Continued)

(52) U.S. Cl.
CPC ........ *A61M 25/002* (2013.01); *A61M 5/1418* (2013.01); *A61M 25/02* (2013.01);
(Continued)

(58) Field of Classification Search
CPC .......... A61M 2025/0266; A61M 25/02; A61M 2025/024; A61M 2025/0253; A61M 2025/028
See application file for complete search history.

(56) References Cited

U.S. PATENT DOCUMENTS

RE24,906 E 12/1960 Ulrich
3,389,827 A 6/1968 Abere
(Continued)

FOREIGN PATENT DOCUMENTS

WO WO 98/53872 12/1998
WO WO 01/62328 8/2001
(Continued)

OTHER PUBLICATIONS

Grip-Lok Catheter Securement, Application of Grip-Lok CS for Arrow CVC Securement; Independent Medical Associates Rev. 1, Oct. 2009; 1 page.
(Continued)

*Primary Examiner* — Emily Schmidt

(57) ABSTRACT

Brackets, systems comprising a bracket, and methods for securing medical articles. The bracket can include a base, a post coupled to the base and extending upwardly from the base in a direction generally normal to a first major surface of the base, and an arm coupled to the base and extending generally parallel to the first major surface of the base. The arm can be spaced a distance from the first major surface of the base to define a channel under the arm that is dimensioned to receive at least a portion of the medical article. The arm can be cantilevered, and the post and the arm can each be fixed with respect to the base. Methods can include abutting an external surface of the medical article against the post; and moving a portion of the medical article into the channel defined by the arm.

19 Claims, 22 Drawing Sheets

(51) Int. Cl.
    *A61M 5/14*     (2006.01)
    *A61M 25/02*     (2006.01)

(52) U.S. Cl.
    CPC . *A61M 2025/024* (2013.01); *A61M 2025/028* (2013.01); *A61M 2025/0246* (2013.01); *A61M 2025/0266* (2013.01); *A61M 2209/088* (2013.01); *Y10T 29/49826* (2015.01)

(56) References Cited

U.S. PATENT DOCUMENTS

| | | |
|---|---|---|
| 4,224,937 A | 9/1980 | Gordon |
| 4,499,896 A | 2/1985 | Heinecke |
| 5,088,483 A | 2/1992 | Heinecke |
| 5,192,273 A | 3/1993 | Bierman |
| 5,354,282 A | 10/1994 | Bierman |
| 6,103,369 A | 8/2000 | Lucast |
| 6,491,664 B2 | 12/2002 | Bierman |
| 6,582,403 B1 | 6/2003 | Bierman |
| 7,014,627 B2 | 3/2006 | Bierman |
| 7,520,870 B2 | 4/2009 | Bierman |
| 7,578,804 B2 | 8/2009 | Bierman |
| 7,922,697 B2 | 4/2011 | Beran |
| 7,981,087 B2 | 7/2011 | Gesler, III |
| 8,016,792 B2 | 9/2011 | Wright |
| 8,162,898 B1 | 4/2012 | Wright |
| 2001/0039399 A1 | 11/2001 | Bierman |
| 2006/0015072 A1* | 1/2006 | Raulerson ............ A61M 25/02 604/180 |
| 2006/0276752 A1* | 12/2006 | Bierman ............... A61M 25/02 604/174 |
| 2007/0265571 A1 | 11/2007 | Utterberg |
| 2008/0027391 A1 | 1/2008 | Bierman |
| 2009/0137962 A1 | 5/2009 | Bracken |
| 2010/0324491 A1 | 12/2010 | Bierman |
| 2011/0202010 A1 | 8/2011 | Bierman |
| 2011/0212325 A1 | 9/2011 | Determan |
| 2011/0282291 A1 | 11/2011 | Ciccone |
| 2011/0319830 A1 | 12/2011 | Peters |
| 2012/0123343 A1 | 5/2012 | Aviles |
| 2012/0143140 A1 | 6/2012 | Bierman |
| 2014/0066856 A1 | 3/2014 | Peterson |
| 2014/0066882 A1 | 3/2014 | Heinecke |

FOREIGN PATENT DOCUMENTS

| | | |
|---|---|---|
| WO | WO 02/11786 | 2/2002 |
| WO | WO 2011/025478 | 3/2011 |

OTHER PUBLICATIONS

International Search Report PCT/US2013/057427; Oct. 18, 2013, 6 pgs.

* cited by examiner

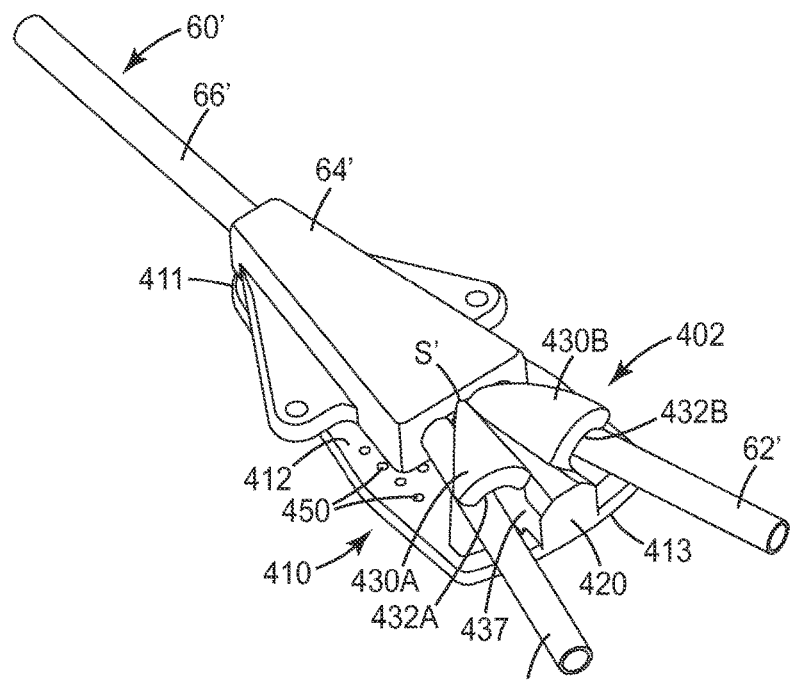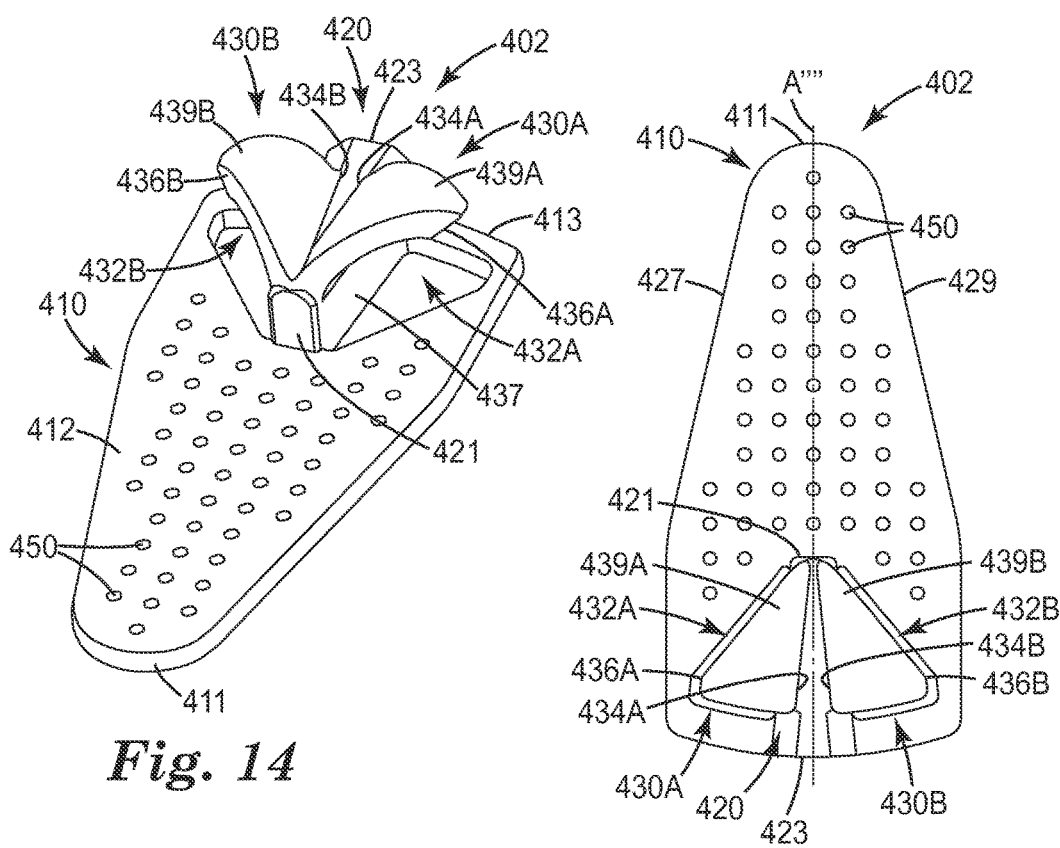

MEDICAL ARTICLE SECUREMENT SYSTEMS AND METHODS OF USING SAME

RELATED APPLICATION

Priority is hereby claimed to U.S. Provisional Patent Application No. 61/695,878, filed Aug. 31, 2012.

FIELD

The present disclosure generally relates to medical article securement systems and methods for securing a medical article to the body of a patient, and particularly, for securing various catheter systems, tubes, or other elongated devices to the body of a patient.

BACKGROUND

In various medical treatments, it can be necessary to introduce fluids and liquid medications directly into a blood vessel of a patient. A simple intravenous (IV) line can be acceptable for short term general use. IV lines are typically placed onto a patient's arm and secured with tape. For longer term and more specialized needs, catheters or other devices are used.

The tip of a catheter can be positioned into a larger vein close to the patient's heart or into the right atrium. If the catheter is inserted through a large neck or chest vein, it is usually referred to as a central venous catheter (CVC). A venous catheter peripherally inserted into the heart through a vein in the arm or other extremity is referred to as a peripherally inserted central catheter (PICC). CVCs and PICCs can be inserted through an incision in the skin into a blood vessel in the patient's body, generally without surgery. CVCs and PICCs can be used to provide medications or fluids to home care patients over longer periods of time, such as weeks or months. CVCs and PICCs may also be used for blood sampling.

Because CVCs and PICCs and similar catheters may remain in place in a patient for several weeks or months, it is important that movement of the catheter be minimized. If the catheter is not secured in place, it may be inadvertently displaced from the intended location or moved back and forth, e.g., during use or dressing changes. Consequently, medication delivered through the catheter may be released at an incorrect position within the blood vessel; the insertion site or the blood vessel can become irritated; the potential for bleeding can be increased; and the insertion site can become contaminated or infected. If extensive movement occurs, the catheter could even inadvertently be removed from the patient, interrupting delivery of medication and requiring re-insertion, often with hospitalization.

In order to keep the catheter or other medical line properly positioned for the duration of treatment, the catheter may be secured to the patient in a variety of ways. One common way of securing a catheter is by taping the catheter or medical line to the patient's skin. However, taping can be time consuming and labor intensive. Tape can also collect bacteria or other contaminants and must be frequently removed and replaced. In addition, taping is not necessarily effective in securing a catheter in place, and removal of the tape may cause undesired motion of the catheter. Sutures have also been used to attach a catheter to a patient. With sutures, the catheter is stitched onto the skin. Sutures, however, can also be a source of infection, can cause pain and inflammation, and can make it more difficult to clean around the incision site. Sutures also require time and skill to place, and can cause scarring.

Various other catheter securement devices have been developed to obviate some of the fallbacks associated with the use of tape and sutures. Some existing catheter securement devices are generally designed for a specific type of catheter. As a result, multiple securement devices may be needed to accommodate different types of catheters, e.g., in hospitals and clinical settings. This can add to the cost and complexity of sourcing, inventory, storage, and selection of the securement devices.

SUMMARY

The present disclosure is generally directed to medical article securement systems and methods, and particularly, to universal medical article securement systems and methods that are adapted to accommodate and reliably secure a large variety of shapes and sizes of catheter systems or other medical articles, particularly elongated medical articles. The medical article securement systems and methods of the present disclosure are generally robust, easy to use, and are designed to facilitate coupling and decoupling a medical article to and from the system, while also providing means for reliably retaining a medical article, e.g., a catheter system, for a desired treatment period.

One aspect of the present disclosure provides a bracket configured for use with a medical article. The bracket can include a base having a longitudinal axis and a first major surface. The bracket can further include a post coupled to the base and extending upwardly from the base in a direction generally normal to the first major surface of the base. The post can be configured to abut an external surface of the medical article to inhibit at least longitudinal movement of the medical article when the medical article is coupled to the bracket. The bracket can further include an arm coupled to the base and extending generally parallel to the first major surface of the base. The arm can be spaced a distance from the first major surface of the base to define a channel under the arm. The channel can be dimensioned to receive at least a portion of the medical article. The arm can include a fixed end and a free end such that the arm is cantilevered. The arm can be configured to inhibit movement of the medical article in at least a direction that is generally normal to the first major surface of the base when the medical article is coupled to the bracket. The post and the arm can each be fixed with respect to the base.

Another aspect of the present disclosure provides a method for coupling a medical article to a medical article securement system. The method can include providing a medical article, and providing a medical article securement system. The medical article securement system can include a bracket. The bracket can include a base having a longitudinal axis and a first major surface. The bracket can further include a post extending upwardly from the base in a direction generally normal to the first major surface of the base. The bracket can further include an arm extending generally parallel to the first major surface of the base. The arm can be spaced a distance from the first major surface of the base to define a channel under the arm. The channel can be dimensioned to receive at least a portion of the medical article. The arm can include a fixed end and a free end, such that the arm is cantilevered. The method can further include abutting an external surface of the medical article against the post; and moving a portion of the medical article into the channel defined by the arm by positioning the portion of the medical article adjacent the free end of the arm, and sliding the portion of the medical article under the arm, into the channel.

Another aspect of the present disclosure can provide a bracket configured for use with a medical article having a proximal end, a distal end, and a longitudinal axis extending from the proximal end to the distal end. The bracket can include a base having a first major surface, a proximal end, a distal end, and a longitudinal axis extending from the proximal end to the distal end, wherein the longitudinal axis of the base is oriented generally parallel to the longitudinal axis of the medical article of the base when the medical article is coupled to the bracket. The bracket can further include an arm coupled to the base and extending generally parallel to the first major surface of the base. The arm can be spaced a distance from the first major surface of the base to define a first channel under the arm. The first channel can generally be oriented generally parallel to the longitudinal axis of the base and dimensioned to receive at least a portion of the medical article. The arm can include a fixed end and a free end, such that the arm is cantilevered. The arm can be configured to inhibit movement of the medical article in at least a direction that is generally normal to the first major surface of the base when the medical article is coupled to the bracket. The bracket can further include a plurality of posts coupled to the base and extending upwardly from the base in a direction generally normal to the first major surface of the base. The plurality of posts together can be configured to abut an external surface on the medical article to inhibit at least longitudinal movement of the medical article when the medical article is coupled to the bracket. Each of the plurality of posts can be separated a lateral distance from an adjacent post to define a second channel therebetween. The second channel can be oriented generally along the longitudinal axis and dimensioned to receive at least a portion of the medical article.

Other features and aspects of the present disclosure will become apparent by consideration of the detailed description and accompanying drawings.

BRIEF DESCRIPTION OF THE DRAWINGS

FIG. 13 is a front perspective view of a bracket according to another embodiment of the present disclosure, shown with a medical article coupled to the bracket.

FIG. 14 is a rear perspective view of the bracket of FIG. 13.

FIG. 15 is a top plan view of the bracket of FIGS. 13 and 14.

DETAILED DESCRIPTION

Figure 1:
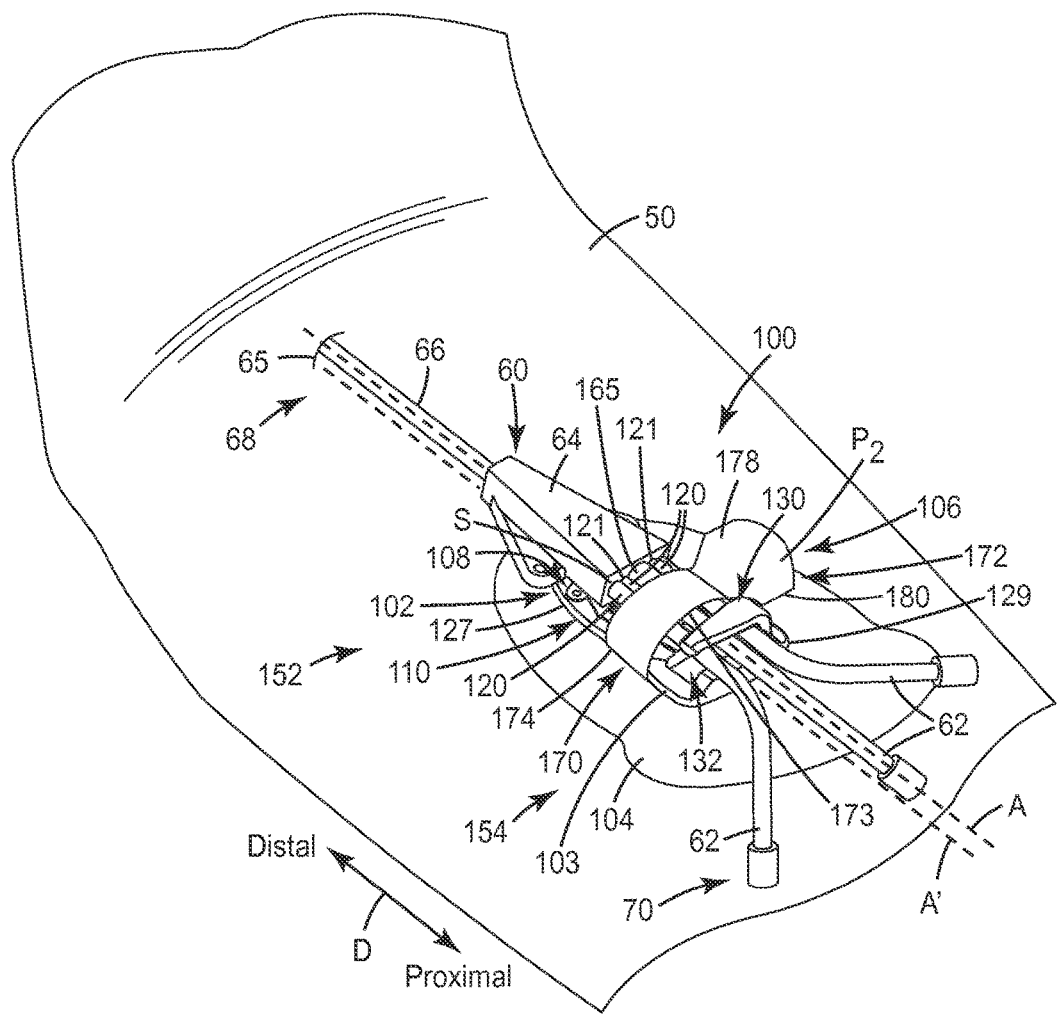
FIG. 1 is a front perspective view of a medical article securement system according to one embodiment of the present disclosure, showing a medical article coupled to the medical article securement system and the medical article securement system coupled to a patient, the medical article securement system comprising a bracket, a flap, indicia, and a base dressing.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising,"

or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to medical article securement systems and methods for safely and reliably securing a medical article, such as a catheter system, upon a desired location of a patient's body. The medical article securement systems can be universal to accommodate and reliably secure a large variety of medical articles or class of medical articles (e.g., PICCs), and can be particularly useful for securing medical articles that need to be secured to a patient over a prolonged period of time, such as weeks or months.

Examples of medical articles that can be employed with the medical article securement system of the present disclosure include, but are not limited to, connector fittings, catheter systems (e.g., including catheters, catheter hubs, catheter adaptors, etc.), fluid supply lines, other similar articles, or combinations thereof. Examples of catheter systems can include, but are not limited to, intravenous (IV) catheters, central venous catheters (CVCs), peripherally inserted central catheters (PICCs), arterial catheters, and dialysis catheters.

The terms "longitudinal" and "axial" are used to refer to a direction or axis that is generally parallel to the direction in which the medical article extends and generally parallel to the overall direction of fluid flow, e.g., along a catheter line.

The term "lateral" is used to refer to a direction or axis that is perpendicular to the longitudinal axis or direction and is used to represent side-to-side motion of a medical article.

The terms "vertical" and "normal" are used to refer to a direction or axis that is normal to both the longitudinal and lateral directions or axes, as well as to the surface of a patient's skin when the medical article securement system is coupled to the patient's skin, and is used to represent the direction of motion toward and away from the skin surface.

The term "proximal" and "distal" are used to represent axial directions, relative to a medical practitioner operating or holding the medical article. That is, the term "distal" is used to refer to the direction away from the medical practitioner (and toward an insertion site on the patient and inside the patient's body), and the term "proximal" is used to refer to the direction toward the medical practitioner (and toward the outside of the patient's body, away from the insertion site). For example, the distal end of a catheter is inserted into the patient, while the proximal end extends exterior of the patient toward the medical practitioner. The distal end of the medical article securement system refers to the end of the system that is configured to be oriented toward the distal end of the medical article to which it will be coupled, and the proximal end of the medical article securement system refers to the end of the system that is configured to be oriented toward the proximal end of the medical article. As a result, in the case of catheter systems, the distal end of the medical article securement system will be oriented toward the insertion site on the patient's body, and the proximal end of the of the medical article securement system will be oriented away from the insertion site on the patient's body.

Figure 2:
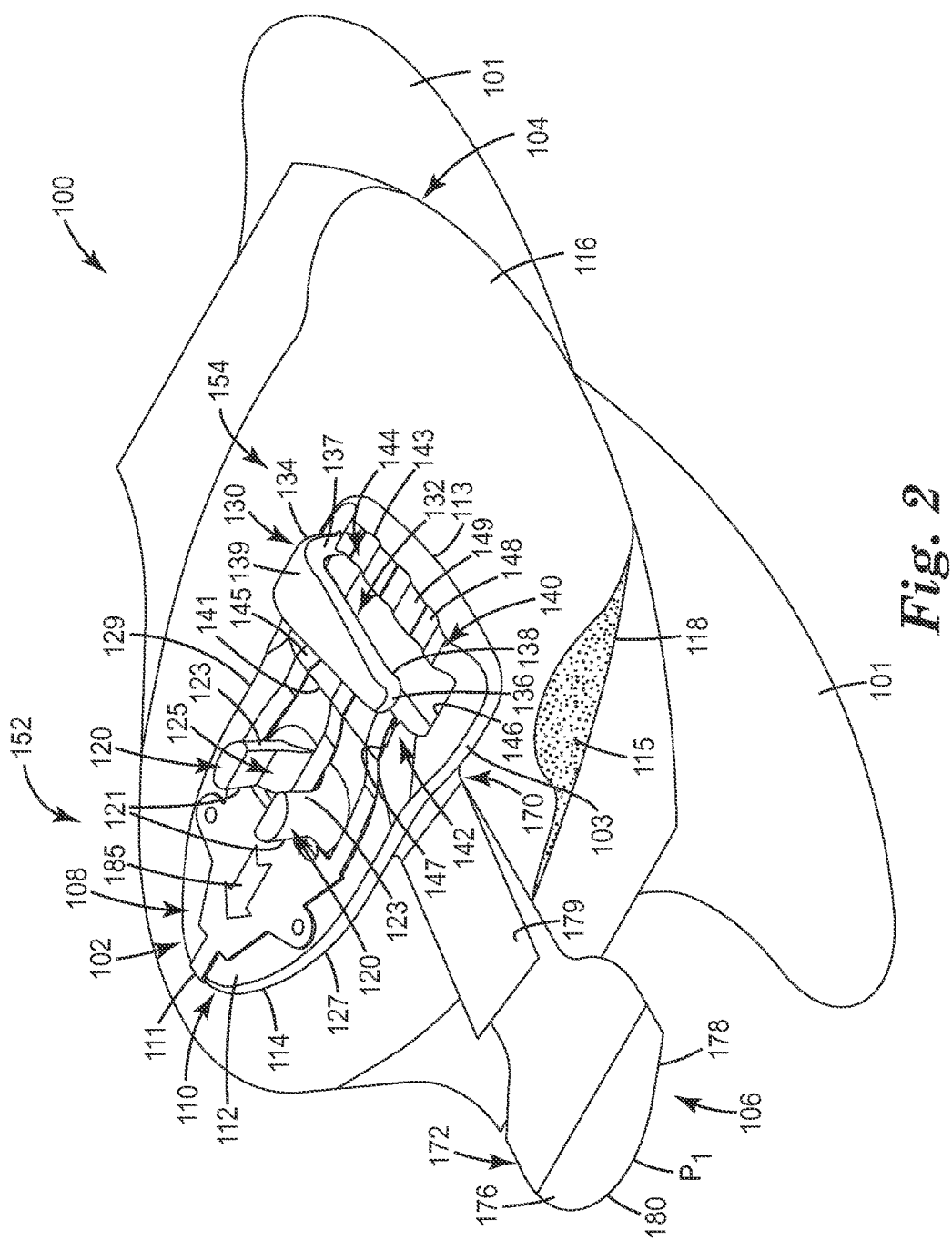
FIG. 2 is a front perspective view of the medical article securement system of FIG. 1, shown without the medical article, prior to coupling to a patient.

FIGS. 1-6 illustrate a medical article securement system 100 according to one embodiment of the present disclosure. FIG. 1 illustrates a system 100 coupled to the skin 50 of a patient, and particularly, to an arm of the patient. FIG. 1 also illustrates an exemplary medical article 60 coupled to the system 100. By way of example only, the medical article 60 is illustrated as being a catheter system having three input catheters (or tubes or lines) 62, a catheter hub 64, and one output catheter (or tube or line) 66. FIG. 2 shows the system 100 prior to coupling the system 100 to the patient.

As shown, the medical article 60 can have a longitudinal axis A that extends along and defines a longitudinal direction D. The medical article can extend distally to include a first longitudinal, distal end or portion 68 (which may extend beyond what is shown in FIG. 1, e.g., into an interior of the patient's body), and can extend proximally to include a second longitudinal, proximal end or portion 70 (which may extend further proximally and include additional elements than what is shown in FIG. 1).

By way of example only, the distal portion 68 of the medical article 60 is shown as entering a peripheral vein in a patient's arm at an insertion site 65, and the proximal portion 70 is shown to include the three input catheters 62 terminating at respective connectors, which can each be connected to fluid supply lines, or the like, for delivery of a variety of nutrients or medicaments to the patient.

As shown in FIGS. 1-4, the system 100 can include a bracket (or "retaining bracket" or "retainer") 102, a base dressing 104, a flap 106, and indicia 108. The bracket 102 and other components of the system 100 can be coupled to the base dressing 104, and the base dressing 104 can be adhered to the skin 50. The flap 106, which is described in greater detail below, can be used in addition to bracket elements to further secure the medical article 60 to the system 100 and the patient's skin 50. The indicia 108, which is described in greater detail below, can be configured to generally mimic the overall shape, appearance and/or configuration of the medical article 60 to provide a visual cue for coupling the medical article 60 to the system 100. The indicia 108 can be coupled to or provided by (e.g., integrally formed with) the bracket 102.

The bracket 102 can include a base (or "platform") 110. The base 110 (or the bracket 102 or the system 100) can include a longitudinal axis A' that is oriented along or parallel to the longitudinal axis A of the medical article 60 when the medical article 60 is coupled to the bracket 102. That is, when the medical article 60 is coupled to the bracket 102, the longitudinal axis A of the medical article 60 can be generally aligned with (which can include directly overlapping or just parallel to) the longitudinal axis A' of the base 110. The longitudinal axis A' of the base 110 (or the bracket 102) also extends along or defines the longitudinal direction D.

The base 110 can include a first major surface 112 (e.g., an upper surface) configured to face away from the patient's skin 50 and to receive at least a portion of the medical article 60. The base 110 can further include a second major surface 114 (e.g., a bottom surface) opposite the first major surface 112 that is configured to face the patient's skin 50 and to be securely coupled (e.g., adhered) to the base dressing 104. The base 110 (or the bracket 102) can further include a distal end (or first longitudinal end) 111 and a proximal end (or second longitudinal end) 113, such that, for example, the distal end 111 is configured to be positioned away from a medical practitioner operating or holding the medical article 60, and the proximal end 113 is configured to be positioned toward the medical practitioner. In the example of a catheter system 60, as shown, the distal end 111 of the base 110 can be positioned toward the insertion site 65, and the proximal end 113 of the base 110 can be positioned away from the insertion site 65. The longitudinal axis A' can extend in the longitudinal direction (e.g., as defined by the medical article 60) between the distal end 111 and the proximal end 113.

The base dressing 104 includes a first side 116 configured to face away from the patient's skin 50, and a second side 118 opposite the first side 116 that comprises a skin-contact adhesive 115 (see FIG. 2) for adhering to the skin 50. The second major surface 114 is configured to be coupled to the first side 116 of the base dressing 104. Although only a single shape of the base dressing 104 is illustrated, it should be understood that the base dressing 104 can take on a variety of shapes and sizes, depending on the shapes and configurations of the other elements of the system 100 and the medical article 60 to be coupled to the system 100. In some embodiments, the base dressing 104 comprises a laminated structure comprising one or more of a fabric, a woven fibrous web, a nonwoven fibrous web, a knit, a polymeric film, or combinations thereof.

The skin-contact adhesive 115 is generally a pressure-sensitive adhesive, and particularly is a pressure-sensitive adhesive that is capable of securely but releasably adhering or bonding to skin (e.g., mammalian skin). The skin-contact adhesive 115 is also generally safe and non-toxic. Skin-contact adhesive layers will generally be selected according to the desired end use of the base dressing 104. In some embodiments, the base dressing 104 can include more than one skin-contact adhesive 115. Where the base dressing 104 comprises more than one skin-contact adhesive layer 115, each skin-contact adhesive layer 115 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 115. In general, the skin-contact adhesive 115 should cause little or no irritation or sensitization of the skin during the intended wear period. Examples of skin-contact adhesives 115 that can be employed with the systems of the present disclosure include, but are not limited to, the adhesives described in U.S. Pat. Nos. RE24,906; 3,389,827; 6,103,369 and 4,499,896, which are incorporated herein by reference. In addition, silicone adhesives such as those described in U.S. Patent Publication No. 2011/0212325, which is incorporated herein by reference, can also be employed.

In some embodiments, e.g., in embodiments employing silicone adhesives, the base dressing 104 and the skin-contact adhesive 115 can be perforated to provide openings from the first side 116 of the base dressing 104 all the way through the second side 118 and the skin-contact adhesive 115, which can enhance permeability of the base dressing 104 and can minimize moisture build-up at the skin surface underlying the base dressing 104.

Figure 3:
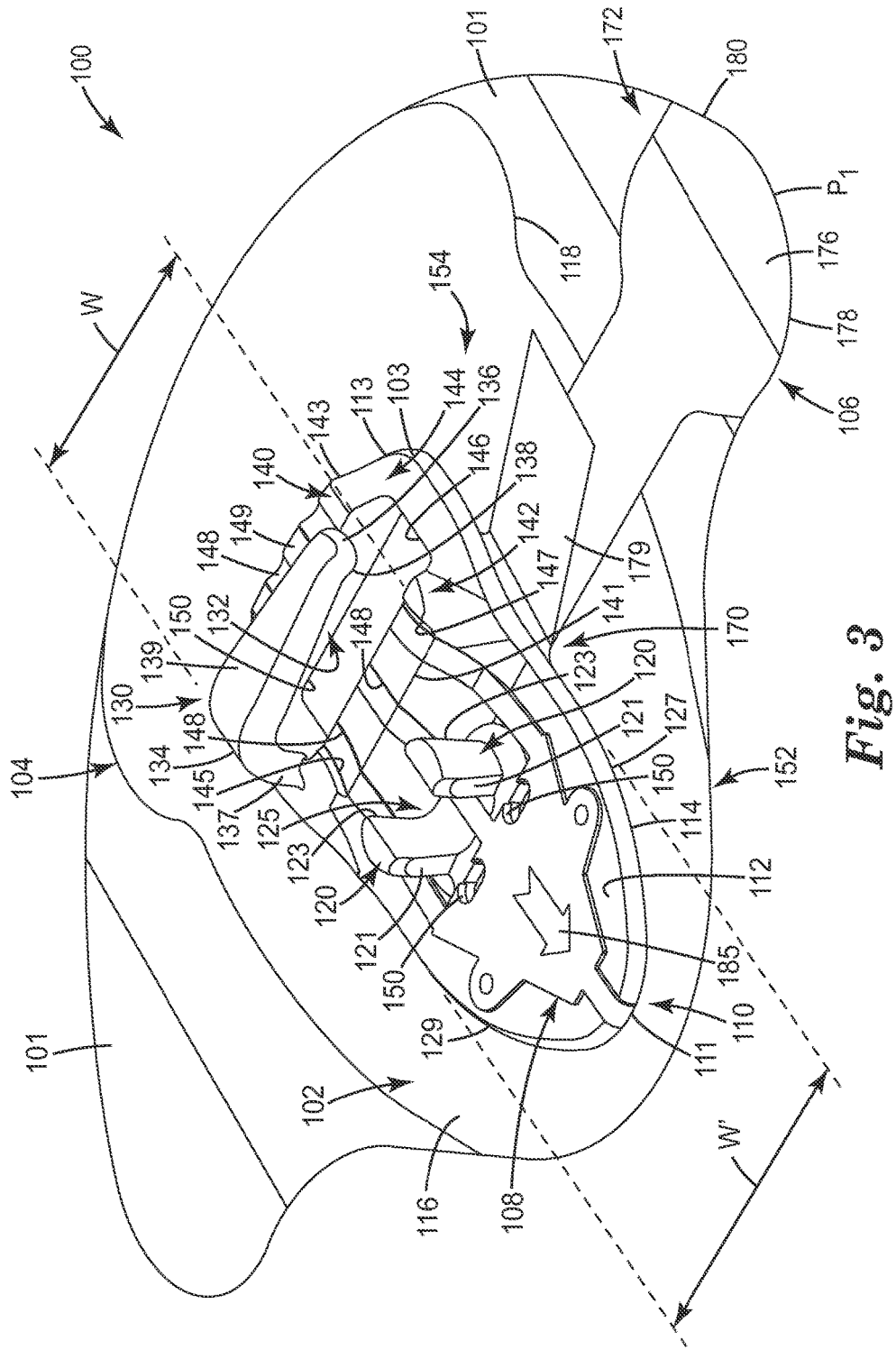
FIG. 3 is a rear perspective view of the medical article securement system of FIGS. 1 and 2.
Figure 4:
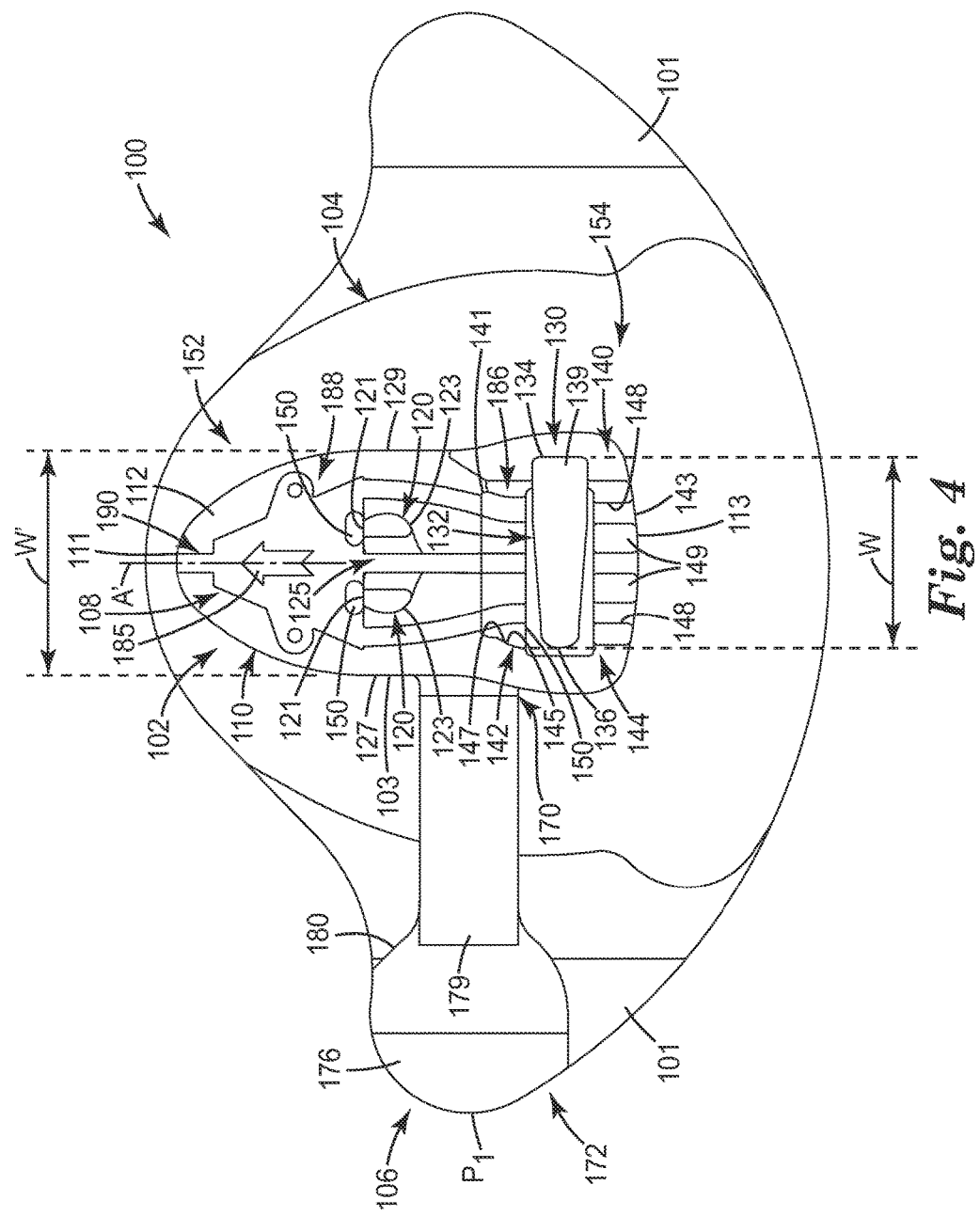
FIG. 4 is a top plan view of the medical article securement system of FIGS. 1-3.

As shown in FIGS. 2-4, in some embodiments, the system 100 can further include one or more release liners 101 that can provide a release layer or surface to the skin-contact adhesive 115 on the second side 118 of the base dressing 104 prior to use. By way of example only, as clearly shown in FIG. 2, the system 100 includes two butterfly-configured release liners 101, such that one portion (e.g., one lateral half) of the base dressing 104 can be applied at a time to the patient's skin 50 to facilitate adhering the system 100 to the skin 50 in a desired orientation without any crinkling or folding of the base dressing 104 before it is ready to be applied. The release liners 101 are illustrated as being symmetrical, however, this need not be the case, depending on the shape and configuration of the base dressing 104.

Examples of liners suitable for use with systems of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner 101 combinations known to those of ordinary skill in the art can be employed in the systems of the present disclosure.

The bracket 102 (e.g., the second major surface 114 of the base 110) can be coupled to the base dressing 104 using a variety of coupling means including, but not limited to, one or more of adhesives, cohesives, magnets, welding (e.g., sonic [e.g., ultrasonic] welding), any thermal bonding or heat sealing technique (e.g., heat and/or pressure applied to one or both of the components to be coupled), other suitable coupling means, or combinations thereof.

The bracket 102 can further include one or more vertical posts (or "projections" or "stop blocks" or "longitudinal stops") 120 coupled to the base 110 that extend upwardly from the base 110, away from the first major surface 112 of the base 110 and the patient's skin 50, in a direction generally normal to the first major surface 112. As shown in FIGS. 1-4, in some embodiments, the bracket 102 can include two or more posts 120, and two posts are shown by way of example only.

Each post 120 can include a distal end 121 positioned toward the distal end 111 of the base 110 and a proximal end 123 positioned toward the proximal end 113 of the base 110. The distal end 121 (as shown in FIG. 1) can be configured to abut a surface S on the medical article 60 to inhibit at least longitudinal movement (e.g., proximally) of the medical article 60 when the medical article 60 is coupled to the bracket 102. Specifically, the post 120 can be configured to abut, and provide a (longitudinal) stop for an external surface S of the medical article 60. By way of example only, the external surface S is illustrated as being a proximal surface or end of the catheter hub 64. In such embodiments, the post 120 can function as a longitudinal proximal stop and can be configured to inhibit proximal movement of the medical article 60 to inhibit the medical article 60 from moving away from the patient (e.g., to inhibit the output catheter 66 from being pulled out of the insertion site 65 of the patient after it has been properly inserted). The external surface S is also illustrated as being a vertical surface of the medical article in that the surface S extends substantially normal with respect to the skin 50 and the first major surface 112 of the base 110 of the bracket 102.

By being configured to abut an external surface S of the medical article 60, each post 120 can facilitate coupling and decoupling of the medical article to the bracket 102 without requiring that any portion of the bracket 102 be forced through any portion of the medical article 60 (e.g., suture holes of a catheter hub or wing) or snapped onto the medical article 60. As a result, no portion of the medical article 60 and/or the bracket 102 needs to be so firmly pressed toward the patient's skin 50 or the bracket 102 during application, or firmly pulled away from the patient's skin 50 during removal, which can cause disruption of the insertion site 65 or undesirable movement of the medical article 60 relative to the patient's skin 50.

The bracket 102 can further include one or more arms (or "fingers" or "bars" or "hooks" or "prongs") 130 coupled to the base 110 that extend generally parallel to the first major surface 112 of the base 110 and are spaced a vertical distance from the first major surface 112 to define a channel 132 under the arm 130. Rather than extending outwardly from the base 110, in some embodiments, as shown, the arm 130 can be positioned in an at least partially overlapping relationship with the base 110, such that at least a portion of the arm 130 extends over the first major surface 112 of the base 110.

The channel 132 can be dimensioned to receive at least a portion of the medical article 60 (e.g., a more proximal portion than the portion positioned adjacent the post(s) 120) between the arm 130 and the base 110. One arm 130 is shown by way of example only, but it should be understood that as many arms 130 as necessary for a given medical article 60 can be employed (see, e.g., the embodiments illustrated in FIGS. 7-18). The arm 130 can include a fixed end 134 and a free end 136, such that the arm 130 is cantilevered. Particularly, the arm 130 can include a pedestal 137 that defines a vertical component of the arm 130 and a horizontal projection 139 that is cantilevered from the pedestal 137 and defines a horizontal component of the arm 130, such that the horizontal projection 139 is spaced a vertical distance from the first major surface 112 of the base 110 by the pedestal 137 to accommodate a portion of the medical article 60 of interest. The projection 139 can be considered to include the fixed end 134 and the free end 136. The projection 139 can extend generally parallel with respect to the first major surface 112 of the base 110, such that the projection 139 and the pedestal 137 are oriented substantially perpendicularly with respect to one another.

Similar to the post(s) 120, the arm 130 can be configured to facilitate coupling and decoupling the medical article 60 without excessive forces or complex motions, by allowing the medical article 60, or a portion thereof, to be simply slid into position in the channel 132 under the arm 130. In some embodiments, the channel 132, e.g., the vertical spacing of the arm 130 from the first major surface 112 of the base 110, can be dimensioned to provide the desired amount of grip or retention on the medical article 60, and/or the appropriate resistance (if any) to positioning the medical article 60 under the arm 130 or removing the medical article 60 from under the arm 130.

When the medical article 60 is coupled to the bracket 102 and a portion thereof is positioned in the channel 132 defined by the arm 130, the arm 130 can be configured to inhibit movement of the medical article 60 in at least a direction that is generally normal to the first major surface 112 of the base 110, i.e., to inhibit the medical article 60 from being pulled away from the patient's skin 50. Depending on the orientation of the arm 130 with respect to the longitudinal axis A' of the base 110, the arm 132 can also inhibit movement of the medical article 60 in other directions (e.g., lateral or oblique) when the medical article 60 is coupled to the bracket 102.

In the embodiment illustrated in FIGS. 1-6, the arm 130 extends generally laterally (and in some embodiments, substantially perpendicularly, as shown in FIG. 4) with respect to the longitudinal axis A' of the base 110 (and with respect to the longitudinal axis A of the medical article 60 when the medical article 60 is coupled to the bracket 102), such that the fixed end 134 is a fixed lateral end 134 and the free end 136 is a free lateral end 136. As a result, the arm 130 of the embodiment of FIGS. 1-6 can also inhibit lateral movement of the medical article 60, particularly in a lateral direction toward the pedestal 137. In such embodiments, the pedestal 137 can function as a lateral stop for the medical article 60.

In some embodiments, as shown in the embodiment of FIGS. 1-6, at least one of the arms 130 of the bracket 102 can include or define a lateral width W that extends from its fixed end 134 to its free end 136, and the post 120 (or plurality of posts 120 if more than one is employed) can be located within the lateral width W on the base 110. In some embodiments, the post(s) 120 can be approximately centered on the base 110 with respect to the lateral width W of the arm 130. In addition, in some embodiments, the arm 130 and the post(s) 120 can be arranged such that the medical article 60 is generally centered with respect to a lateral width (or about the longitudinal axis A') of the base 110 when the medical article 60 is coupled to the bracket 102.

In some embodiments, the free end 136 of the arm 130 (e.g., of the projection 139) can include a retaining feature 138, such as a protrusion, a nub, a rib, or the like, which can at least partially inhibit the medical article 60 from being removed from the channel 132 after it has been positioned in the channel 132. That is, the retaining feature 138 can inhibit movement of the medical article 60 in a direction toward the free end 136 of the arm 130 and generally opposite, or away from, the pedestal 137 or the fixed end 134.

As shown, in some embodiments, the arm 130 can be located on the base 110 proximally with respect to the post 120. Said another way, in some embodiments, the arm 130 can be located toward or adjacent the proximal end 113 of the base 110, and the post(s) 120 can be located toward the distal end 111 of the base 110. More specifically, in some embodiments (as shown in FIGS. 1-5), the arm 130, and particularly, the fixed end 134 of the arm 130, can be located no further distally on the base 110 than the distal end 121 of the post 120.

Such an arrangement can allow for facile coupling of the medical article 60 to the bracket 102, for example, by first abutting the surface S against the distal end(s) 121 of the post(s) 120, and then positioning a more proximal portion of the medical article 60 adjacent the free end 136 of the arm 130, and sliding (e.g., laterally) the portion of the medical article 60 under the arm 130 and into the channel 132. Such action can be accomplished very easily and with a minimal number of steps or forces exerted on the medical article 60, the patient's skin 50, or the insertion site 65. For example, with reference to the catheter system 60 of FIG. 1, in some embodiments, the proximal vertical external surface S of the catheter hub 64 can be abutted or aligned against the distal end 121 of the post 120, minimal hand pressure can be applied to a top surface of the catheter hub 64 with one hand, and the input catheters 62 can be threaded under the arm 130 with the other hand. One-handed operation is also possible.

In addition, in some embodiments, as shown in the embodiment of FIGS. 1-6, the arm 130 and the post(s) 120 can be spaced a longitudinal distance apart on the base 110. In other embodiments, as described below, the arm 130 and the post 120 can be provided by the same structure or adjacent structures, such that the arm 130 and the post 120 are not spaced a longitudinal distance apart. In some embodiments, the longitudinal spacing can allow the bracket 102 to better accommodate the medical article 60 (e.g., depending on the shape and configuration of the medical article 60), or can better accommodate other elements of the medical article securement system 100, such as the flap 106 (if employed).

Whether the arm 130 and the post(s) 120 are spaced longitudinally apart, the arm 130 and the post(s) 120 can be arranged such that at least a portion of the medical article extends, longitudinally with respect to the base 110, adjacent the post 120 (e.g., on a lateral side of at least one post 120) and through the channel 132 defined by the arm 130 when the medical article 60 is coupled to the bracket 102.

Typically, the post(s) 120 are not located tightly adjacent the distal end 111 of the base 110 to allow a distal portion of the first major surface 112 of the base 110 to be exposed to support at least a portion of the medical article 60 (e.g., the catheter hub 64).

In order to minimize the forces necessary to couple the medical article adjacent the post(s) 120, the post(s) can be configured to be free of any radially-extending projections (e.g., adjacent its upper end) that may otherwise need to be snapped into place in or over a portion of the medical article 60.

As shown for the posts 120, the term "post" is generally used to refer to a structure that is open on all sides, such that the posts 120 are not coupled to other elements of the bracket 102 on their sides. Rather, portions of the medical article 60 can be positioned on all sides of each post 120, if necessary. In addition, as shown for the arms 130, the term "arm" is generally used to refer to a structure that extends a distance in a direction substantially parallel to the first major surface 112 of the base 110, and does not generally refer to small round nubs, detents or protuberances.

As further shown in FIGS. 1-6, the post(s) 120 and the arm 130 can be fixed with respect to the base 110 and to each other, such that, in some embodiments, the bracket 102 includes no moving parts, which can enhance manufacturability of the bracket 102 and can also reduce the complexity of the bracket 102, while also minimizing the number of elements that can fail or fracture during use. In the embodiment of FIGS. 1-6, the posts 120 and the arm 130 are integrally formed with the base 110; however, this need not be the case. In some embodiments, the posts 120 and the arm 130 can be coupled to the base 110 in order to be fixed with respect to the base 110. In some embodiments, the posts 120 and the arm 130 are directly coupled to the base 110 such that no intervening elements or structures are positioned or coupled between the posts 120 and the base 110 or between the arm 130 and the base 110, and in some embodiments, the posts 120 and the arm 130 are indirectly coupled to the base 110 by additional structures or elements.

Figure 5:
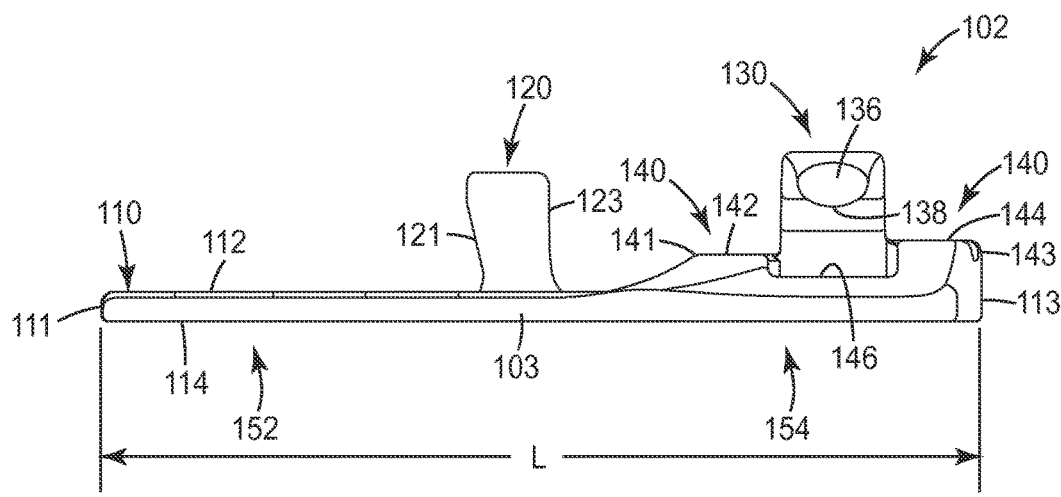
FIG. 5 is a side elevational view of the bracket of the medical article securement system of FIGS. 1-4.

In some embodiments, as shown in FIGS. 2, 3 and 5, the post(s) 120 can be longer in the longitudinal direction at its upper end than at its lower end adjacent the base 110, such that the distal end 121 of the post 120 is tapered toward the base 110. Such a taper in the distal end 121 of the post 120 can at least partially inhibit vertical movement of the medical article 60, which can inhibit the medical article 60 from sliding up the distal end 121 of the post 120 when the medical article 60 is pulled proximally against the distal end 121 of the post 120, e.g., during use, during dressing changes, or during coupling or decoupling of the medical article 60 to the bracket 102. The taper can be linear, arcuate, or the like.

In some embodiments, as shown in FIG. 1, the post 120 can be configured such that at least a portion of the medical article 60 is located laterally and longitudinally adjacent the post 120 when the medical article 60 is coupled to the bracket 102. As such, in some embodiments, the post 120 can further inhibit lateral movement of the medical article 60 when the medical article 60 is coupled to the bracket 102.

As described above, and as illustrated in FIGS. 1-4, in some embodiments, the bracket 102 can include a plurality of posts 120 (e.g., two). In such embodiments, the posts 120 can be located at about the same longitudinal position on the base 110, such that the plurality of posts 120 together are configured to abut a surface (e.g., the surface S) of the medical article 60 to inhibit at least longitudinal movement of the medical article 60 when the medical article 60 is coupled to the bracket 102. The plurality of posts 120 can be spaced a lateral distance apart (or from an adjacent post 120) to define a channel 125 therebetween that is dimensioned to receive at least a portion of the medical article 60. In such embodiments, for simplicity, the channel 132 under the arm 130 can be referred to as a "first channel" or "proximal channel," and the channel 125 between posts 120 can be referred to as a "second channel" or "distal channel."

As shown, the first channel 132 and the second channel 125 can be oriented generally along (i.e., parallel to or overlapping) the longitudinal axes A and A' of the medical article 60 and the base 110, respectively, such that each channel 132, 125 can be referred to as a "longitudinal channel." In some embodiments, the first channel 132 and the second channel 125 can be generally aligned, for example, such that their respective lateral centers are aligned with each other, and optionally, further aligned with the longitudinal axis A' of the base 110.

In some embodiments, the plurality of posts are centered about a lateral width W' of the base 110 at the longitudinal position where the posts 120 are located (see FIGS. 3 and 4), or said another way, centered about the longitudinal axis A' of the base 110, or equally spaced from the longitudinal axis A' of the base 110.

The plurality of posts 120 can function to receive at least a portion of the medical article 60 therebetween, in the second channel 125, which can further inhibit lateral movement of at least the portion received in the second channel 125 when the medical article 60 is coupled to the bracket 102. The plurality of posts 120 and the arm 130 can further be arranged such that at least a portion of the medical article 60 extends longitudinally with respect to the base 110, through the second channel 125 and through the first channel 132 when the medical article 60 is coupled to the bracket 102.

As shown in FIG. 1, in some embodiments, the catheter hub 64 can include a longitudinal proximal extension 165, and in some embodiments, the second channel 125 can be configured to receive at least a portion of the catheter hub 64, such as the extension 165. In some embodiments, the second channel 125 defined between the posts 120 can be dimensioned to receive one catheter (e.g., one input catheter 62), and the first channel 132 under the arm 130 can be dimensioned to receive a plurality of catheters (e.g., the plurality of input catheters 62).

As shown, the second channel 125 can be upwardly-opening, such that the upper ends of the posts 120 are not connected and such that the second channel 125 is open at its top and closed at its bottom, adjacent the base 110, such that at least a portion of the medical article 60 can be slid vertically downwardly between the posts 120 toward the base 110 without necessarily engaging the posts 120 in any type of snap-fit engagement for facile coupling and decoupling of the medical article 60 to and from the bracket 102. That is, the second channel 125 can have a closed lower end, adjacent the first major surface 112 of the base 110, and an open upper end through which at least a portion of the medical article 60 can enter the second channel 125 to be positioned toward or against the base 110 between the plurality of posts 120. In such embodiments, the second channel 125 can have a gutter or canal configuration, which can contribute to the facile coupling and decoupling of the medical article 60 to the bracket 102 described above.

As shown in FIGS. 2-5, in some embodiments, the base 110 can further include a land (or raised portion) 140 having a greater height than other areas of the base 110. The land 140 can define at least a portion of the first major surface 112, and can be located adjacent the arm 130, such that at least a portion of the medical article 60 can be threaded over the land 140 and under the arm 130 when the medical article 60 is coupled to the bracket 102. For example, the land 140 can include one or more portions that are located longitudinally proximally, distally, or both, with respect to the arm 130. By way of example only, the land 140 of the embodiment illustrated in FIGS. 1-6 has a first (e.g., longitudinal, distal) portion 142 located distally adjacent the arm 130 and including a first (e.g., longitudinal, distal) end 141, and a second (e.g., longitudinal, proximal) portion 144 located proximally adjacent the arm 130 and including a second (e.g., longitudinal, proximal) end 143. Said another way, in some embodiments, the arm 130 can be located between the first (distal) end 141 and the second (proximal) end 143 of the land 140. In some embodiments, at least a portion (e.g., the second proximal portion 144) of the land 140 can be located adjacent a longitudinal end (e.g., the proximal end 113) of the base 110 or bracket 102. Further still, in some embodiments (see, e.g., FIGS. 4 and 5), the proximal end 143 of the land 140 can be coincident with the proximal end 113 of the base 110 or bracket 102 itself.

As mentioned above, the land 140 can function together with the arm 130 to retain at least a portion of the medical article 60 in the channel 132 under the arm 130, such that the land 140 can further inhibit vertical and/or lateral movement of the medical article 60 when the medical article 60 is coupled to the bracket 102. That is, in some embodiments, the arm 130 and the land 140 can together inhibit vertical movement of at least a portion of the medical article 60.

As shown in FIGS. 2-5, in some embodiments, the land 140 can include a recess 146 defined between the first portion 142 and the second portion 144, which can facilitate threading the medical article 60 over the first portion 142 of the land 140, under the arm 130 into the channel 132, and over the second portion 144 of the land 140.

In some embodiments, the land 140 can include other features that can help retain at least a portion of the medical article 60. For example, as shown in FIGS. 2-4, in some embodiments, the upper surface of at least a portion of the land 140 can include or define one or more recesses (or grooves or depressions) or protrusions (or ridges). For example, the first portion 142 of the land 140 is illustrated as including a recessed area 145 where the first major surface 112 is depressed. In some embodiments, the recessed area 145 can be recessed relative to ridges (or protrusions) 147, which can facilitate receiving and/or retaining the medical article 60. The ridge 147 adjacent the free end 136 of the arm 130 can function (e.g., along with the retaining feature 138 at the free end 136 of the arm 130) to retain the medical article 60 in the channel 132 by inhibiting movement (e.g., lateral movement) of the medical article 60 in the direction of the free end 136 of the arm 130.

In addition, as shown, in some embodiments, the first major surface 112 defined by one or both of the first portion 142 and the second portion 144 of the land 140 can include one or more grooves 148, which can be separated by one or more leveled areas or ridges (or protrusions) 149. Particularly, in the embodiment of FIGS. 1-6, the grooves 148 are illustrated as being laterally-spaced longitudinal grooves 148 separated by longitudinal leveled areas or ridges (or protrusions) 149.

The grooves 148 and/or ridges 149 can be configured to receive and/or retain (e.g., in a snap-type engagement) at least a portion of the medical article 60, such as a catheter, tube, or the like. Such engagement (e.g., snap-type) can allow the portion of the medical article 60 to be coupled to the bracket 102 with audible and/or tactile feedback without requiring moving parts that are subject to wear and failure. Such snap-type engagements would be distinct from radially-extending projections on the posts 120 that need to be forced into internal openings in the medical article 60 which, as described above, would require unnecessary and excessive forces (e.g., applied in a vertical direction relative the first major surface 112 of the base 110) to couple and decouple the medical article 60 to and from the bracket 102. In some embodiments, the grooves 148 and/or the ridges 149 are located proximally with respect to the posts 120 and are positioned more proximally on the base 110. As a result, incorporating a snap-type engagement with the grooves 148 and/or ridges 149 is less likely to disrupt the insertion site 65. In addition, snap-type engagement in the grooves 148 and/or ridges 149 generally does not require excessive pulling forces or pushing forces in a direction that would disrupt the insertion site 65 or cause excessive pulling or pressure on the patient's skin 50.

In some embodiments, one of the ridges 149 located adjacent the free end 136 of the arm 130 can function (e.g., along with the retaining feature 138 at the free end 136 of the arm 130, and/or along with the ridge 147) to retain the medical article 60 in the channel 132 by inhibiting movement (e.g., lateral movement) of the medical article 60 in the direction of the free end 136 of the arm 130.

Figure 6:
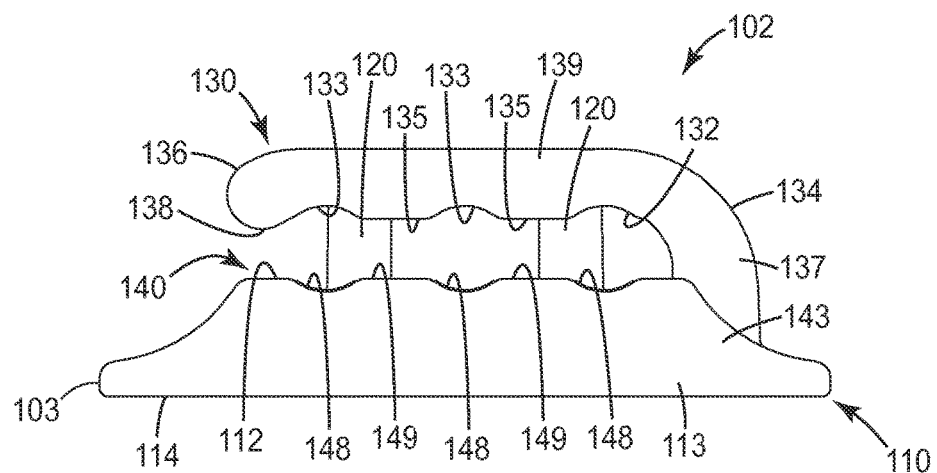
FIG. 6 is a front elevational view of the bracket of the medical article securement system of FIGS. 1-5.

As shown by way of example only in FIG. 6, in some embodiments, the underside of the arm 130 can also include one or more grooves (e.g., longitudinal grooves) 133 and/or ridges 135 to enhance the retention of the portion of the medical article 60 that is received under the arm 130 in the channel 132. Such grooves 133 and/or ridges 135 can also engage the medical article 60 in a snap-type engagement, giving audible and/or tactile feedback. In some embodiments, the grooves 133 and/or ridges 135 formed in the underside of the arm 130 can cooperate with the grooves 148 and/or ridges 149 formed in the first major surface 112 (e.g., in the land 140) to retain the medical article 60. The openings formed collectively by the grooves 133 in the underside of the arm 130 and the grooves 148 in the land 140 (or the first major surface 112) can be dimensioned to accommodate a portion of the medical article 60 without overly restricting such portion. For example, if the grooves 133 and the grooves 148 are sized to retain catheters (such as the input catheters 62), the collective openings can be sized so as not to pinch the catheters or restrict flow through the catheters.

In some embodiments, the land 140 can have a uniform height along its length, even if the land 140 includes separate portions. However, in some embodiments, the first portion 142 and the second portion 144 of the land 140 can have different heights. For example, in some embodiments, the height of the second (e.g., proximal) portion 144 can be greater than the first (e.g., distal) portion 142.

In some embodiments, at least a portion of the first major surface 112, for example, the portion defining the first major surface 112 of the grooves 148 (or another portion of the land 140), can be formed of a different material than a remainder of the base 110. Such a material can include a friction control material of a higher coefficient of friction to enhance the friction (e.g., resistance) between the medical article 60 and at least a portion of the first major surface 112 to further inhibit movement (e.g., longitudinal movement) of the medical article 60 when the medical article 60 is coupled to the bracket 102. More particularly, in some embodiments, at least a portion of the land 140 (e.g., the grooves 148) can be formed of a first material, and the remainder of the first major surface 112 of the base 110 can be formed of a second material, where the first material and the second material are different. In some embodiments, the first material can include a friction control material having a higher coefficient of friction than the second material. For example, the first material can be configured to frictionally engage and/or retain at least a portion of the medical article 60 (e.g., the portion retained in the grooves 148). In such embodiments, the coefficient of friction between the medical article 60 and the first material can be greater than the coefficient of friction between the medical article 60 and the second material. In some embodiments, the friction control material can be provided by the indicia 108, such as when the indicia 108 is co-molded with the remainder of the base 110 onto the first major surface 112 of the base 110 (or to form a portion of the first major surface 112 of the base 110).

The recessed area 145, ridge 147, grooves 148 and ridges 149 are described above as being formed in the land 140; however, it should be understood that such recessed areas 145, ridges 147, grooves 148 and/or ridges 149 can be employed in other areas of the first major surface 112 instead of, or in addition to, those formed in the land 140. That is, even in embodiments that do not employ a land 140 or raised area, the first major surface 112 can still include features (e.g., recesses, grooves, ridges, etc.) that can enhance the retention of at least a portion of the medical article 60.

In some embodiments, the first major surface 112 can be shaped to conform to at least a portion of the medical article 60. For example, the recessed area 145 can be shaped to receive at least a portion of the medical article 60. In other embodiments, the first major surface 112 can include any variety of ridges, recesses or contours necessary to enhance the coupling of the medical article 60. For example, in some embodiments, the first major surface 112 can include a shape that is complementary to the shape (e.g., an external shape) of at least a portion of the medical article 60. This way, the first major surface 112 of the base 110 can be configured to accommodate the medical article 60, such that the medical article 60 is placed against the first major surface 112 of the base 110 (i.e., on top of the base 110) in use, rather than ever passing under the base 110. That is, the base 110 presents a substantially solid and continuous (except for openings or perforations, as described below) surface from which the posts 120 and the arm 130 can project and against which the medical article 60 can be positioned. In some embodiments, the first major surface 112 can further include an adhesive (e.g., located longitudinally between the posts 120 and the arm 130 and/or distally with respect to the posts 120) to better secure the medical article 60 to the first major surface 112 of the base 110.

In some embodiments, the base 110 can include one or more openings or perforations 150 formed therethrough, which can improve the permeability and breathability of the bracket 102 and the overall system 100. In some embodiments, as shown in FIGS. 2-4, the openings 150 can be located adjacent the post 120 and/or the arm 130 (e.g., distally with respect to the posts 120, and in overlapping relationship with (i.e., underneath) the arm 130). Such openings 150 can be manufacturing (e.g., molding) artifacts, but can also serve to enhance permeability. In some embodiments, as described in greater detail below with respect to FIGS. 9-14, bases of the present disclosure can include a series of smaller openings or perforations formed through a larger area on the base to improve permeability and breathability.

As shown in FIGS. 1-5, in some embodiments, the bracket 102 or the base 110 can include a first portion 152 located adjacent or toward, or including, a first longitudinal end (e.g., the distal end 111) where the first major surface 112 of the base 110 is located at a first height from the second major surface 114, and a second portion 154 located adjacent or toward, or including, a second longitudinal end (e.g., the proximal end 113) where the first major surface 112 is located at a second height from the second major surface 114. In some embodiments, the second portion 154 of the bracket 102 (or the base 110) can include or be the land 140. In some embodiments, as shown in the embodiment of FIGS. 1-6, the second height can be greater than the first; however, it should be understood that in some embodiments, the first height is greater. It should also be understood that, in some embodiments, the bracket 102 (or the base 110) is uniform in height, and the first major surface 112 is substantially flat. In addition, it should be understood that, in some embodiments, the bracket 102 can include more than two portions and more than two heights, and that the two portions of two different heights are shown by way of example only, and can depend on the medical article 60 desired to be coupled to the system 100.

In some embodiments, as shown in FIGS. 2, 3 and 5, the first major surface 112 of the base 110 can have a varying height between the first portion 152 and the second portion 154. That is, in some embodiments, the first major surface 112 can be ramped or sloped. Such a ramped or sloped region can be substantially straight or linear, convex, concave, etc., depending on the medical article 60 to be coupled to the bracket 102. In some embodiments, rather than a ramped or sloped surface, the first major surface 112 can include a step (see, e.g., FIGS. 7-12 and 16-18) between the first portion 152 and the second portion 154.

In some embodiments, the post(s) 120 can be located in the first portion 152 of the bracket 102 (or the base 110), and the arm 130 can be located in the second portion 154 of the bracket 102. As mentioned above, in some embodiments, the second portion 154 can include the arm 130 and the land 140.

In some embodiments, the length L of the base 110 (e.g., the distance between the distal end 111 to the proximal end 113, as shown in FIG. 5) can be dimensioned to inhibit the bracket 102 from being delaminated or otherwise removed from the base dressing 104 during use. That is, in some embodiments, the length L of the base 110 can be sized to minimize failure of the system 100, and particularly, to minimize longitudinal delamination of the bracket 102 from the base dressing 104. In general, however, the failure of the system 100 depends on more than one variable. Failure can also depend on how much force the system 100 is targeted to support (e.g., 5 lb versus 15 lb). A more aggressive adhesive coupling the bracket 102 to the base dressing 104 may allow for a shorter base 110 to be employed to support a given load than if a less-aggressive adhesive were employed. For a given adhesive, however, a longer base 110 generally offers greater stability and can support a greater force. In addition, the size (e.g., the length L) of the base 110 generally needs to accommodate clinical application needs, average patient sizes, etc. As a result, in some embodiments, the length L of the base 110 can be at least about 0.75 in (19 mm), in some embodiments, at least about, 1 in (25 mm), and in some embodiments, at least about 1.5 in (38 mm).

Additional exemplary embodiments of brackets of the present disclosure will now be described with respect to FIGS. 7-18. FIGS. 7-18 illustrate various brackets of the present disclosure, wherein like numerals represent like elements. The brackets of FIGS. 7-18 share many of the same elements, features, and functions as the bracket 102 described above with respect to FIGS. 1-6. Reference is made to the description above accompanying FIGS. 1-6 for a more complete description of the features and elements (and alternatives to such features and elements) of the embodiments illustrated in FIGS. 7-18. Any of the features described above with respect to FIGS. 1-6 can be applied to the embodiments of FIGS. 7-18, and vice versa. The same medical article 60 illustrated in FIG. 1 as being coupled to the bracket 102 can also be used with each of the brackets of FIGS. 7-18 and will be described with respect to each of FIGS. 7-12 and 16-18 by way of example only. A slightly different medical article 60' will be described with respect to the embodiment of FIGS. 13-15 by way of example only.

Figure 7:
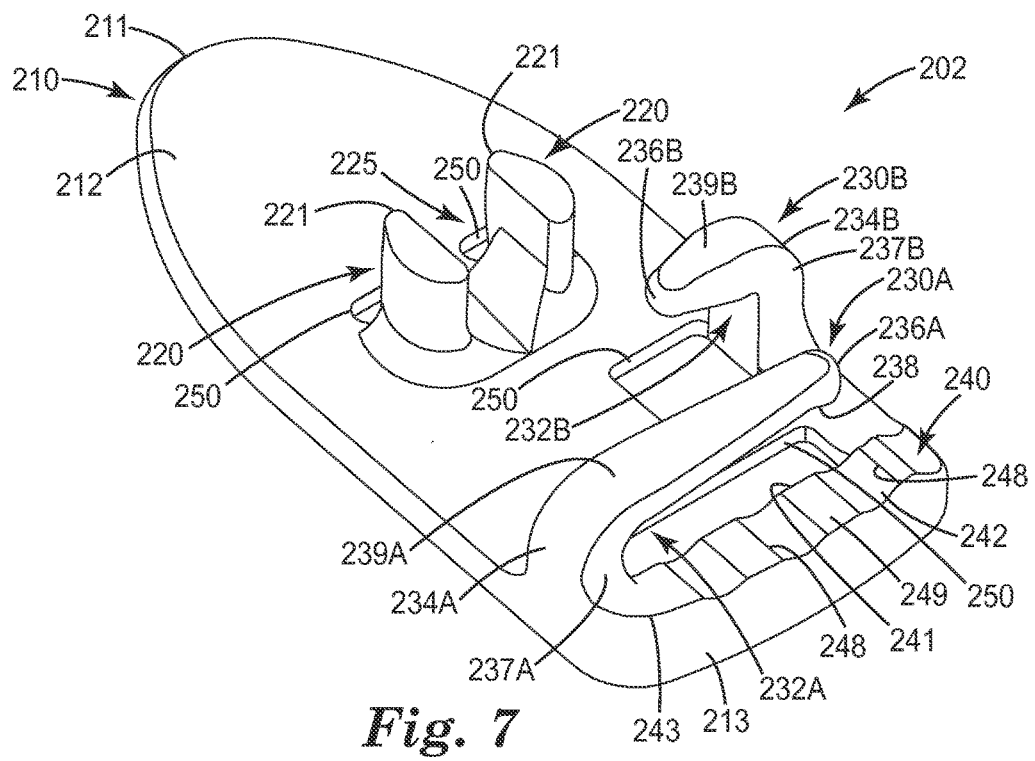
FIG. 7 is a front perspective view of a bracket according to another embodiment of the present disclosure.
Figure 8:
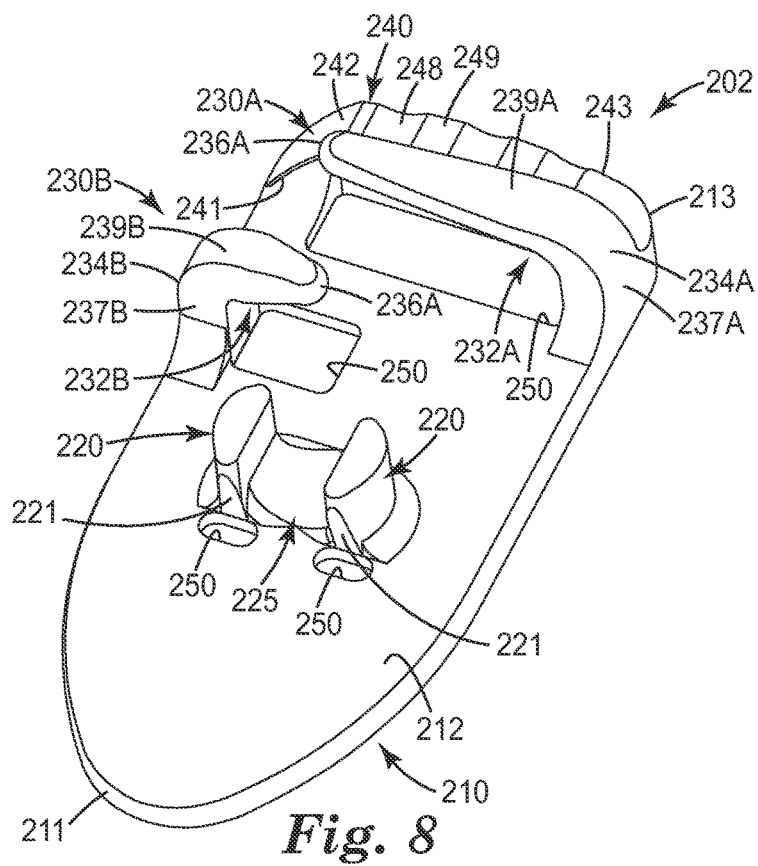
FIG. 8 is a rear perspective view of the bracket of FIG. 7.
Figure 9:
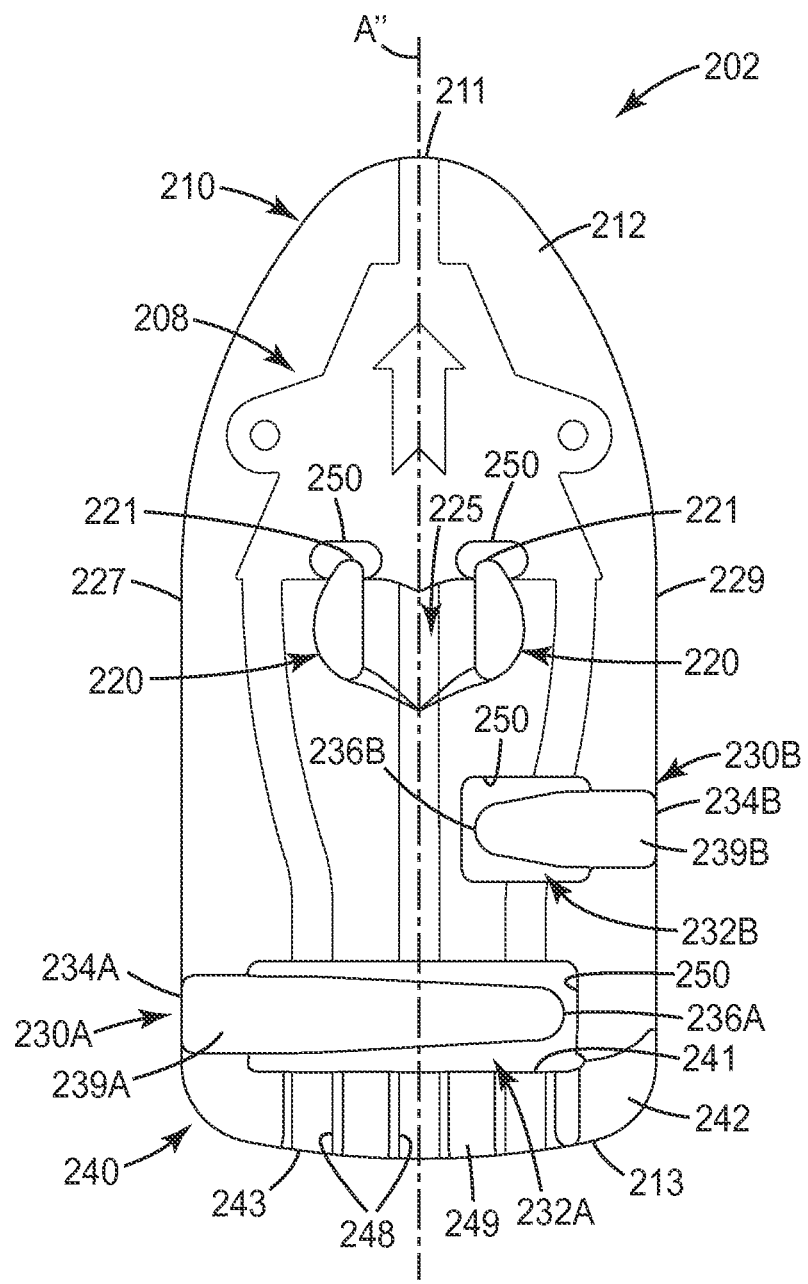
FIG. 9 is a top plan view of the bracket of FIGS. 7 and 8.

FIGS. 7-9 illustrate a bracket 202 according to another embodiment that can be employed with medical article securement systems and methods of the present disclosure, such as, e.g., the medical article securement system 100 of FIGS. 1-6 or other systems described below and illustrated in FIGS. 19-25. The bracket 202 includes a base 210 having a first major surface 212, a distal end 211 and a proximal end 213; two posts 220 that define a channel 225 (e.g., a second channel 225) therebetween; two arms 230 (a first arm 230A that is substantially similar to the arm 130 of FIGS. 1-6, and a second arm 230B); a land 240 located longitudinally adjacent (i.e., proximal) the first arm 230A; a plurality of grooves 248 and/or ridges 249 formed in the first major surface 212 defined by the land 240; and a plurality of openings 250 formed through the base 210. The base 210 (or the bracket 202 or a system comprising the bracket 202) can also include or define a longitudinal axis A" (see FIG. 9) that extends in the longitudinal direction (e.g., as defined by the medical article 60) between the distal end 211 and the proximal end 213.

FIG. 9 illustrates how, in some embodiments, the bracket 202 can include indicia 208 that can provide a visual cue for coupling a medical article (e.g., the medical article 60) to the bracket 202. The indicia 208 can be configured to generally mimic the overall shape, appearance and/or configuration of a medical article of interest (e.g., the medical article 60). The indicia 208 can be coupled to or provided by (e.g., integrally formed with) the bracket 202.

The bracket 202 includes many similarities with the bracket 102 of FIGS. 1-6, except that the bracket 202 of FIGS. 7-9 has a slightly different overall shape (e.g., of the base 210); the bracket 202 includes two arms 230; the land 240 includes only one portion located adjacent one of the arms 230; and the first major surface 212 of the base 210 includes no ramped or sloped surfaces. Each arm 230A and 230B extends a distance in a direction generally parallel to the first major surface 212 of the base 210 and includes a fixed end 234A, 234B and a free end 236A, 236B. As such, the specific details (and alternatives) for each of the structures of the bracket 202 that are not described below can be assumed to be the same as that of the embodiment of FIGS. 1-6, and can have the same varieties or alternatives mentioned above.

Similar to the embodiment of FIGS. 1-6, the posts 220 each include a distal end 221 that is configured to abut an external surface (e.g., the surface S) of the medical article 60.

Each of the arms 230A, 230B is coupled to the base 210 and extends generally parallel to the first major surface 212 of the base 210, and each arm 230A, 230B is spaced a vertical distance from the first major surface 212 to define a channel 232A, 232B (e.g., a first channel 232A, 232B) under the arm 230A, 230B, respectively. Rather than extending outwardly from the base 210, in some embodiments, as shown, each arm 230A, 230B can be positioned in an at least partially overlapping relationship with the base 210, such that at least a portion of the arm 230A, 230B extends over the first major surface 212 of the base 210.

Each channel 232A, 232B can be dimensioned to receive at least a portion of the medical article 60 (e.g., a more proximal portion than the portion positioned adjacent the post(s) 220) between the respective arm 230A, 230B and the base 210. Two arms 230A and 230B are shown by way of example only, but it should be understood that as many arms 230 as necessary for a given medical article 60 can be employed. As shown, each arm 230A, 230B can be cantilevered and can include a pedestal 237A, 237B that defines a vertical component of the arm 230A, 230B and a horizontal projection 239A, 239B that is cantilevered from the respective pedestal 237A, 237B and defines a horizontal component of the arm 230A, 230B, such that the horizontal projection 239A, 239B is spaced a vertical distance from the first major surface 212 of the base 210 by the pedestal 237A, 237B to accommodate a portion of the medical article 60 of interest. The projection 239A, 239B can be considered to include the fixed end 234A, 234B and the free end 236A, 236B. The projection 239A, 239B can extend generally parallel with respect to the first major surface 212 of the base 210, such that the projection 239A, 239B and the pedestal 237A, 237B are oriented substantially perpendicularly with respect to one another.

When the medical article 60 is coupled to the bracket 202 and a portion thereof is positioned in the channels 232A and 232B defined by the arms 230A and 230B, respectively, the arms 230A and 230B can be configured to inhibit movement of the medical article 60 in at least a direction that is generally normal to the first major surface 212 of the base 210, i.e., to inhibit the medical article 60 from being pulled away from a patient's skin. Depending on the orientation of the arms 230A and 230B with respect to the longitudinal axis A" of the base 210, the arm 230A, 230B can also inhibit movement of the medical article 60 in other directions (e.g., lateral or oblique) when the medical article 60 is coupled to the bracket 202.

In the embodiment illustrated in FIGS. 7-9, each arm 230A and 230B extends generally laterally with respect to the longitudinal axis A" of the base 210 (or the bracket 202 or a system comprising the bracket 202) and further with respect to the longitudinal axis A of the medical article 60 when the medical article 60 is coupled to the bracket 202. As such, the fixed end 234A, 234B is a fixed lateral end 234A, 234B, and the free end 236A, 236B is a free lateral end 236A, 236B. As a result, each arm 230A, 230B can also inhibit lateral movement of the medical article 60, particularly in a lateral direction toward the respective pedestal 237A, 237B. In such embodiments, each pedestal 237A, 237B can function as a lateral stop for the medical article 60.

In some embodiments, as shown, one arm (e.g., the first arm 230A) can have has its fixed end (e.g., the fixed end 234A) on a first lateral side 227 (e.g., the left side of FIG.

9) of the base 210, and another arm (e.g., the second arm 230B) can have its fixed end (e.g., the fixed end 234B) on a second lateral side 229 (e.g., the right side of FIG. 9) opposite the first lateral side 227, such that the arms 230 (e.g., the first arm 230A and the second arm 230B) oppose one another. In such embodiments, the arms 230 can together inhibit lateral (e.g., bilateral) movement of the medical article 60 and can together inhibit undesirable removal of the medical article 60 from the channels (e.g., the channels 232A and 232B) defined by the arms 230.

In some embodiments, the arms 230 can be identical, and in some embodiments, as shown, the arms 230 need not be identical or of the same dimensions (e.g., the projections 239A and 239B need not have the same length). As shown, in some embodiments, the first arm 230A can be longer than the second arm 230B, which can facilitate coupling the medical article 60 to the bracket 202, and specifically, can facilitate positioning at least a portion of the medical article 60 under each arm 230A, 230B into the respective channel 232A, 232B. In addition, by way of example only, the free ends 236A and 236B of the arms 230A and 230B are illustrated as passing one another, such that the arms 230 overlap or cross. The configuration and relative sizing of the arms 230 of the bracket 202 are shown by way of example only, and other configurations or relative sizes can be employed. For example, in some embodiments, the second arm 230B can be longer than what is shown, and in some embodiments, the arms 230 do not necessarily overlap. Furthermore, the arms 230A and 230B are illustrated as being substantially parallel with respect to one another, but this need not be the case.

The arms 230 are illustrated as being separated a longitudinal distance from one another (i.e., from an adjacent arm 230), and additionally, from the posts 220. By way of example only, the second arm 230B is illustrated as being approximately centered longitudinally between the posts 220 and the first arm 230A; however, other arrangements are possible.

In some embodiments, one or more of the arms 230 (e.g., the first arm 230A) can include a retaining feature (e.g., protrusion, a nub, a rib, or the like) 238 adjacent its free end (e.g., the free end 236A) which can at least partially inhibit the medical article 60 from being removed from the channel 232A after it has been positioned in the channel 232. That is, the retaining feature 238 can inhibit movement of the medical article 60 in a direction toward the free end (e.g., the free end 236A) of the arm 230 and generally opposite, or away from, the pedestal (e.g., the pedestal 237A) or the fixed end (e.g., the fixed end 234A). The first arm 230A is illustrated as including the retaining feature 238, but it should be understood that neither or both of the arms 230 can include a retaining feature 238 instead.

As shown, in some embodiments, the posts 220 and the arms 230 can be fixed with respect to the base 210 and to each other. In the embodiment of FIGS. 7-9, the posts 220 and the arms 230 are integrally formed with the base 210; however, this need not be the case. In some embodiments, the posts 220 and the arms 230 can be coupled to the base 210 in order to be fixed with respect to the base 210. In some embodiments, the posts 220 and the arms 230 are directly coupled to the base 210 such that no intervening elements or structures are positioned or coupled between the posts 220 and the base 210 or between the arms 230 and the base 210, and in some embodiments, the posts 220 and the arms 230 are indirectly coupled to the base 210 by additional structures or elements.

As mentioned above, by way of example only, the land 240 includes only one portion, namely, a proximal portion 244 comprising a distal end 241 and a proximal end 243, and both the distal end 241 and the proximal end 243 are located proximally with respect to the first arm 230A, such that the first arm 230A is located distally with respect to the land 240. The land 240 can function together with at least the first arm 230A to retain at least a portion of the medical article 60 in the channel 232A under the first arm 230A, such that the land 240 can further inhibit vertical and/or lateral movement of the medical article 60 when the medical article 60 is coupled to the bracket 202. That is, in some embodiments, the first arm 230A and the land 240 can together inhibit vertical movement of at least a portion of the medical article 60.

As mentioned above, the first major surface 212 defined by the land 240 is illustrated as including one or more grooves 248, which can be separated by one or more leveled areas or ridges (or protrusions) 249. Particularly, by way of example only, the grooves 248 are illustrated as being laterally-spaced longitudinal grooves 248 separated by longitudinal leveled areas or ridges (or protrusions) 249. The grooves 248 and/or ridges 249 can be configured to receive and/or retain (e.g., in a snap-type engagement) at least a portion of the medical article 60, such as a catheter, tube, or the like. Such engagement (e.g., snap-type) can allow the portion of the medical article 60 to be coupled to the bracket 202 with audible and/or tactile feedback without requiring moving parts that are subject to wear and failure. In some embodiments, one of the ridges 249 located adjacent the free end 236A of the first arm 230A can function (e.g., along with the retaining feature 238 at the free end 236A of the first arm 230A) to retain the medical article 60 in the channel 232A by inhibiting movement (e.g., lateral movement) of the medical article 60 in the direction of the free end 236A of the first arm 230A.

Figure 10:
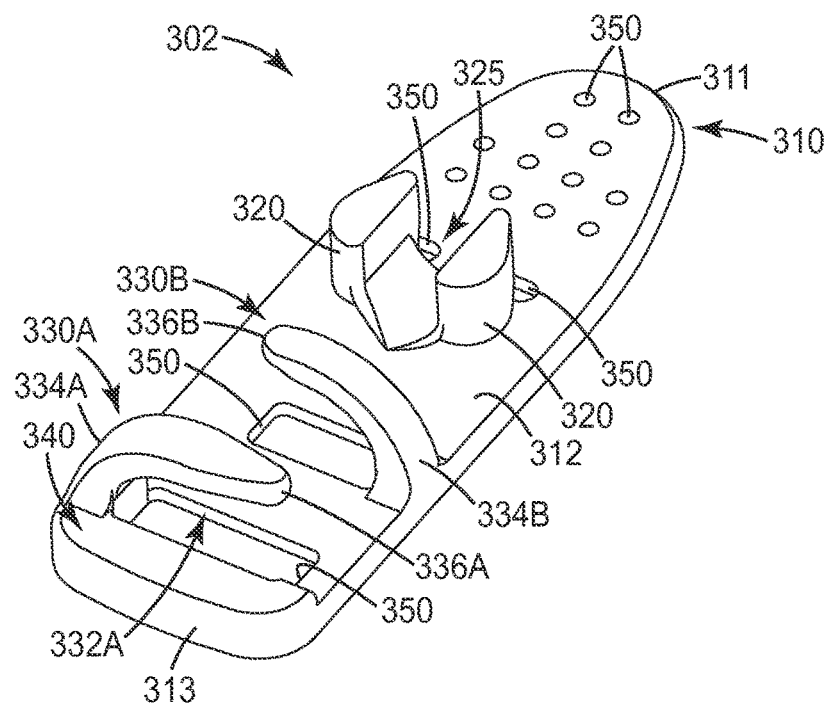
FIG. 10 is a front perspective view of a bracket according to another embodiment of the present disclosure.
Figure 11:
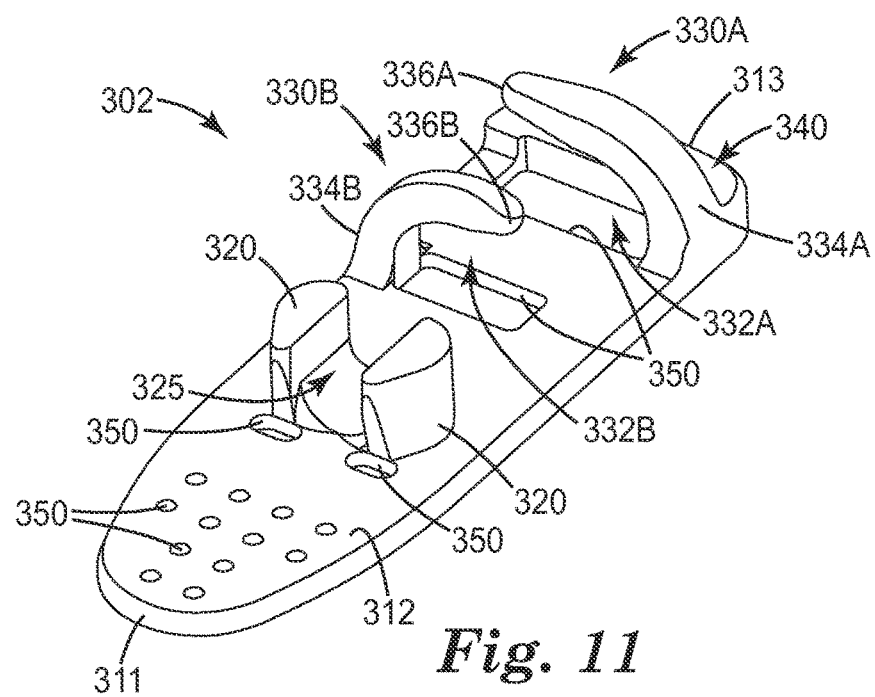
FIG. 11 is a rear perspective view of the bracket of FIG. 10.
Figure 12:
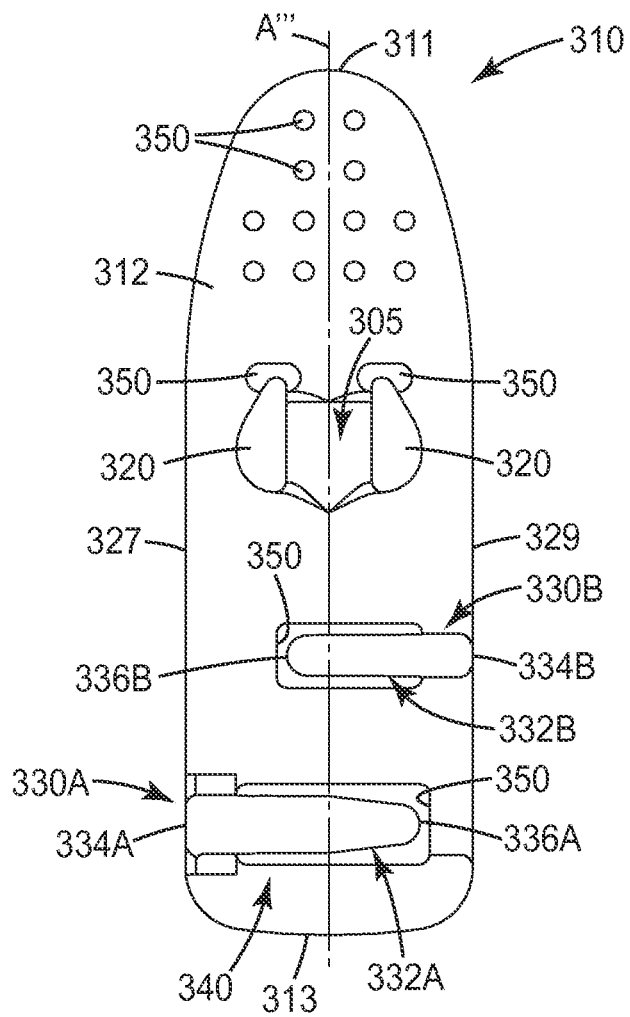
FIG. 12 is a top plan view of the bracket of FIGS. 10 and 11.

FIGS. 10-12 illustrate a bracket 302 according to another embodiment that can be employed with medical article securement systems and methods of the present disclosure, such as, e.g., the medical article securement system 100 of FIGS. 1-6 or other systems described below and illustrated in FIGS. 19-25. The bracket 302 includes a base 310 having a first major surface 312, a distal end 311 and a proximal end 313; two posts 320 that define a channel 325 (e.g., a second channel 325) therebetween; two arms 330 (a first arm 330A that defines a channel 332A (e.g., a first channel 332A), and a second arm 330B that defines a channel 332B (e.g., a first channel 332B)); a land 340 located longitudinally adjacent (i.e., proximal) to the first arm 330A; and a plurality of openings or perforations 350 formed through the base 310. The base 310 (or the bracket 302 or a system comprising the bracket 302) can also include or define a longitudinal axis A''' (see FIG. 12) that extends in the longitudinal direction (e.g., as defined by the medical article 60) between the distal end 311 and the proximal end 313.

The bracket 302 includes many similarities with the bracket 202 of FIGS. 7-9, except that the bracket 302 of FIGS. 10-12 has a slightly different overall shape (e.g., of the base 210); the second arm 330B is longer than the second arm 230B of the bracket 202; neither arm 330A, 330B includes a retaining feature adjacent its free end 336A, 336B; the bracket 302 includes no grooves or ridges formed in the first major surface 312 defined by the land 340; the bracket 302 includes a plurality of openings or perforations 350 formed through the base 310 toward the distal end 311 of the base 310 for enhanced permeability and breathability. The bracket 302 specifically includes a longer and thinner base 310 than that of the bracket 202 (or the bracket 102), which can enhance the stability of the bracket 302 in the longitudinal direction and can further inhibit the bracket 302 from becoming delaminated from other components of a system (e.g., a base dressing) during use. It should be understood that any of the features described above with respect to either the bracket 102 of FIGS. 1-6 or the bracket 202 of FIGS. 7-9 can be employed in the bracket 302 of FIGS. 10-12, and vice versa.

Each arm 330A, 330B includes a fixed end 334A, 334B and a free end 336A, 336B, and similar to the bracket 202 of FIGS. 7-9, the arms 330A and 330B oppose one another, such that one arm (e.g., the first arm 330A) can have has its fixed end (e.g., the fixed end 334A) on a first lateral side 327 (e.g., the left side of FIG. 12) of the base 310, and another arm (e.g., the second arm 330B) can have its fixed end (e.g., the fixed end 334B) on a second lateral side 329 (e.g., the right side of FIG. 12) opposite the first lateral side 327, such that the arms 330 (e.g., the first arm 330A and the second arm 330B) oppose one another. In such embodiments, the arms 330 can together inhibit lateral (e.g., bilateral) movement of the medical article 60 and can together inhibit undesirable removal of the medical article 60 from the channels (e.g., the channels 332A and 332B) defined by the arms 330.

In some embodiments, the arms 330 can be identical, and in some embodiments, as shown, the arms 330 need not be identical or of the same dimensions. As shown, in some embodiments, the first arm 330A can be longer (and/or larger in other dimensions) than the second arm 330B, which can facilitate coupling the medical article 60 to the bracket 302, and specifically, can facilitate positioning at least a portion of the medical article 60 under each arm 330A, 330B into the respective channel 332A, 332B. In addition, by way of example only, the free ends 336A and 336B of the arms 330A and 330B are illustrated as passing one another, such that the arms 330 overlap or cross. The configuration and relative sizing of the arms 330 of the bracket 302 are shown by way of example only, and other configurations or relative sizes can be employed. For example, in some embodiments, the second arm 330 can be shorter or longer than what is shown, and in some embodiments, the arms 330 do not necessarily overlap. Furthermore, the arms 330A and 330B are illustrated as being substantially parallel with respect to one another, but this need not be the case.

The arms 330 are illustrated as being separated a longitudinal distance from one another (i.e., from an adjacent arm 330), and additionally, from the posts 320. By way of example only, the second arm 330B is illustrated as being approximately centered longitudinally between the posts 220 and the first arm 330A; however, other arrangements are possible.

As shown, in some embodiments, the posts 320 and the arms 330 can be fixed with respect to the base 310 and to each other. In the embodiment of FIGS. 10-12, the posts 320 and the arms 330 are integrally formed with the base 310; however, this need not be the case. In some embodiments, the posts 320 and the arms 330 can be coupled to the base 310 in order to be fixed with respect to the base 310. In some embodiments, the posts 320 and the arms 330 are directly coupled to the base 310 such that no intervening elements or structures are positioned or coupled between the posts 320 and the base 310 or between the arms 330 and the base 310, and in some embodiments, the posts 320 and the arms 330 are indirectly coupled to the base 310 by additional structures or elements.

While not illustrated in FIGS. 10-12, the bracket 302 can further include indicia, similar to the indicia 108 and 208 to provide a visual cue for coupling the medical article 60 to the bracket 302.

FIG. 13-15 illustrate a bracket 402 according to another embodiment that can be employed with medical article securement systems and methods of the present disclosure, such as, e.g., the medical article securement system 100 of FIGS. 1-6 or other systems described below and illustrated in FIGS. 19-25. FIG. 13 illustrates a medical article 60' coupled to the bracket 402. By way of example only, the medical article 60' is illustrated as being a catheter system comprising two input catheters 62', a catheter hub 64', and one output catheter 66'.

The bracket 402 includes a base 410 having a first major surface 412, a distal end 411 and a proximal end 413; one post 420 having a distal end 421 and a proximal end 423; two arms 430 (a first arm 430A that defines a channel 432A (e.g., a first channel 432A), and a second arm 430B that defines a channel 432B (e.g., a first channel 432B)); and a plurality of openings or perforations 450 formed through the base 410. The base 410 (or the bracket 402 or a system comprising the bracket 402) can also include or define a longitudinal axis A'''' (see FIG. 15) that extends in the longitudinal direction (e.g., as defined by the medical article 60') between the distal end 411 and the proximal end 413.

The bracket 402 has a different overall shape and configuration (e.g., the shape of the base 410) than the other brackets described above and illustrated in FIGS. 1-12. In addition, the bracket 402 is different from the others described above in that the bracket 402 includes a single post 420 and two arms 430 that extend substantially parallel to the first major surface 412 of the base 410 from the post 420. In some embodiments, an upper surface of the post 420 (and/or arms 430) can be configured to receive at least a portion of a medical article (e.g., the medical article 60'). For example, in some embodiments, the upper surface of the post 420 and/or the arms 430 can include a longitudinal groove and/or ridge that can be configured to receive at least a portion of the medical article (e.g., a catheter, tube, or the like).

While not illustrated in FIGS. 13-15, the bracket 402 can further include indicia, similar to the indicia 108 and 208 to provide a visual cue for coupling the medical article 60' to the bracket 402.

The bracket 402 includes a greater number of openings or perforations 450 formed through the base 410, particularly, between the post 420 and the distal end 411 of the base 410. In addition, the first major surface 412, particularly, in the region between the distal end 411 of the base 410 and the post 420 can be configured to receive at least a portion of the medical article 60', such as, for example, the catheter hub 64'.

Similar to the brackets described above, the bracket 402 includes a substantial length in the longitudinal direction (e.g., along the longitudinal axis A'''') to receive the medical article 60' (or a portion thereof) and to inhibit the bracket 402 from delaminating from other elements of a system (e.g., a base dressing) during use, and to enhance the stability of the bracket 402 on a patient's skin, particularly in the longitudinal direction in which the medical article 60' extends.

By way of example only, the bracket 402 includes no raised areas or lands, or ramped or sloped surfaces, but rather, is substantially flat. However, it should be understood that the bracket 402 can include any of the above-described land structures, grooves, recesses, ramped surfaces, or the like to enhance retention of the medical article 60'.

The post 420, and particularly, the distal end 421 of the post 420 can be configured to abut an external surface (e.g., the surface S') of the medical article 60', similar to the above-described posts. However, unlike the above-described posts, the post 420 is singular and also provides a pedestal 437 to each of the arms 430A and 430B. The post 420 can therefore inhibit at least longitudinal movement of the medical article 60' (e.g., proximally) when the medical article 60' is coupled to the bracket 402.

The arms 430 are illustrated as having a rounded shape, which can enhance the retention of tube-like structures on the medical article 60', such as the input catheters 62', as shown in FIG. 13. However, even with the slightly rounded configuration, the arms 430 can be considered to extend generally parallel to the first major surface 412 of the base 410. For example, a tangent of the upper rounded surface of each arm 430 can extend substantially parallel to the first major surface 412.

Each arm 430A and 430B is coupled (e.g., fixedly) to the base 410 and is spaced a vertical distance from the first major surface 412 to define the respective channel 432A, 432A under the arm 430A, 430B, respectively. Each arm 430A, 430B includes a fixed end 434A, 434B and a free end 436A, 436B. Rather than extending outwardly from the base 410, in some embodiments, as shown, each arm 430A, 430B can be positioned in an at least partially overlapping relationship with the base 410, such that at least a portion of the arm 430A, 430B extends over the first major surface 412 of the base 410.

In addition, in some embodiments, as shown in FIGS. 13-15, the fixed end 434A, 434B of each arm 430A, 430B can be coupled to or provided by the post 420 (which can serve as the pedestal 437 for each arm 430A, 430B), and the free end 436A, 436B of each arm 430A, 430B can extend outwardly from the post 420, such that each arm 430A, 430B is cantilevered with respect to the post 420. In addition, each arm 430A, 430B can include a horizontal projection 439A, 439B that includes the fixed end 434A, 434B and the free end 436A, 436B and extends outwardly from the post 420, such that the horizontal projection 439A, 439B is substantially perpendicular to the post 420 (i.e., the pedestal 437). In some embodiments, as shown, the post 420 and the arms 430 can be provided by the same structure, such that the post 420 and at least one arm 430 are integrally formed.

In addition, as shown, in some embodiments, the arms 430A and 430B, and particularly, the fixed ends 434A, 434B of the arms 430A and 430B can be located proximally with respect to the distal end 421 of the post 420, or no further distally than the distal end 421 of the post 420.

Each channel 432A, 432B can be dimensioned to receive at least a portion of the medical article 60' (e.g., a more proximal portion than the portion positioned adjacent the post(s) 420) between the respective arm 430A, 430B and the base 410. Two arms 430A and 430B are shown by way of example only, but it should be understood that as many arms 430 as necessary for a given medical article 60' can be employed.

When the medical article 60' is coupled to the bracket 402 (as shown in FIG. 13) and a portion thereof is positioned in the channels 432A and 432B defined by the arms 430A and 430B, respectively, the arms 430A and 430B can be configured to inhibit movement of the medical article 60' in at least a direction that is generally normal to the first major surface 412 of the base 410, i.e., to inhibit the medical article 60' from being pulled away from a patient's skin. Depending on the orientation of the arms 430A and 430B with respect to the longitudinal axis A"" of the base 410, the arms 430A, 430B can also inhibit movement of the medical article 60' in other directions (e.g., lateral or oblique) when the medical article 60' is coupled to the bracket 402.

In the embodiment illustrated in FIGS. 13-15, each arm 430A and 430B extends generally laterally with respect to the longitudinal axis A"" of the base 410 (or the bracket 402 or a system comprising the bracket 402) and further with respect to the longitudinal axis A of the medical article 60' when the medical article 60' is coupled to the bracket 402. As such, the fixed ends 434A, 434B are fixed lateral ends 434A, 434B, and the free ends 436A, 436B are free lateral ends 436A, 436B. As a result, each arm 430A, 430B can also inhibit lateral movement of the medical article 60', particularly in a lateral direction toward the post 420 (i.e., pedestal 437). In such embodiments, the post 420 can also function as a lateral stop for the medical article 60'.

Unlike the brackets 202 and 302 described above, the arms 430A, 430B of the bracket 402 do not overlap or cross one another. Rather, the arms 430A, 430B extend from the post 420 in opposite directions. By way of example only, the post 420 is illustrated as being located generally centrally with respect to the base 410, and the free end 436A of the first arm 430A extends from the post 420 generally toward a first lateral side 427 (e.g., the left side of FIG. 15) of the base 410, and the free end 436B of the second arm 430B extends from the post 420 in an opposite direction toward a second lateral side 429 of the base 410 (e.g., the right side of FIG. 15). Together, the arms 430 can inhibit lateral (e.g., bilateral) movement of the medical article 60' (e.g., of two portions of the medical article 60', such as the input catheters 62').

As further shown, in some embodiments, the arms 430A, 430B can be located directly adjacent the post 420, and particularly, directly adjacent the distal end 421 of the post 420, such that the post 420 and the arms 430 are not separated a longitudinal distance apart. Because of this arrangement, in some embodiments, abutting the external surface S' of the medical article 60' adjacent the distal end 421 of the post 420 can occur substantially simultaneously with positioning a portion of the medical article 60' (e.g., the input catheters 62') in the first channels 432A, 432B defined by the arms 430A, 430B. Such action can be accomplished very easily and with a minimal number of steps or forces exerted on the medical article 60', the patient's skin (e.g., the skin 50 illustrated in FIG. 1), or the insertion site (e.g., the insertion site 65 illustrated in FIG. 1). For example, with generally one simple motion, the proximal vertical external surface S' of the catheter hub 64' can be abutted or aligned against the distal end 421 of the post 420, and the input catheters 62' can be threaded under the arms 430, e.g., even all with one hand in some cases.

The phrase "substantially simultaneously" is intended to include where one action occurs almost immediately before or after another action, as well as when two actions occur exactly simultaneously, or when one action also accomplishes one or more additional actions.

As shown, in some embodiments, the arms 430 can be identical and symmetrical (e.g., about the longitudinal axis A""), and the arms 430 extend outwardly from the post 420 at the same longitudinal position. However, this need not necessarily be the case. For example, in some embodiments, the arms 430 may not be identical in shape or size, and/or the post 420 may not be centered with respect to the base 410, and/or the arms 430 may extend from the post 420 at different longitudinal positions along longitudinal length of the post 420. In addition, in some embodiments, a plurality of first arms 430A and/or a plurality of second arms 430B can be employed, and the post 420 can extend longer in the longitudinal direction than the post 420 illustrated in FIGS. 13-15.

Furthermore, in some embodiments, the post 420 can actually be separated into two posts 420 separated a lateral distance apart, for example, to define a channel (like the second channel 125) therebetween that can be dimensioned to receive at least a portion of a medical article (e.g., a middle catheter of a three-input catheter system, similar to the medical article 60 shown in FIG. 1). In such embodiments, each post 420 can provide a pedestal 437 for an arm 430, and the distal ends 421 of the posts 420 can together abut an external surface (e.g., the surface S') of a medical article, similar to the posts 120 of FIGS. 1-6. Other configurations can be contemplated to accommodate different medical articles.

As shown, in some embodiments, the post 420 and the arms 430 can be fixed with respect to the base 410 and to each other. In the embodiment of FIGS. 13-15, the post 420 and the arms 430 are integrally formed with the base 410 and to each other; however, this need not be the case. In some embodiments, the post 420 and the arms 430 can be coupled to the base 410 in order to be fixed with respect to the base 410. In some embodiments, the post 420 and the arms 430 are directly coupled to the base 410 such that no intervening elements or structures are positioned or coupled between the post 420 and the base 410, and in some embodiments, the post 420 and the arms 430 are indirectly coupled to the base 410 by additional structures or elements.

Figure 16:
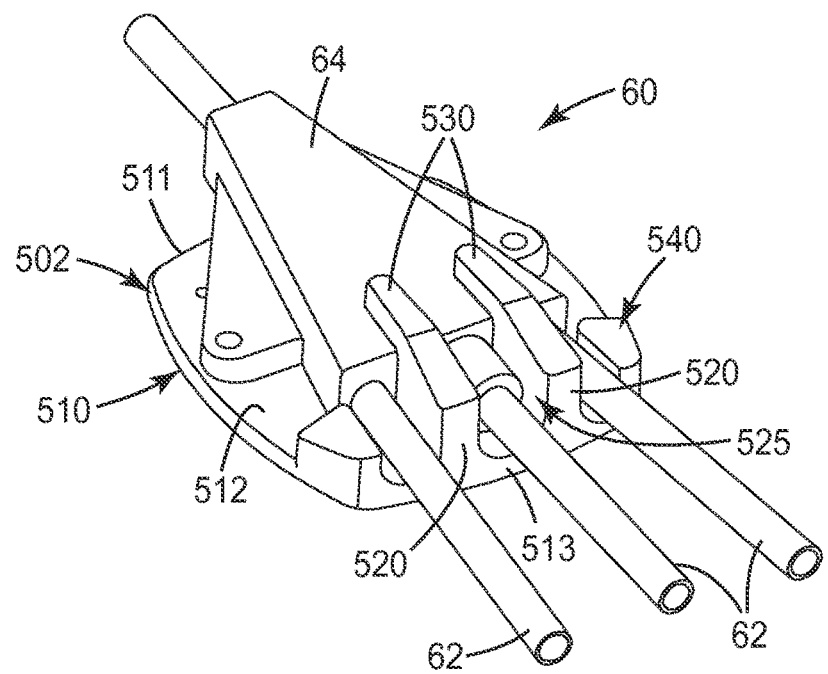
FIG. 16 is a front perspective view of a bracket according to another embodiment of the present disclosure, shown with a medical article coupled to the bracket.
Figure 17:
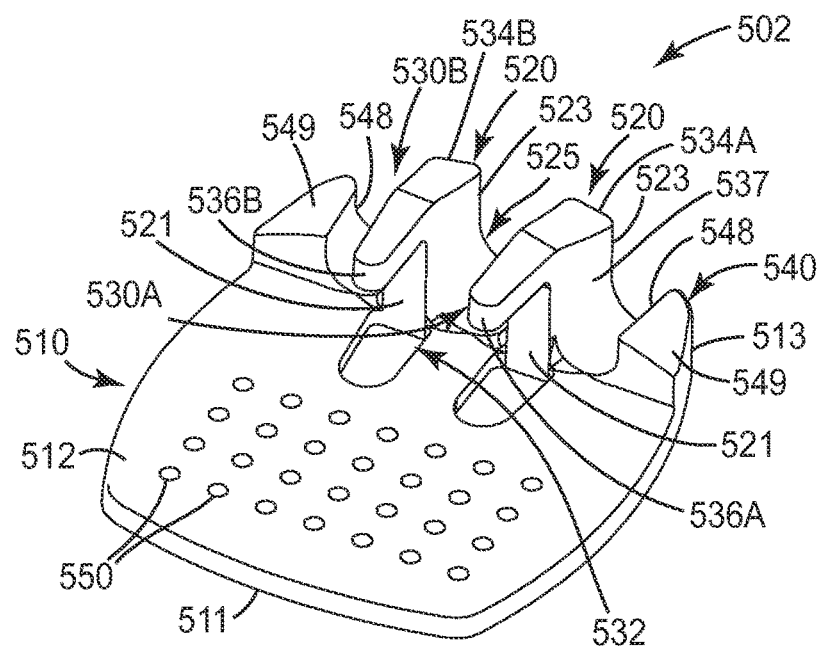
FIG. 17 is a rear perspective view of the bracket of FIG. 16.
Figure 18:
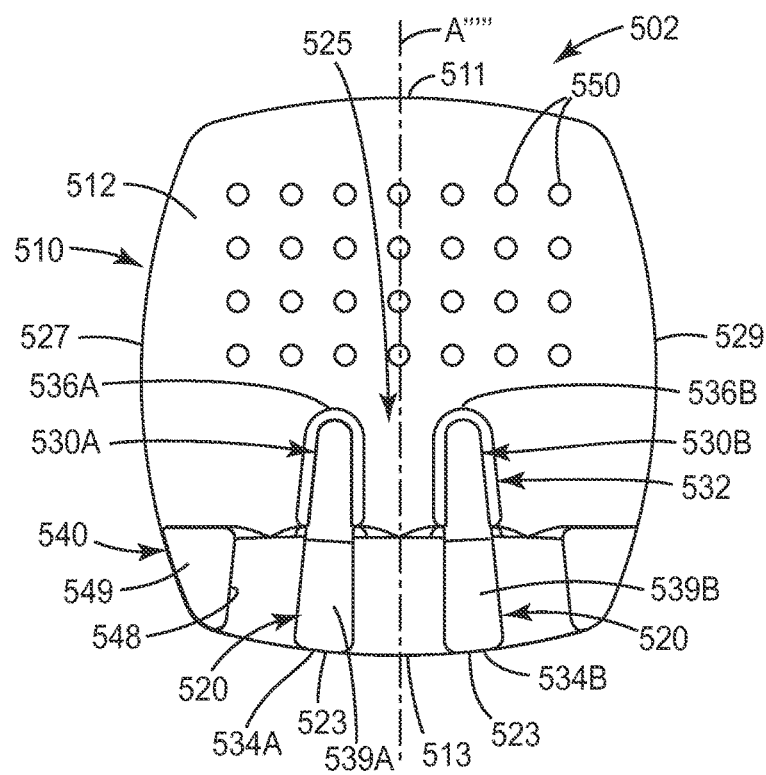
FIG. 18 is a top plan view of the bracket of FIGS. 16 and 17.

FIGS. 16-18 illustrate a bracket 502 according to another embodiment that can be employed with medical article securement systems and methods of the present disclosure, such as, e.g., the medical article securement system 100 of FIGS. 1-6 or other systems described below and illustrated in FIGS. 19-25. By way of example only, FIG. 16 illustrates the medical article 60 coupled to the bracket 502.

The bracket 502 includes a base 510 having a first major surface 512, a distal end 511 and a proximal end 513; two posts 520 defining a channel 525 (e.g., a second channel 525) therebetween, each post 520 having a distal end 521 and a proximal end 523; two arms 530; a land 540 located adjacent (i.e., proximally with respect to the distal end 521 of the posts 520) the posts 520 and the arms 530; a plurality of grooves 548 and/or ridges 549 formed in the first major surface 512 defined by the land 540; and a plurality of openings or perforations 550 formed through the base 510. The base 510 (or the bracket 502 or a system comprising the bracket 502) can also include or define a longitudinal axis A"" (see FIG. 18) that extends in the longitudinal direction (e.g., as defined by the medical article 60) between the distal end 511 and the proximal end 513.

The bracket 502 has a different overall shape and configuration (e.g., the shape of the base 510) than the other brackets described above and illustrated in FIGS. 1-15. In addition, the bracket 502 is different from the others described above in that the bracket 502 includes two arms 530 that extend substantially along the longitudinal axis A"" of the base 510, and along the longitudinal axis A of the medical article 60 when the medical article 60 is coupled to the bracket 502, i.e., longitudinally, rather than laterally.

The bracket 502 includes a first arm 530A located toward a first lateral side 527 (e.g., on the left side of FIG. 18) and a second arm 530B located toward a second lateral side 529 (e.g., on the right side of FIG. 18). Each arm 530A and 530B is coupled (e.g., fixedly) to the base 510 and is spaced a vertical distance from the first major surface 512. The arms 530A and 530B both extend in the same direction and together define a channel 532 (e.g., a first channel 532) under the arms 530A and 530B dimensioned to receive at least a portion of the medical article 60. In some embodiments, as shown, each arm 530A, 530B can be positioned in an at least partially overlapping relationship with the base 510, such that at least a portion of the arm 530A, 530B extends over the first major surface 512 of the base 510.

Each arm 530A, 530B includes a fixed end 534A, 534B coupled to or provided by the post 520, and a free end 536A, 536B. That is, each post 520 can provide a pedestal 537 for an arm 530. In addition, each arm 530A, 530B includes a horizontal projection 539A, 539B that extends substantially parallel to the first major surface 512 of the base 510, such that the horizontal projection 539A, 539B is substantially perpendicular to the respective post 520 (i.e., the pedestal 537). Each horizontal projection 539A, 539B can be considered to include the fixed end 534A, 534B and the free end 536A, 536B. By way of example only, each arm 530A, 530B is illustrated as extending generally distally from the post 520, but the fixed end 534A, 534B of each arm 530A, 530B is located no further distally than the distal end 521 of its respective post 520 (i.e., pedestal 537). In some embodiments, as shown, one or more of the posts 520 and one or more of the arms 530 can be provided by the same structure, such that each post 520 and at least one arm 530 are integrally formed. Two arms 530A and 530B are shown by way of example only, but it should be understood that as many arms 530 as necessary for a given medical article can be employed.

When the medical article 60 is coupled to the bracket 502 (as shown in FIG. 16) and a portion thereof is positioned in the channel 532 defined by the arms 530A and 530B, the arms 530A and 530B can be configured to inhibit movement of the medical article 60 in at least a direction that is generally normal to the first major surface 512 of the base 510, i.e., to inhibit the medical article 60 from being pulled away from a patient's skin.

As mentioned above, each arm 530A and 530B extends generally longitudinally with respect to the longitudinal axis A"" of the base 510 (or the bracket 502 or a system comprising the bracket 502) and further with respect to the longitudinal axis A of the medical article 60 when the medical article 60 is coupled to the bracket 502. As such, the fixed ends 534A, 534B are fixed longitudinal ends 534A, 534B, and the free ends 536A, 536B are free longitudinal ends 536A, 536B.

Unlike the brackets 202 and 302 described above, the arms 530A, 530B of the bracket 502 do not overlap or cross one another. Rather, the arms 530A, 530B extend in the same direction, generally parallel to one another. As shown, in some embodiments, the arms 530 can be identical and symmetrical (e.g., about the longitudinal axis A""), and the arms 530 can extend outwardly from the posts 520 at the same longitudinal position and at symmetrical lateral positions. However, this need not necessarily be the case. For example, in some embodiments, the arms 530 may not be identical in shape or size, and/or the posts 520 may not be centered with respect to the base 510, and/or the arms 530 may extend from the posts 520 at different longitudinal positions or asymmetrical lateral positions.

The distal ends 521 of the posts 520 can be configured to abut the external surface S of the medical article 60 to inhibit at least longitudinal (e.g., proximal) movement of the medical article 60 when the medical article 60 is coupled to the bracket 502. In addition, the arms 530 can be configured to inhibit at least vertical movement of the medical article 60, i.e., away from the base 510 and a patient's skin.

As further shown, in some embodiments, the arms 530A, 530B can be located directly adjacent the post 520, and particularly, directly adjacent the distal end 521 of the post 520, such that the posts 520 and the arms 530 are not separated a longitudinal distance apart. Because of this arrangement, in some embodiments, abutting the external surface S of the medical article 60 adjacent the distal ends 521 of the posts 520 and positioning at least a portion of the medical article 60 (e.g., the middle input catheter 62) in the second channel 525 defined between the posts 520 can occur substantially simultaneously with positioning a portion of the medical article 60 (e.g., the catheter hub 64) in the first channel 532 defined by the arms 530A, 530B. Such action can be accomplished very easily and with a minimal number of steps or forces exerted on the medical article 60, the patient's skin (e.g., the skin 50 illustrated in FIG. 1), or the insertion site (e.g., the insertion site 65 illustrated in FIG. 1). For example, with generally one simple motion, the proximal vertical external surface S of the catheter hub 64 can be abutted or aligned against the distal ends 521 of the posts 520, and the input catheters 62 can be threaded under the arms 530, e.g., even all with one hand in some cases.

As mentioned above, the bracket 502 can further include a land 540 located laterally adjacent the posts 520 and the arms 530 and proximally (or no further distally) with respect to the distal ends 521 of the posts 520. The height of the land 540 can be configured to allow at least a portion of the medical article 60 (e.g., the catheter hub 64) to rest flat against the flat portion of the base 510 located proximally with respect to the post 520, and to allow a portion of the medical article 60 (e.g., the input catheters 62) to pass adjacent the posts 520 and the arms 530.

As mentioned above, the land 540 can be further configured to retain at least a portion of the medical article 60, for example, by including one or more grooves 548 and/or ridges 549 (e.g., longitudinal grooves and/or ridges) dimensioned to receive at least a portion of the medical article 60 (e.g., the input catheters 62). The grooves 548 and/or ridges 549 can be configured to inhibit at least lateral movement of the medical article 60 when the medical article 60 is coupled to the bracket 502.

While not illustrated in FIGS. 16-18, the bracket 502 can further include indicia, similar to the indicia 108 and 208 to provide a visual cue for coupling the medical article 60 to the bracket 502.

The bracket 502 includes a plurality of openings or perforations 550 formed through the base 510 for enhance permeability and breathability. By way of example only, the perforations 550 are formed through the base 510 across an area located between the free ends 536A, 536B of the arms 530A, 530B and the distal end 511 of the base 510. In addition, the first major surface 512, particularly, in the region between the distal end 511 of the base 510 and the post 520 can be configured to receive at least a portion of the medical article 60, such as, for example, the catheter hub 64.

As shown, in some embodiments, the posts 520 and the arms 530 can be fixed with respect to the base 510 and to each other. In the embodiment of FIGS. 16-18, the posts 520 and the arms 530 are integrally formed with the base 510 and to each other; however, this need not be the case. In some embodiments, the posts 520 and the arms 530 can be coupled to the base 510 in order to be fixed with respect to the base 510. In some embodiments, the posts 520 and the arms 530 are directly coupled to the base 510 such that no intervening elements or structures are positioned or coupled between the posts 520 and the base 510, and in some embodiments, the posts 520 and the arms 530 are indirectly coupled to the base 510 by additional structures or elements.

The Flap

As mentioned above, some embodiments of the systems of the present disclosure can include a flap, such as the flap 106 shown in FIGS. 1-4. In some embodiments, the flap 106 can provide sufficient security to inhibit lateral, longitudinal, and/or vertical movement of the medical article (e.g., the medical article 60), to allow one or more of the posts 120 and the arm 130 to be eliminated from the system 100. In some embodiments, the systems of the present disclosure can include a flap and a bracket (e.g., any of the above-described brackets 102, 202, 302, 402, and 502) comprising a base (e.g., any of the bases 110, 210, 310, 410, and 510) and an arm (e.g., one or more of the arms 130, 230, 330, 430 and 530); and the flap (e.g., the flap 106) and the arm can together inhibit at least vertical movement of the medical article, and in some embodiments, can further inhibit lateral and/or longitudinal movement of the medical article.

The flaps of the present disclosure can be flexible, particularly, relative to the brackets of the present disclosure, and the brackets can be relatively rigid, relative to the flaps. The flaps can therefore provide a more pliable and compliant element to the systems of the present disclosure to complement and supplement the structural rigidity and integrity of the brackets. The robustness of the brackets of present disclosure can offer facile, reliable, repeatable and secure coupling and decoupling of a medical article to the bracket, and the flaps of the present disclosure can provide additional security. The flaps of the present disclosure can also provide a certain level of flexibility depending on the specific medical article that is being coupled to the system, because the flap can be sized and configured to accommodate a variety of medical article configurations and sizes. For example, the flap can be long enough to accommodate a variety of medical articles, and can simply be pulled further over the bracket and medical article in cases of smaller medical articles. The flexibility of the flap is generally sufficient to prevent the flap from breaking (e.g., adjacent its hinge, if employed, as described below), while still being rigid enough to provide structural integrity and to inhibit movement of the medical article when the medical article is coupled to the system.

The flaps of the present disclosure can be formed of a variety of materials, including, but not limited to, at least one of a fabric, a woven fibrous web, a nonwoven fibrous web, a knit, a polymeric film, an elastomer, combinations thereof, or a laminate structure comprising any of the above. In some embodiments, the flap can include a backing (e.g., formed of any of the above-listed materials) and an adhesive (e.g., where the adhesive serves as securing means for the flap). In some embodiments, the flap can be formed from a medical tape, such as medical tapes available under the tradenames DURAPORE® and TRANSPORE® from 3M Company, St. Paul, Minn. The flaps of the present disclosure (i.e., the backing of the flap) generally needs to be sufficiently flexible to conform to a portion of the medical article 60 and sufficiently rigid to resist deformation when axial, vertical and/or lateral forces are applied. In some embodiments, the flap (i.e., the backing of the flap) can have a thickness ranging from about 1 mil (0.02 mm) to about 6 mil (0.15 mm). The securing means of the flaps should generally have sufficient adhesion to securely attach to the medical article 60 while also being able to be removed cleanly (i.e., with little to no residue, if the securing means comprises an adhesive).

The flaps of the present disclosure will first generally be described with respect to the flap 106 of FIGS. 1-4. Then, a variety of alternative embodiments will be described with respect to FIGS. 19-25. It should be understood that any of the features and elements described with respect to the flap 106 can equally be applied to the later embodiments of FIGS. 19-25, and vice versa. In addition, the flap configurations described and illustrated in FIGS. 1-4 and 19-25 are shown as being used in combination with specific systems and brackets for illustration purposes only, and it should be understood the flap configurations illustrated in FIGS. 1-4 and 19-25 can also be used in combination with other brackets and systems of the present disclosure.

Additional details regarding flaps of the present disclosure can be found in co-pending U.S. Application No. 61/695,888, filed Aug. 31, 2012, which is incorporated herein by reference.

As shown in FIGS. 1-4, the flap 106 can include a first fixed end 170 and a second free end 172 that is movable with respect to the first fixed end 170, the bracket 102 and the medical article 60 between a first position $P_1$ (see FIGS. 2-4) in which the flap 106 is not positioned over the medical article 60 and/or the bracket 102 and a second position $P_2$ (see FIG. 1) in which at least a portion of the flap 106 is positioned over (i.e., in overlapping relationship with) the bracket 102 (and the medical article 60 when the medical article 60 is coupled to the system 100). When the free end 172 of the flap 106 is in the second position $P_2$, the flap 106 defines a channel 173 (see FIG. 1) thereunder that can be dimensioned to receive at least a portion of the medical article 60 and that, in some embodiments, can be generally aligned with the channel 132 defined by the arm 130. In some embodiments, the channel 173 can be oriented generally parallel to the longitudinal axis A' of the base 110, e.g., in embodiments in which the flap 106 extends generally laterally with respect to the longitudinal axis A' when in the second position $P_2$. That is, in some embodiments, the flap 106 can extend across the longitudinal axis A' of the base 110 when the flap 106 is in the second position $P_2$.

The flap 106 can also be positioned over the medical article 60 when in the second position $P_2$ when the medical article 60 is coupled to the bracket 102. In the second position $P_2$, the flap 106 can further inhibit movement of the medical article 60 relative to the bracket 102. In addition, the flap 106 is different from a separately provided piece of tape or other strip or fastener, because the flap 106 is provided by the system 100, and particularly is provided in a specific configuration and arrangement relative to the other components of the system 100 to provide facile and effective use of the flap 106. That is, the first fixed end 170 of the flap 106 can be coupled to the bracket 102 when the second free end 172 of the flap 106 is in the first position $P_1$ and the second position $P_2$, e.g., the flap 106 is somehow coupled to the system 100, and particularly, the bracket 102, even before the flap 106 is used.

In some embodiments, the flap 106 can be directly coupled to the bracket 102 (e.g., to an edge 103 of the bracket 102 and/or to the second major surface 114 of the bracket, as described below), and in some embodiments, the flap 106 can be indirectly coupled to the bracket 102 (e.g., coupled to or provided by another component of the system 100 that is coupled to the bracket 102, such as the base dressing 104).

In some embodiments, as shown, the flap 106 can be configured to extend laterally with respect to the longitudinal axis A' of the bracket 102 and with respect to the longitudinal axis A of the medical article 60. In such embodiments, the flap 106 can be configured to extend from its fixed end 170 to its free end 172 across the bracket 102 and medical article 60 in a direction that is different from the direction in which the arm 130 extends from its fixed end 134 to its free end 136, e.g., in a direction substantially opposite that of the arm 130. Said another way, in some embodiments, the flap 106 can have its fixed end 170 on a first lateral side 127 (see FIG. 4) of the base 110, and the arm 130 can have its fixed end 134 on a second lateral side 129 (see FIG. 4) opposite the first lateral side 127, such that the flap 106 and the arm 130 oppose one another. In such embodiments, the flap 106 and the arm 130 can together inhibit lateral (e.g., bilateral) movement of the medical article 60, and the flap 106 and the 130 can complement one another. In such embodiments, the arm 130 can be configured to inhibit lateral movement of the medical article 60 in at least a first direction and the flap 106 can be configured to inhibit lateral movement of the medical article 60 in at least at least a second direction that is different from (e.g., opposite) the first direction. The arm 130 and the flap 106 can together inhibit vertical movement of the medical article 60.

In the embodiment illustrated in FIGS. 1-4, the flap 106 is oriented substantially perpendicularly with respect to the longitudinal axis A' of the base 110; however, it should be understood that in some embodiments, the flap 106 can extend at an oblique angle with respect to the longitudinal axis A', such that the flap 106 still includes a lateral component and crosses over the bracket 102 but not at a 90-degree angle (see, e.g., FIG. 23, described below). That is, in some embodiments, the flap 106 can be oriented at a non-zero and non-right angle with respect to the longitudinal axis A' of the base 110 of the bracket 102, at least when the free end 172 of the flap 106 is in the second position $P_2$.

The system 100 is illustrated as including only one flap 106, but in some embodiments, the system 100 can include a plurality of flaps 106, and in such embodiments, the plurality of flaps 106 can together inhibit at least vertical movement of the medical article 60. In embodiments employing a plurality of flaps 106, the flaps 106 can be configured to extend across the medical article 60 and the bracket 102 in opposite directions, in the same direction, or a combination thereof. In addition, in some embodiments, at least two of the plurality of flaps 106 can be configured to overlap, intersect and/or cross (e.g., criss-cross) one another for added security. In some embodiments, the plurality of flaps 106 can include at least two flaps 106 that extend opposite one another (i.e., in opposite directions across the bracket 102) and are not spaced longitudinally apart, such that the free ends 172 of the flaps 106 directly overlap one another when in their second positions $P_2$. Furthermore, in some embodiments employing a plurality of flaps 106, the flaps 106 can be configured to extend laterally with respect to the longitudinal axis A' of the bracket 102 and with respect to the longitudinal axis A of the medical article 60. In such embodiments, the plurality of flaps 106 can be positioned directly adjacent one another, on top of one another, or spaced a longitudinal distance apart. For example, in some embodiments, spacing the flaps 106 longitudinally allows for the flaps 106 to be located on either side of another component of the system 100, such as the arm 130 (e.g., proximally and distally with respect to the arm 130).

As shown in FIG. 1, in some embodiments, the fixed end 170 of the flap 106 can include a hinge (e.g., a living hinge) 174 about which the free end 172 of the flap 106 can pivot to move between the first position $P_1$ and the second position P$_2$. Such a hinge 174 can be formed in the flap material itself, or in another component of the system 100 to which the flap 106 is coupled, such as the base dressing 104. As shown in FIG. 1, in some embodiments, the flap 106 can be located adjacent an edge 103 of the bracket 102. As further shown in FIG. 1, in some embodiments, e.g., in embodiments in which the flap 106 extends laterally with respect to the longitudinal axis A' of the bracket 102, the hinge 174 can be located adjacent a lateral side (e.g., the first lateral side 127 or the second lateral side 129) of the base 110 of the bracket 102.

As shown in FIGS. 1-4, the bracket 102 and the flap 106 can be coupled to the first side 116 of the base dressing 104. In some embodiments, the fixed end 170 of the flap 106 can be coupled (e.g., sandwiched) between the bracket 102 and the base dressing 104, i.e., between the second major surface 114 of the bracket 102 and the first side 116 of the base dressing 104. Such an embodiment is illustrated in FIGS. 1-4. Such a configuration of sandwiching a portion of the flap 106 between the bracket 102 and the base dressing 104 can provide added security.

The flap 106 can be coupled to portions of the bracket 102 or the base dressing 104, or between the bracket 102 and the base dressing 104 using a variety of coupling means including, but not limited to, one or more of adhesives, cohesives, magnets, welding (e.g., sonic (e.g., ultrasonic) welding), any thermal bonding or heat sealing technique (e.g., heat and/or pressure applied to one or both of the components to be coupled), other suitable coupling means, or combinations thereof.

In some embodiments, the flap 106 can be provided by another component of the system 100, such as the base dressing 104. For example, in some embodiments, at least a portion of the base dressing 104 can be peeled from the remainder of the base dressing 104 to function as the flap 106. By way of further example, in some embodiments, the flap 106 can be provided by an extension of the base dressing 104. In some embodiments, the flap 106 and the base dressing 104 can be integrally formed.

Additionally or alternatively, in some embodiments, the fixed end of the flap 106 can be coupled to the first major surface 112 of the base 110 of the bracket 102, such that the free end 172 of the flap 106 then overlaps the fixed end 170 when in the second position P$_2$. Still, in some embodiments, the flap 106 (and particularly, the fixed end 170 of the flap 106) can be coupled to the base dressing 104, or a different portion of the bracket 102. Such alternative flap configurations will be described in greater detail below with reference to FIGS. 19-25. In some embodiments, a combination of flap configurations can be employed together in one system.

At least the free end 172 of the flap 102, and sometimes an entire side of the flap 106, can include securing means. Such securing means can include, but are not limited to, one or more of an adhesive, a cohesive, a hook and loop fastener that mates with a pad located on another element of the system 100 (e.g., the base dressing 104 on an opposite side of the bracket 102 from the fixed end 170 of the flap 106), other suitable securing or fastening means, or combinations thereof.

The flap 106 can include a first side 176 and a second side 178 opposite the first side 176. The first side 176 (or at least a portion thereof adjacent the free end 172 of the flap 106) can be configured to face the medical article 60 and the first major surface 112 of the base 110 of the bracket 102 when the free end 172 of the flap 106 is in the second position P$_2$. The second side 178 of the flap 106 can be configured to face away from the medical article 60 and the bracket 102 when the free end 172 of the flap 106 is in the second position P$_2$. In some embodiments, at least a portion of the first side 176 of the flap 106 can include the securing means.

By way of example only, in the embodiment illustrated in FIGS. 1-4, the first side 176 of the flap 106 includes adhesive on a majority of the first side 176, and particularly, on a portion of the first side 176 adjacent the free end 172. As such, a release liner 179 can be coupled to the first side 176 which can be removed prior to applying the flap 106 over the medical article 60 and the bracket 102.

As mentioned above and described in greater detail below (see FIG. 19), in some embodiments, the second side 178 of the flap 106 can be coupled (e.g., adhered) to the first major surface 112 of the base 110 of the bracket 102.

As shown by way of example only, in some embodiments, the free end 172 of the flap 102 can be enlarged relative to adjacent portions of the flap 106 to facilitate grasping the free end 172. For example, as shown in FIGS. 1-4, the flap 106 includes a tab 180 in its free end 172. In some embodiments, as shown in FIGS. 1-4, the tab 180 can be free of the securing means (e.g., adhesive) to facilitate grasping the tab 180.

In some embodiments, as shown in FIG. 1, the flap 106 can be dimensioned to be longer than the bracket 102 in a direction in which the flap 106 extends across the bracket 102 when the free end 172 of the flap 106 is in the second position P$_2$. For example, as shown, the flap 106 can have a length that is greater than a lateral width of the bracket 102, particularly at the longitudinal position of the bracket 102 at which the flap 106 is located.

Additional exemplary embodiments of systems of the present disclosure comprising flaps will now be described with respect to FIGS. 19-25. FIGS. 19-25 illustrate various systems, brackets, and flaps of the present disclosure, wherein like numerals represent like elements. The flaps of FIGS. 19-25 share many of the same elements, features, and functions as the flap 106 described above with respect to FIGS. 1-4. Reference is made to the description above accompanying FIGS. 1-4 for a more complete description of the features and elements (and alternatives to such features and elements) of the embodiments illustrated in FIGS. 19-25. Any of the features described above with respect to FIGS. 1-4 can be applied to the embodiments of FIGS. 19-25, and vice versa.

Figure 19:
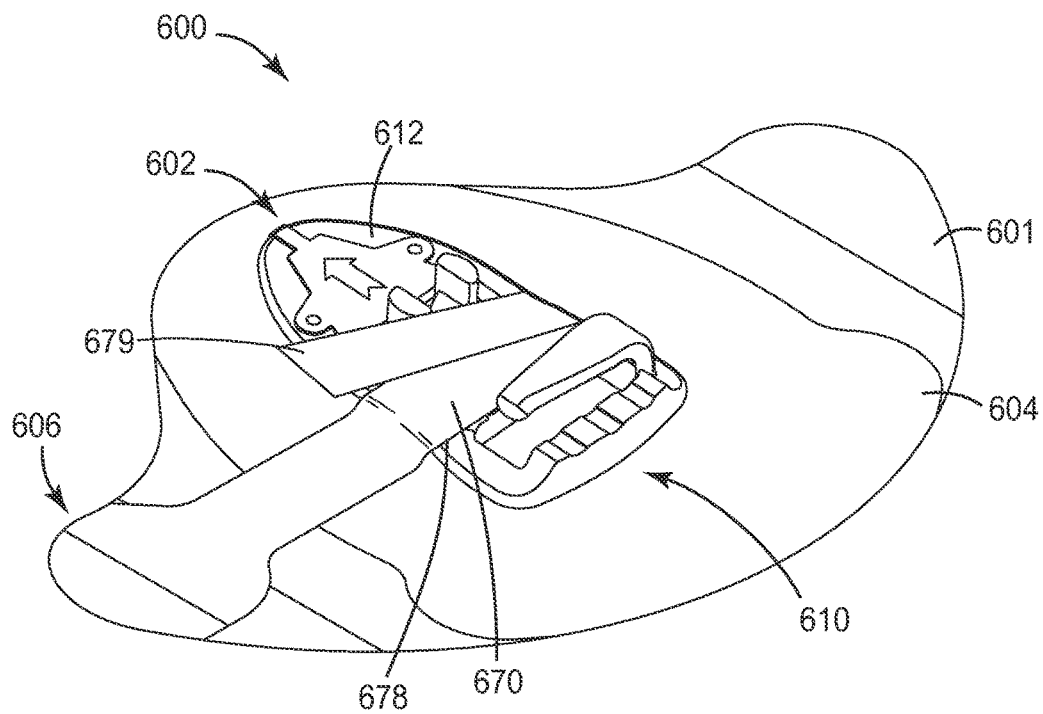
FIG. 19 is a front perspective view of a medical article securement system according to another embodiment of the present disclosure.

FIG. 19 illustrates a system 600 according to another embodiment of the present disclosure. The system 600 includes a bracket 602 comprising a base 610; a base dressing 604; and release liners 601 substantially similar to those of FIGS. 1-4, along with a flap 606. The flap 606 is substantially the same as the flap 106 of FIGS. 1-4, except that a second side 678 of a fixed end 670 of the flap 606 is coupled to a first major surface 612 of the base 610, rather than being coupled between the base 610 and the base dressing 604. Any of the coupling means described above can be used to couple the fixed end 670 of the flap 606 to the first major surface 612 of the base 610. In such embodiments, as shown, a release liner 679 can be coupled all the way to a terminus of the fixed end 170 of the flap 106.

Figure 20:
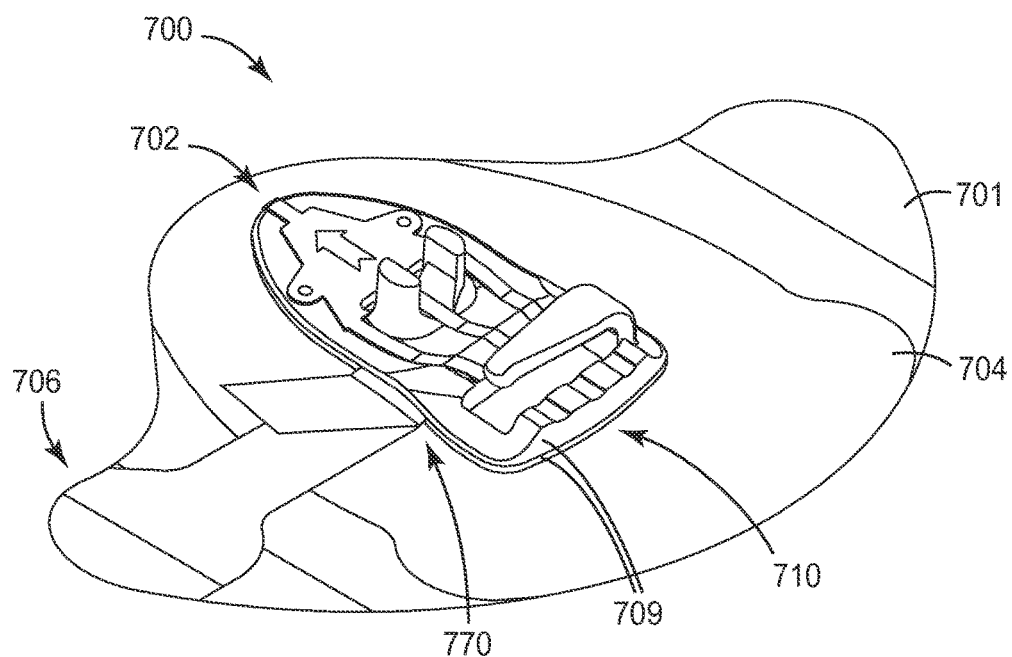
FIG. 20 is a front perspective view of a medical article securement system according to another embodiment of the present disclosure.

FIG. 20 illustrates a system 700 according to another embodiment of the present disclosure. The system 700 includes a bracket 702 comprising a base 710; a base dressing 704; and release liners 701 substantially similar to those of FIGS. 1-4, along with a flap 706. The flap 706 is substantially the same as the flap 106 of FIGS. 1-4, except that a fixed end 770 of the flap 706 is coupled (e.g., sandwiched) between two layers 709 of the base 710, rather than being coupled between the base 710 and the base dressing 704. Any of the coupling means described above can be used to couple the fixed end 770 of the flap 706 between the layers 709 of the base 710.

Figure 21:
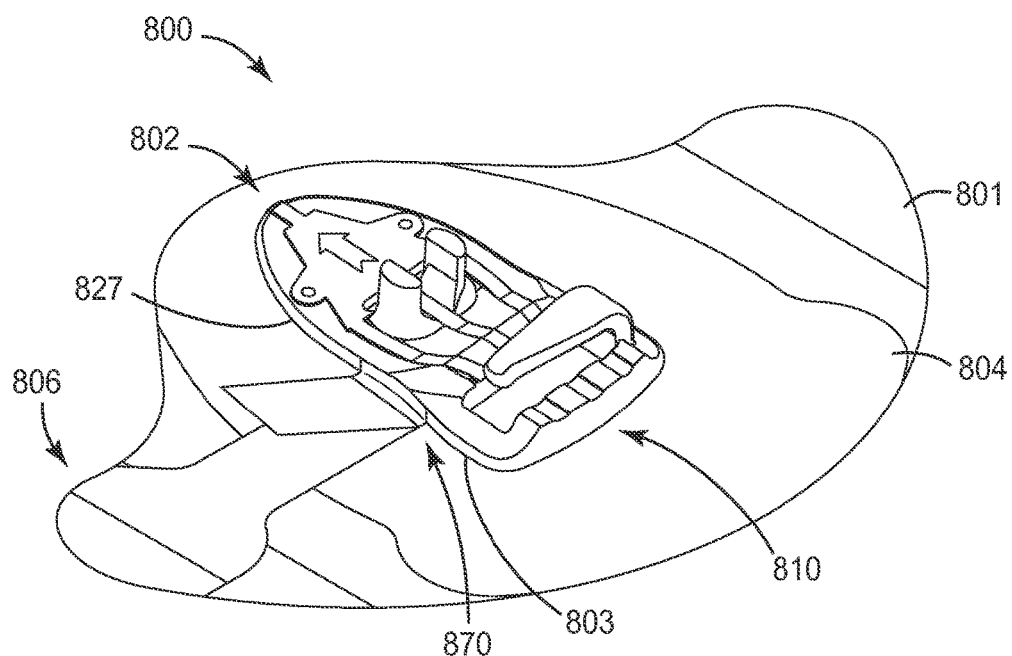
FIG. 21 is a front perspective view of a medical article securement system according to another embodiment of the present disclosure.

FIG. 21 illustrates a system 800 according to another embodiment of the present disclosure. The system 800 includes a bracket 802 comprising a base 810; a base dressing 804; and release liners 801 substantially similar to those of FIGS. 1-4, along with a flap 806. The flap 806 is substantially the same as the flap 106 of FIGS. 1-4, except that a fixed end 870 of the flap 806 is coupled to an edge 803 of the base 810 of the bracket 802, and particularly to an edge 803 on a first lateral side 827 of the base 810 (or bracket 802), rather than being coupled between the base 810 and the base dressing 804. Any of the coupling means described above can be used to couple the fixed end 870 of the flap 806 to the edge 803 of the base 810.

Figure 22:
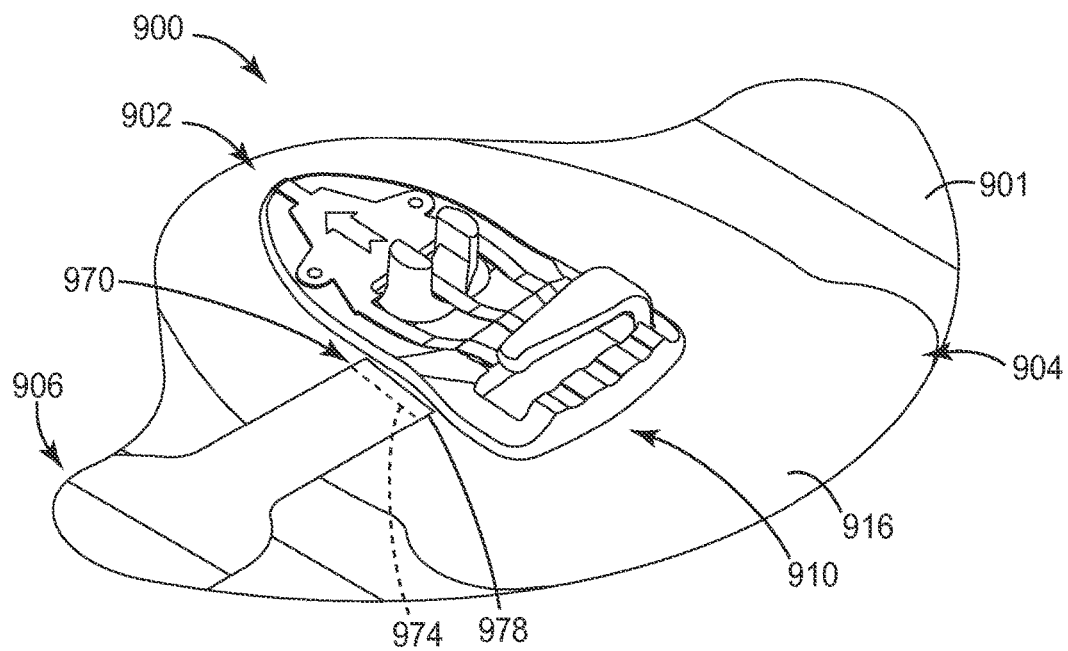
FIG. 22 is a front perspective view of a medical article securement system according to another embodiment of the present disclosure.

FIG. 22 illustrates a system 900 according to another embodiment of the present disclosure. The system 900 includes a bracket 902 comprising a base 910; a base dressing 904; and release liners 901 substantially similar to those of FIGS. 1-4, along with a flap 906. The flap 906 is substantially the same as the flap 106 of FIGS. 1-4, except that a fixed end 970 of the flap 906 (and particularly, a second side 978 of the fixed end 970) is coupled to a first side 916 of the base dressing 904, rather than being coupled between the base 910 and the base dressing 904. As such, the flap 906 can include a hinge (e.g., a living hinge) 974 located adjacent the portion of the fixed end 970 that is coupled to the base dressing 904. Any of the coupling means described above can be used to couple the fixed end 970 of the flap 906 to the base dressing 904.

Figure 23:
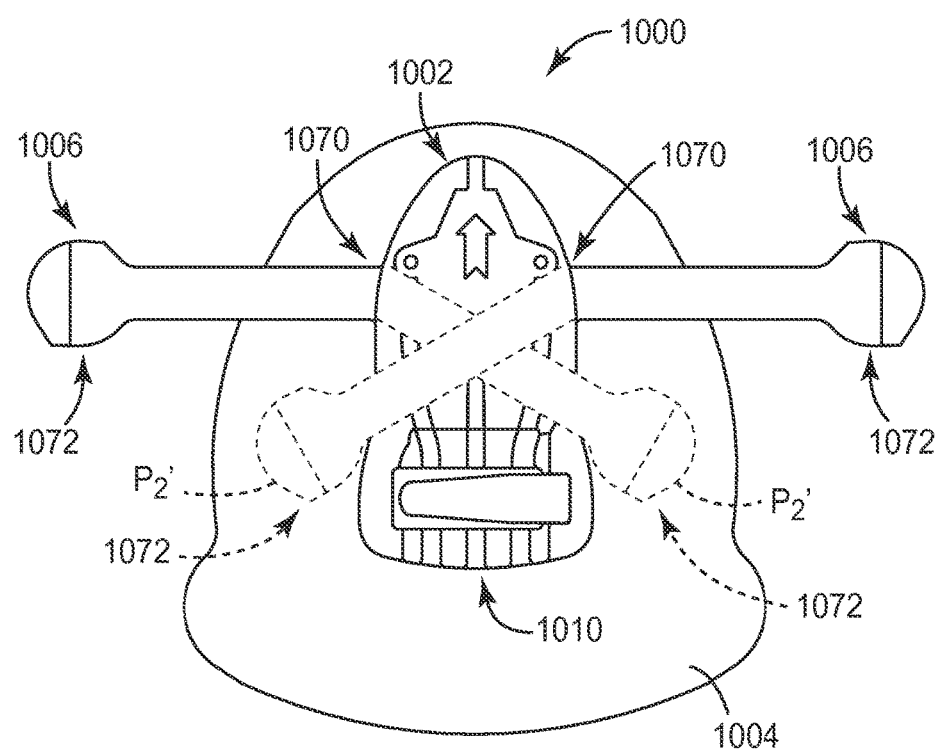
FIG. 23 is a top plan view of a medical article securement system according to another embodiment of the present disclosure.

FIG. 23 illustrates a system 1000 according to another embodiment of the present disclosure. The system 1000 includes a bracket 1002 comprising a base 1010; a base dressing 1004; and two flaps 1006. The two flaps 1006 each include a fixed end 1070 that is coupled between the base 1010 of the bracket 1002 and the base dressing 1004 by way of example only, and the flaps 1006 are configured such that when free ends 1072 of the flaps 1006 are positioned in their respective second positions $P_2'$ (shown in dashed lines), the flaps 1006 overlap, intersect, or cross one another for added security.

The bracket 1002 is substantially the same as that of the bracket 102 of FIGS. 1-6, except that the bracket 1002 has no posts by way of example only. However, it should be understood that the flaps 1006 and the bracket 1002 can be configured such that the flaps 1006 can overlap, intersect and/or cross one another and still accommodate the posts 120 of the bracket 102.

The fixed ends 1070 of the flaps 1006 are shown as being coupled between the bracket 1002 and the base dressing 1004 at the same longitudinal position of the base 1010 of the bracket 1002; however, it should be understood that the fixed ends 1070 of the flaps 1006 can instead be located at different longitudinal positions from one another.

Figure 24:
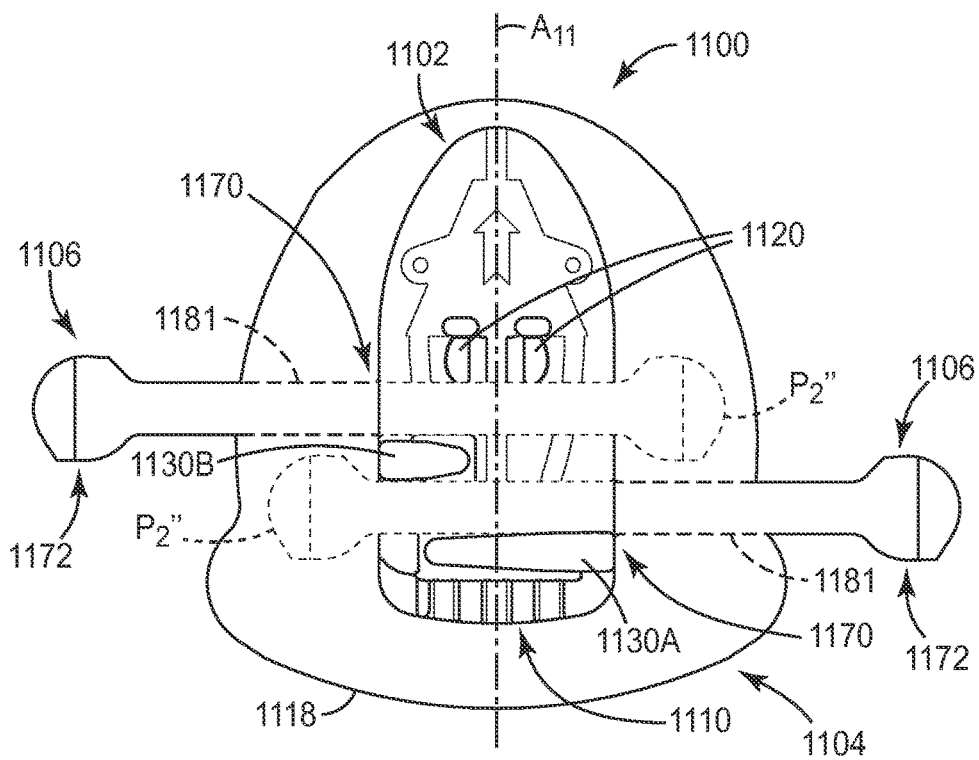
FIG. 24 is a top plan view of a medical article securement system according to another embodiment of the present disclosure.

FIG. 24 illustrates a system 1100 according to another embodiment of the present disclosure. The system 1100 includes a bracket 1102 comprising a base 1110; a base dressing 1104; and two flaps 1106. The bracket 1102 is substantially the same as that of the bracket 202 of FIGS. 7-9 and includes two posts 1120, a first arm 1130A, and a second arm 1130B.

The flaps 1106 each include a fixed end 1170 and a free end 1172 and extend laterally with respect to a longitudinal axis $A_{11}$ but in opposite directions, such that the flaps 1106 extend past one another when their free ends 1172 are in their respective second positions $P_2''$ (shown in dashed lines), providing inhibition of lateral (e.g., bilateral) movement of a medical article coupled to the system 1100. The flaps 1106 are spaced a longitudinal distance apart from one another, and particularly to accommodate the first second arm 1130B therebetween.

The flaps 1106 represent an example of flaps being provided by the base dressing 1104. Specifically, the free ends 1172 of the flaps 1106 are extensions of the base dressing 1104, and a portion of the flaps 1106 is perforated from the rest of the base dressing 1104 (e.g., along perforations 1181) to allow the flaps 1106 to each be peeled away from the remainder of the base dressing 1104 without disrupting the adhesion of the remainder of the base dressing 1104 from a patient's skin. In some embodiments, a second (e.g., bottom) side 1118 of the dressing 1104 in the region of the portion of the flaps 1106 that will be peeled back can be free of any skin-contact adhesive.

The free ends 1172 of the flaps 1106 are shown as extending out past an outer edge of the base dressing 1104; however, it should be understood that this need not be the case. Rather, in some embodiments, the free ends 1172 can merely be an outer edge portion of the dressing 1104, and the flaps 1106 can be formed when the flaps 1106 are peeled back from the remainder of the base dressing 1104.

The bracket 1102 is shown by way of example only as including two arms 1130A and 1130B and being substantially similar to the bracket 202 of FIGS. 7-9; however, it should be understood that the flap configuration illustrated in FIG. 24 can instead be employed with any other bracket of the present disclosure, and can include fewer or more than two flaps.

Figure 25:
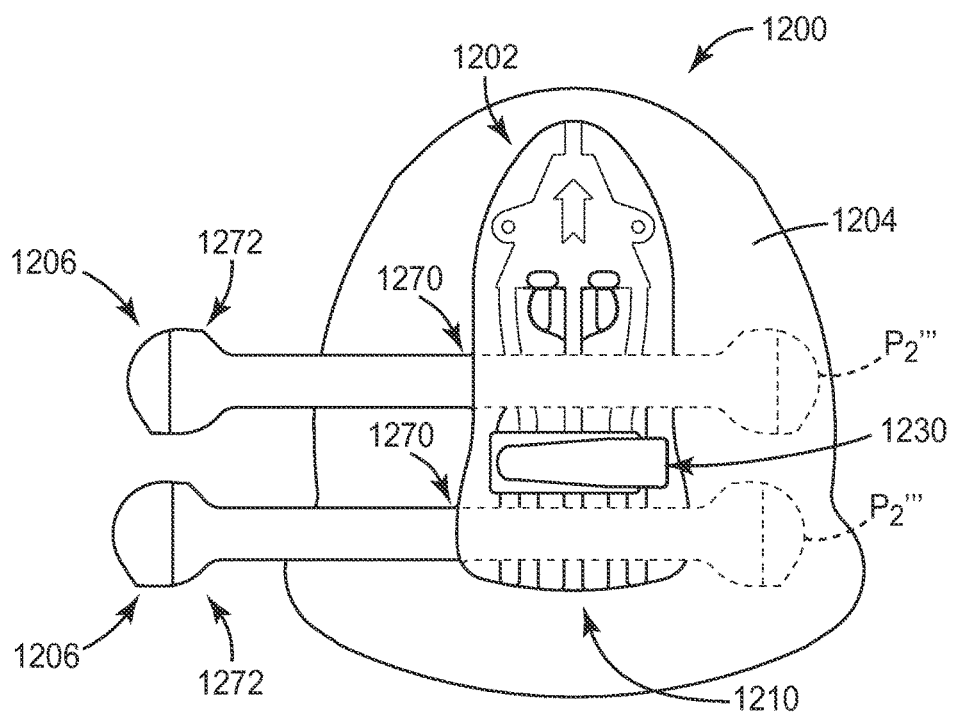
FIG. 25 is a top plan view of a medical article securement system according to another embodiment of the present disclosure.

FIG. 25 illustrates a system 1200 according to another embodiment of the present disclosure. The system 1200 includes a bracket 1202 comprising a base 1210 and an arm 1230; a base dressing 1204; and two flaps 1206. The bracket 1202 is substantially the same as that of the bracket 102 of FIGS. 1-6, except that the base 1210 is extended proximally from the arm 1230 to provide addition surface area for securing an additional flap 1206.

The two flaps 1206 each include a fixed end 1270 that is coupled between the base 1210 of the bracket 1202 and the base dressing 1204 by way of example only, and the flaps 1206 are spaced apart longitudinally to accommodate the arm 1230 of the bracket 1202 therebetween, such that when free ends 1272 of the flaps 1206 are positioned in their respective second positions $P_2'''$ (shown in dashed lines), the arm 1230 is located between the flaps 1206.

The flaps 1206 are illustrated as extending laterally across the bracket 1202 in the same direction; however, it should be understood that the flaps 1206 can instead oppose one another, overlap, and/or criss-cross, etc.

The Indicia

As mentioned above, the present disclosure can provide indicia for use with a medical article securement system of the present disclosure that includes a representation (e.g., a pictorial representation) of a medical article of interest, such that the indicia mimics the overall shape, appearance and/or configuration of the medical article to provide a visual cue for how to couple the medical article to the medical article securement system. Such indicia can enhance the usability of the systems of the present disclosure and can minimize operator errors when applying the systems to patients and coupling medical articles to the systems.

Such indicia can be coupled to or provided by a bracket of the system, and particularly, can be coupled to or provided by a base of the bracket.

In addition to the representation of the medical article, the indicia can include directional cues, such as arrows, to indicate how the system should be oriented relative to another device, structure, or portion of a patient's body. Base dressings of the present disclosure can also include such directional cues. For example, as shown in FIGS. 2-4, the indicia 108 includes a directional cue (e.g., an arrow) 185 that represents how the system 100 (or the bracket 102) should be positioned relative to the insertion site 65, or where the insertion site 65 should be located relative to the system 100 when the system 100 is applied to the skin 50. Namely, in the embodiment shown in FIGS. 2-4, the arrow 185 should be pointing toward the insertion site 65 in use.

The indicia can include a variety of markings, graphics, or the like, in order to represent a medical article. For example, in some embodiments, the indicia can include a two-dimensional representation of the outline, outer contours, or outer periphery of a medical article. As such, the indicia may be a simplified representation of the medical article, but it will be clear to a user how to orient the medical article relative to the system (e.g., to a bracket of the system), based on the caricature or representation of the medical article provided by the indicia.

Additional details regarding indicia of the present disclosure can be found in co-pending U.S. Application No. 61/695,892, filed Aug. 31, 2012, which is incorporated herein by reference.

The indicia of the present disclosure will first generally be described with respect to the indicia 108 of the embodiment of FIGS. 1-6 (as shown in FIGS. 1-4). Then, alternative embodiments will be described with respect to FIGS. 26-27. It should be understood that any of the features and elements described with respect to the indicia 108 of FIGS. 1-6, as well as the indicia of FIGS. 26-27 can be applied to any of the systems of the present disclosure. In addition, the indicia configurations described and illustrated in FIGS. 1-4 and 26-27 are shown as being used in combination with specific systems and brackets for illustration purposes only, and it should be understood the indicia configurations illustrated in FIGS. 1-4 and 26-27 can also be used in combination with other brackets and systems of the present disclosure.

As shown in FIGS. 1-4 by way of example only, the indicia 108 can be configured to represent the overall shape, appearance and/or configuration of the medical article 60, particularly of a catheter system. As a result, as shown in FIG. 4, the indicia 108 includes a first portion 186 configured to mimic or represent the input catheters 62, a second portion 188 configured to mimic or represent the catheter hub 64, and a third portion 190 configured to mimic or represent the output catheter 66. Specifically, by way of example only, the indicia 108 includes a portion (e.g., the second portion 188) located adjacent (e.g., directly adjacent) the posts 120 to illustrate that the catheter hub 64 should be positioned directly adjacent the distal ends 121 of the posts 120. In addition, a portion (e.g., the first portion 186) of the indicia 108 is located adjacent the arm 130 and/or on or adjacent the land 140 (e.g., in the grooves 148) to illustrate that the input catheters 62 should be passed under the arm 130 into the channel 132, over the land 140, and in (e.g., snapped into) the grooves 148. In brackets employing a land 140 having multiple portions (e.g., the distal portion 142 and the proximal portion 144) as well as grooves 148 and/or ridges 149, the indicia 108 can be located on or adjacent one or both portions 142, 144 of the land 140 and/or on or adjacent the grooves 148 and/or the ridges 149 to illustrate how the medical article 60 (or portions thereof) should be positioned relative to those portions of the bracket 102. Any other specific features of the brackets of the present disclosure can also include portions of the indicia 108 located on or adjacent them to illustrate how the medical article 60 should be coupled to the bracket 102 relative to those specific elements or features.

The mere representation of the medical article 60 in the indicia 108 defines an orientation of the medical article 60 with respect to the bracket 102 (and to the system 100); however, as mentioned above, in some embodiments, the indicia 108 can further include additional directional cues, such as arrows (e.g., the arrow 185), or the like.

As shown in FIGS. 1-4, the indicia 108 is not exactly identical to the overall shape of the medical article 60, but the indicia 108 is clearly representative of the medical article 60. As such, in some embodiments, the indicia 108 can be somewhat generic or universal to a variety of medical articles, particularly within a given type of medical articles, such as catheter systems. In some embodiments, the indicia 108 can be sized similarly to the medical article 60. For example, with respect to the indicia 108 and the medical article 60, the portions 186, 188 and 190 of the indicia 108 can be somewhat similar in size (e.g., diameter) to the input catheters 62, somewhat similar in size (e.g., length and width) to the catheter hub 64, and somewhat similar in size (e.g., diameter) to the output catheter 66.

In some embodiments, the indicia 108 can be coupled to the bracket 102 (e.g., directly or indirectly). In such embodiments, the indicia 108 can be coupled either to the first major surface 112 of the base 110 or to the second major surface 114 of the base 110.

In some embodiments, the indicia 108 can be embedded within and/or integrally formed with the bracket 102. As shown in FIGS. 1-4, in the embodiment of FIGS. 1-6, the indicia 108 can be integrally formed (e.g., co-molded, e.g., co-extruded or co-injection molded) with the base 110 of the bracket 102. In such embodiments, the indicia 108 can be provided anywhere throughout the height of the base 110 of the bracket 102 (e.g., anywhere between being on top of the first major surface 112, being between the first major surface 112 and the second major surface 114, and being on the bottom of the second major surface 114). By way of example only, the indicia 108 is illustrated in FIGS. 1-4 as being co-injection molded onto the first major surface 112 of the base 110 of the bracket 102. However, it should be understood that the indicia 108 can instead be co-molded with the second major surface 114 of the base 110, or provided in any of the other manners described herein.

In some embodiments, the indicia 108 can have at least one optical property that is different than at least adjacent portions of the base 110 of the bracket 102 to allow the indicia 108 to be easily seen and contrasted with other portions of the base 110. Such optical properties can include, but are not limited to, one or more of color, shade, hue, transparency/translucency/opacity, reflectance, gloss or shine, refractive index, fluorescence, other suitable optical properties, or combinations thereof. Such optical properties can typically be visually distinguishable by the naked human eye.

In some embodiments, the indicia 108 can be formed of the same or a different material (e.g., a friction control material of a higher coefficient of friction) than the at least adjacent portions of the base 110 of the bracket 102. In embodiments in which the indicia 108 is formed of a different material, the indicia 108 can be provided on the first major surface 112 of the base 110 and can be formed of a material that provides "grip" or resistance to inhibit the medical article 60 from sliding on the first major surface 112 of the base 110 when the medical article 60 is coupled to the bracket 102. For example, in some embodiments, the indicia 108 can be formed of an elastomeric material. As such, in some embodiments, the indicia 108 can further inhibit longitudinal and/or lateral movement of the medical article 60.

As mentioned above, in some embodiments, the indicia 108 can be coupled to or embedded in the bracket 102, and particularly, the base 110. Such "coupling" includes various paints, prints, pigments, dyes, or the like being painted or printed on a surface of the base 110 (e.g., the first major surface 112 or the second major surface 114, e.g., if the base 110 is transparent), as well as being co-formed (e.g., co-molded) with the bracket 102. "Embedding" may include, e.g., dyes or inks that may absorb into a surface to which it is applied.

Still, in other embodiments, the indicia 108 may be embossed or otherwise shaped into the base 110 itself, e.g., by being embossed into the first major surface 112 to form a depressed region that is easily distinguishable from its surroundings.

Figure 26:
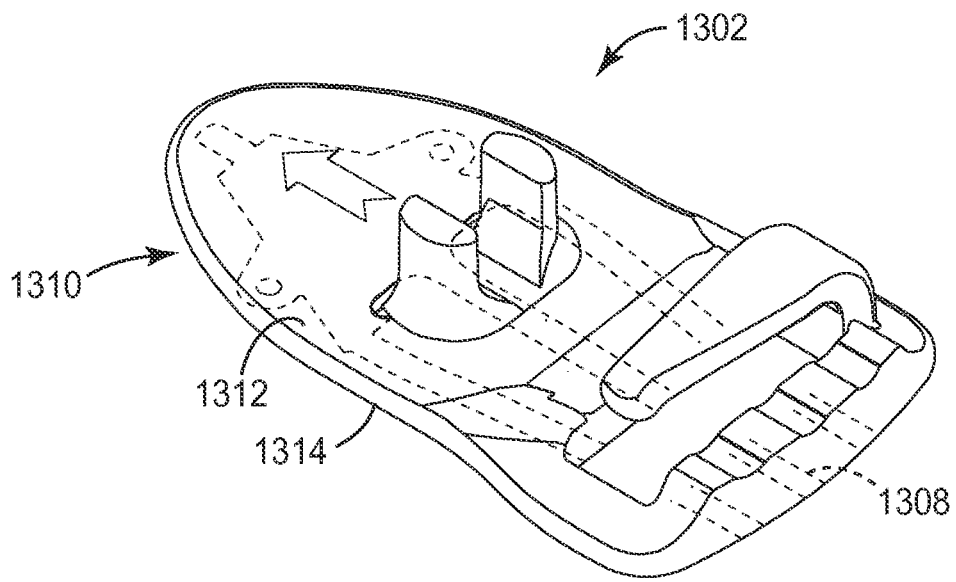
FIG. 26 is a front perspective view of a bracket comprising indicia according to another embodiment of the present disclosure.
Figure 27:
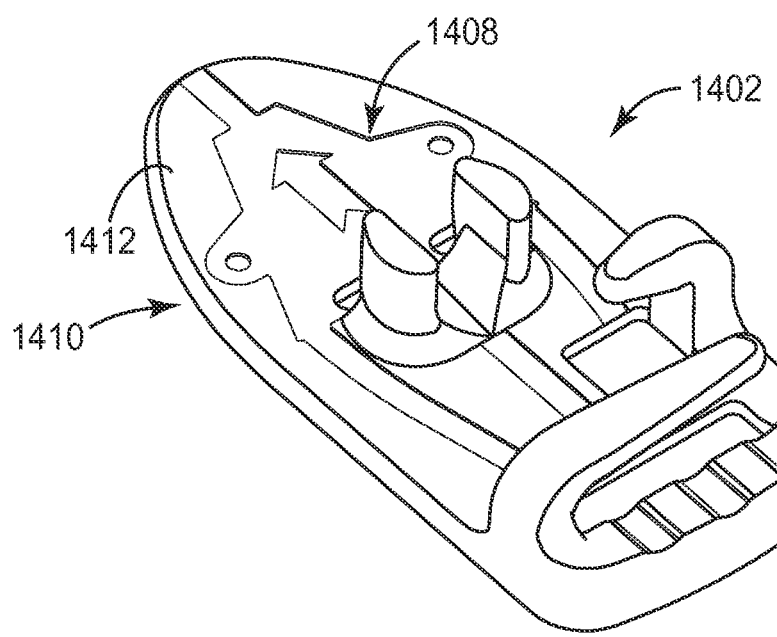
FIG. 27 is a front perspective view of a bracket comprising indicia according to another embodiment of the present disclosure.

Additional exemplary embodiments of indicia of the present disclosure will now be described with respect to FIGS. 26-27. FIGS. 26-27 illustrate various brackets and indicia of the present disclosure, wherein like numerals represent like elements. The indicia of FIGS. 26-27 share many of the same elements, features, and functions as the indicia 108 described above with respect to FIGS. 1-4. Reference is made to the description above accompanying FIGS. 1-4 for a more complete description of the features and elements (and alternatives to such features and elements) of the embodiments illustrated in FIGS. 26-27. Any of the features described above with respect to FIGS. 1-4 can be applied to the embodiments of FIGS. 26-27, and vice versa.

FIG. 26 illustrates a bracket 1302 according to another embodiment of the present disclosure. The bracket 1302 includes indicia 1308. The bracket 1302 and the indicia 1308 are substantially the same as the bracket 102 and the indicia 108 of the embodiment of FIGS. 1-6, except that the indicia 108 is coupled to (or provided on) a second major surface 1314 of a base 1310 of the bracket 1302, rather than being coupled to a first major surface 1312. As such, the remainder of the base 1310 of FIG. 26 is transparent, such that the indicia 1308 can be easily seen through the base 1310 when the base 1310 is viewed from above (i.e., looking downwardly at the first major surface 1312). Specifically, the indicia 1308 is illustrated as being printed on the second major surface 1314 of the base 1310; however, in some embodiments, the indicia 1308 can be co-molded (e.g., co-injection molded) with the base 1310, such that the indicia 1308 forms a portion of the second major surface 1314 of the base 1310.

The bracket 1302 is shown by way of example only, but it should be understood that the indicia 1308 of FIG. 26 can be used in conjunction with any bracket of the present disclosure.

FIG. 27 illustrates a bracket 1402 according to another embodiment of the present disclosure. The bracket 1402 includes indicia 1408. The bracket 1402 is substantially the same as the bracket 202 of FIGS. 7-9, and the indicia 1408 is substantially the same as the indicia 208 shown in FIG. 9, except that the indicia 1408 in FIG. 27 is embossed into a first major surface 1412 of a base 1410 of the bracket 1402. As such, the indicia 1408 forms a depressed region or area in the first major surface 1412 that can be detected tactilely as well as visually.

The bracket 1402 is substantially the same as that of FIGS. 7-9 by way of example only, but it should be understood that the embossed indicia 1408 can be used in conjunction with any bracket of the present disclosure.

Methods of Coupling a Medical Article to a Medical Article Securement System

FIGS. 28A-30C illustrate methods of coupling various medical articles to the bracket 102 and medical article securement system 100 of FIGS. 1-6. Different coupling methods can be used for different systems and brackets of the present disclosure, and the methods illustrated in FIGS. 28A-30C are included merely for illustration purposes.

Figure 28A:
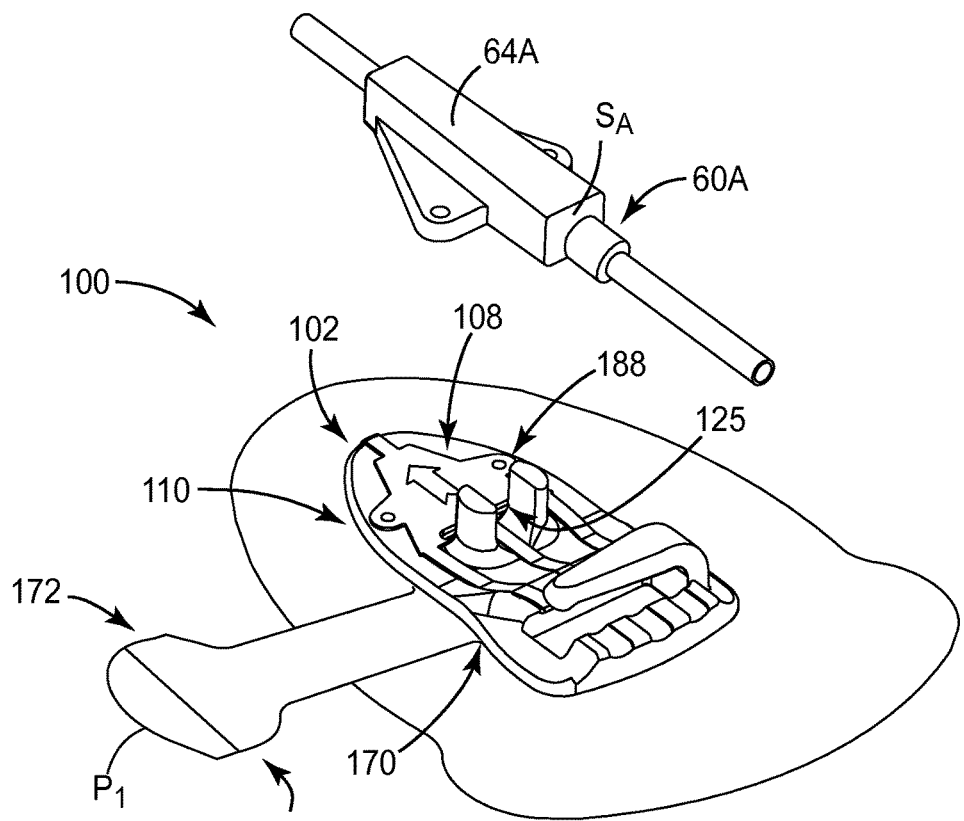
FIGS. 28A-28C illustrate a method of coupling a first type of a medical article to the medical article securement system of FIGS. 1-6.
Figure 28B:
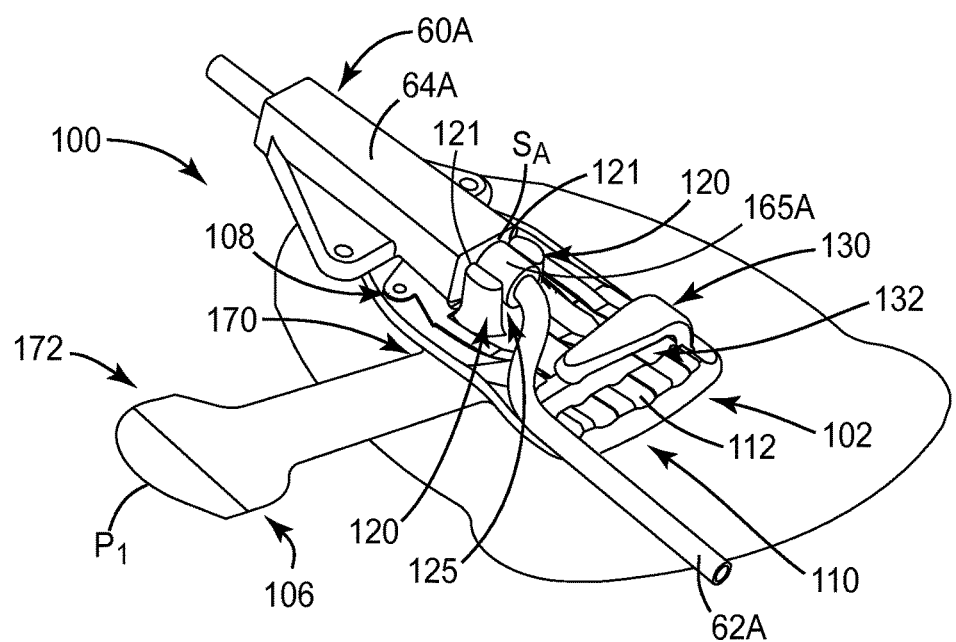
Figure 28C:
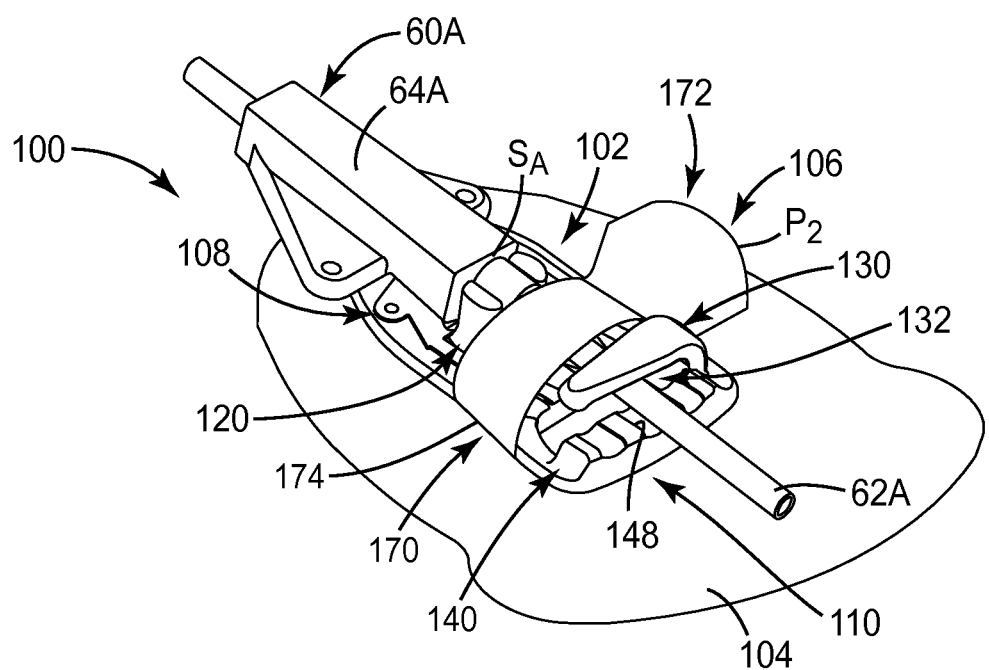
Figure 29A:
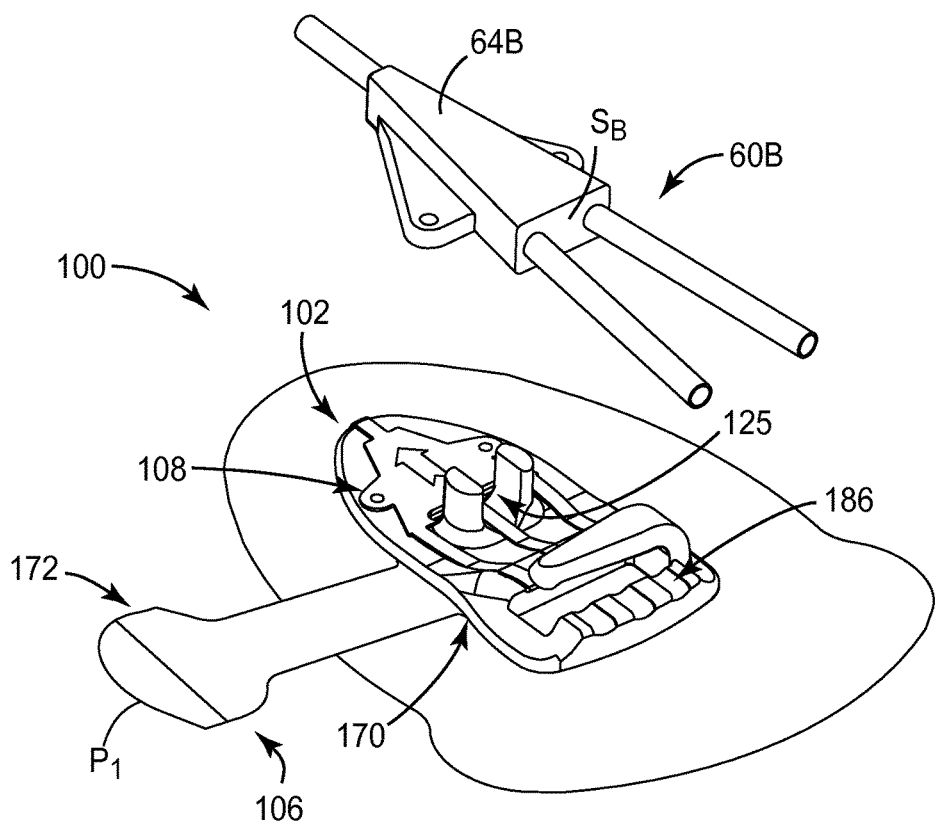
FIGS. 29A-29C illustrate a method of coupling a second type of a medical article to the medical article securement system of FIGS. 1-6.
Figure 29B:
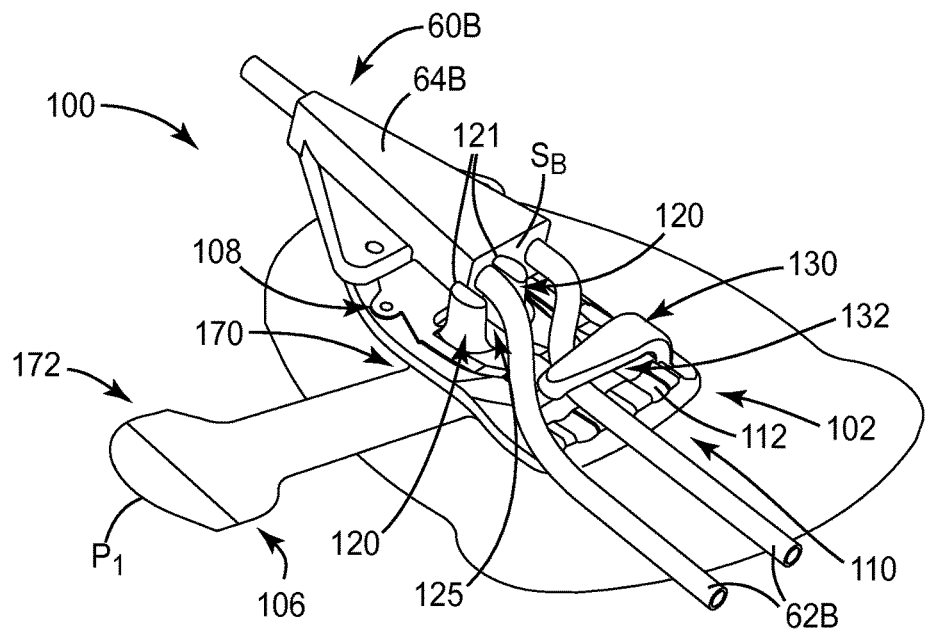
Figure 29C:
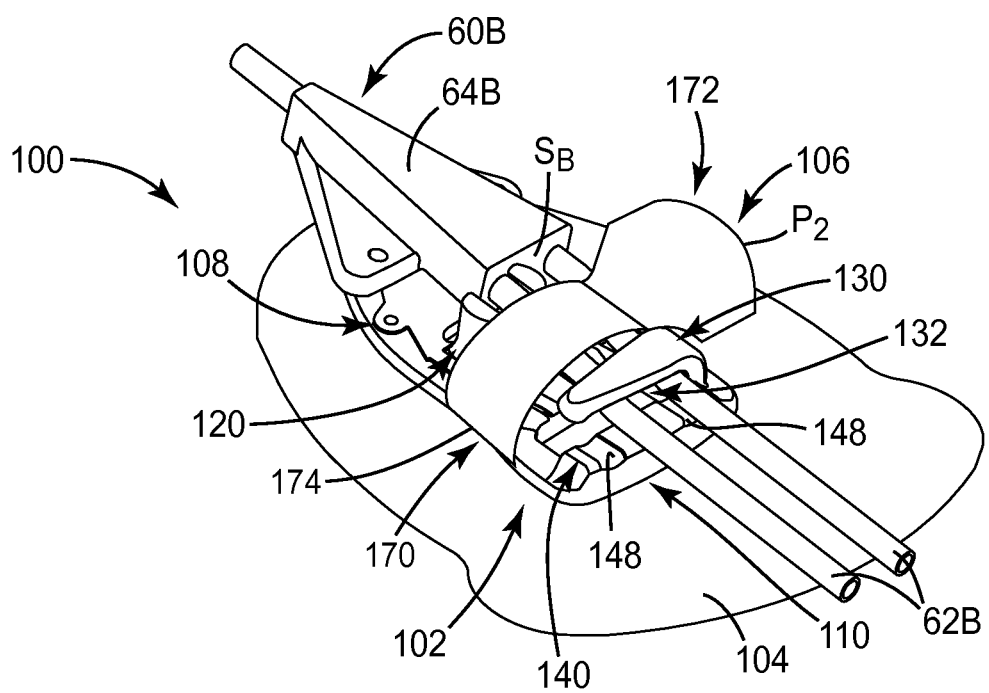
Figure 30A:
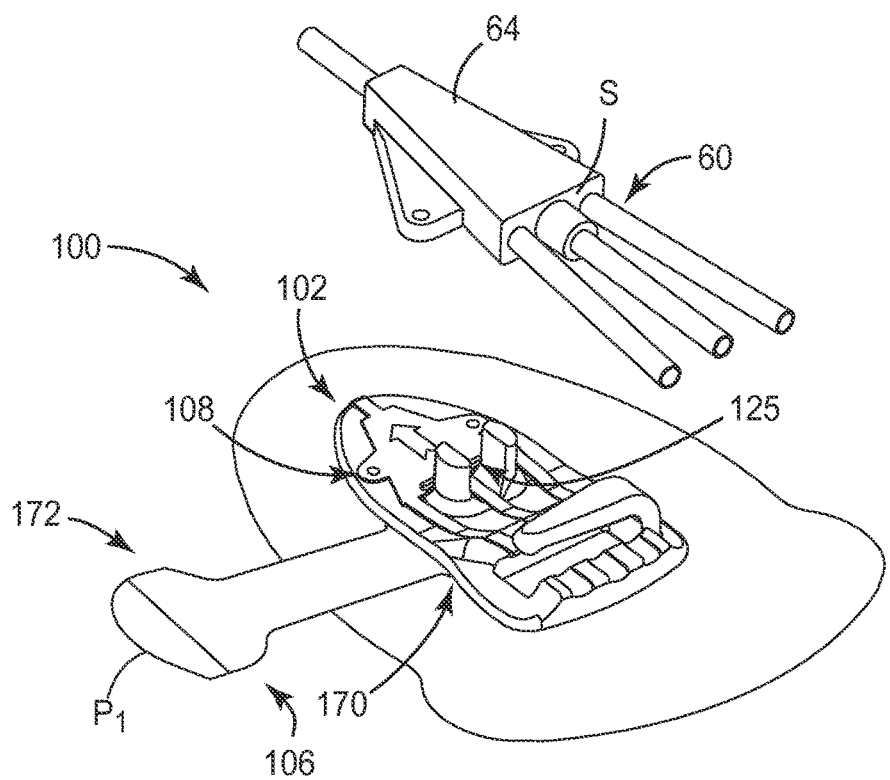
FIGS. 30A-30C illustrate a method of coupling a third type of a medical article to the medical article securement system of FIGS. 1-6.
Figure 30B:
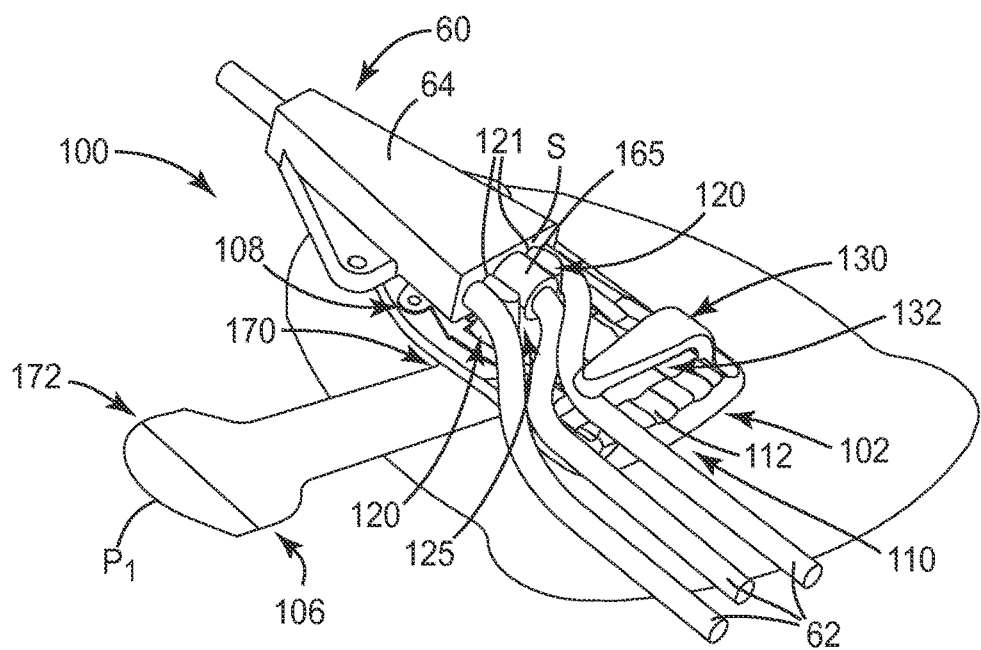
Figure 30C:
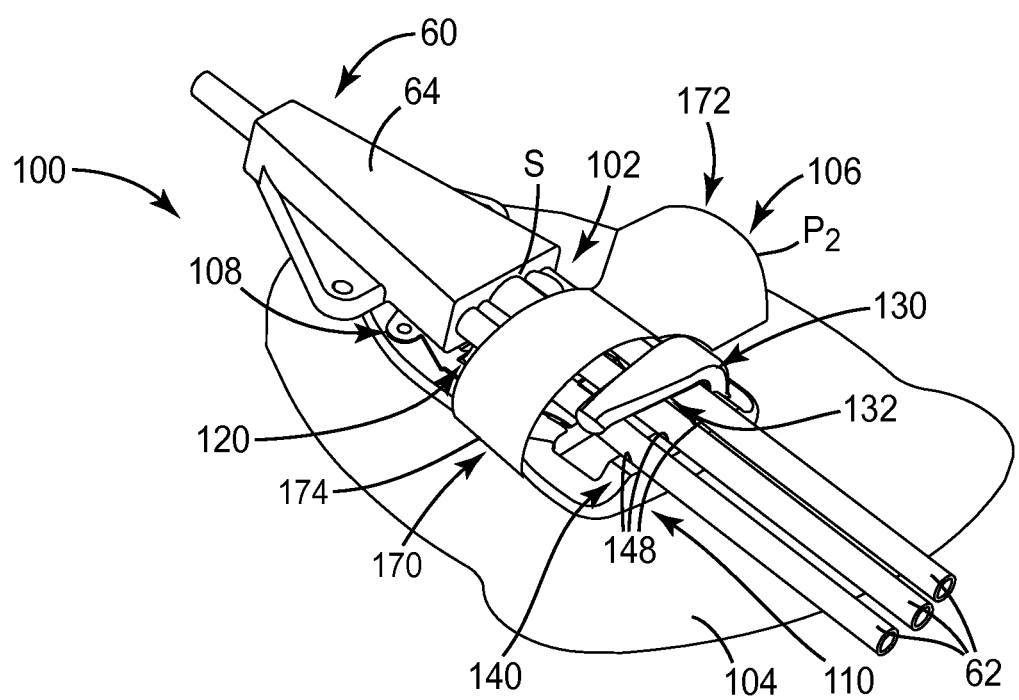

FIGS. 28A-28C illustrate a method of coupling a single-input catheter system 60A to the bracket 102 and system 100; FIGS. 29A-29C illustrate a method of coupling a double-input catheter system 60B to the bracket 102 and system 100; and FIGS. 30A-30C illustrate a method of coupling a triple-input catheter system, i.e., the medical article 60 of FIG. 1, to the bracket 102 and system 100. As a result, FIGS. 28A-30C illustrate how the same system 100 can be used to retain different medical articles.

The methods illustrated in FIGS. 28A-30C specifically illustrate coupling a medical article to the bracket 102, e.g., using the indicia 108 and the flap 106. It should be assumed that the base dressing 104 has already been applied to a patient's skin prior to the methods illustrated in FIGS. 28A-30C.

As shown in 28A, the single-input catheter system 60A can be coupled to the system 100 by first orienting the medical article 60A with respect to the bracket 102 as indicated by the indicia 108, such that the portions of the medical article 60A line up over their respective representations in the indicia 108. As shown in FIG. 28B, the method can then include positioning the medical article 60A down onto the first major surface 112 of the base 110 and aligning an external surface $S_A$ (e.g., of a catheter hub 64A) with the distal ends 121 of the posts 120, such that the surface $S_A$ abuts the distal ends 121 of the posts 120, and such that at least a portion of the medical article 60A (e.g., the single input catheter 62A and/or an extension 165A of the catheter hub 64A) is passed through the second channel 125 between the posts 120. Abutting the external surface $S_A$ against the posts 120 can be performed as the medical article 60A is set atop the first major surface 112 of the base 110, or the medical article 60A can be positioned on the first major surface 112, and then the medical article 60A can be pulled proximally until the external surface $S_A$ abuts the posts 120. As shown in FIGS. 28B and 28C, the method can further include sliding the single input catheter 62A under the arm 130 and into the channel 132.

As shown in FIG. 28A, by way of example only, the portion (i.e., the second portion 188) of the indicia 108 representing a catheter hub is located on the first major surface 112 of the base 110 directly adjacent the distal ends 121 of the posts 120 to show users that the catheter hub (e.g., the catheter hub 64A) of the medical article being coupled to the bracket 102 should be directly abutted against the distal ends 121 of the posts 120.

As shown in FIG. 28C, the method can further include positioning the input catheter 62A into one of the grooves 148 formed in the land 140 on the base 110. As further shown in FIG. 28C, the method can further include moving the free end 172 of the flap 106 about the hinge 174 from the first position $P_1$ (shown in FIGS. 28A and 28B) to the second positioned $P_2$ (shown in FIG. 28C) where the flap 106 is positioned over the medical article 60A, and coupling securing means on the flap 106 to the base dressing 104 (and/or the bracket 102). As a result of the posts 120, the arm 130, and the flap 106, the medical article 60A is inhibited from movement in the lateral, longitudinal and vertical directions (e.g., relative to the bracket 102) when coupled to the system 100 as shown in FIG. 28C.

As shown in 29A, the double-input catheter system 60B can be coupled to the system 100 by first orienting the medical article 60B with respect to the bracket 102 as indicated by the indicia 108, such that the portions of the medical article 60B line up over their respective representations in the indicia 108. As shown in FIG. 29B, the method can then include positioning the medical article 60B down onto the first major surface 112 of the base 110 and aligning an external surface $S_B$ (e.g., of a catheter hub 64B) with the distal ends 121 of the posts 120, such that the surface $S_B$ abuts the distal ends 121 of the posts 120, and such that at least a portion of the medical article 60B (e.g., at least one of the two input catheters 62B and/or an extension (not shown) of the catheter hub 64B) is passed through the second channel 125 between the posts 120. Abutting the external surface $S_B$ against the posts 120 can be performed as the medical article 60B is set atop the first major surface 112 of the base 110, or the medical article 60B can be positioned on the first major surface 112, and then the medical article 60B can be pulled proximally until the external surface $S_B$ abuts the posts 120. As shown in FIGS. 29B and 29C, the method can further include sliding the input catheters 62B under the arm 130 and into the channel 132. As shown in FIG. 29C, the method can further include positioning each of the input catheters 62B into one of the grooves 148 formed in the land 140 on the base 110. By way of example only, a portion (e.g., the first portion 186—see FIG. 29A) of the indicia 108 is shown as passing under the arm 130 and being provided in the grooves 148 to provide a visual cue to users that the input catheters 62A should be passed under the arm 130 and positioned in the channel 132, and should be further positioned in the grooves 148.

As further shown in FIG. 29C, the method can further include moving the free end 172 of the flap 106 about the hinge 174 from the first position $P_1$ (shown in FIGS. 29A and 29B) to the second positioned $P_2$ (shown in FIG. 29C) where the flap 106 is positioned over the medical article 60B, and coupling securing means on the flap 106 to the base dressing 104 (and/or the bracket 102). As a result of the posts 120, the arm 130, and the flap 106, the medical article 60B is inhibited from movement in the lateral, longitudinal and vertical directions (e.g., relative to the bracket 102) when coupled to the system 100 as shown in FIG. 29C.

As shown in FIG. 30A, the triple-input catheter system 60 can be coupled to the system 100 by first orienting the medical article 60 with respect to the bracket 102 as indicated by the indicia 108, such that the portions of the medical article 60 line up over their respective representations in the indicia 108. As shown in FIG. 30B, the method can then include positioning the medical article 60 down onto the first major surface 112 of the base 110 and aligning an external surface S (e.g., of a catheter hub 64) with the distal ends 121 of the posts 120, such that the surface S abuts the distal ends 121 of the posts 120, and such that at least a portion of the medical article 60 (e.g., at least one of the three input catheters 62, such as the middle input catheter 62, and/or the extension 165 of the catheter hub 64, if employed) is passed through the second channel 125 between the posts 120. Abutting the external surface S against the posts 120 can be performed as the medical article 60 is set atop the first major surface 112 of the base 110, or the medical article 60 can be positioned on the first major surface 112, and then the medical article 60 can be pulled proximally until the external surface S abuts the posts 120. As shown in FIGS. 30B and 30C, the method can further include sliding the input catheters 62 under the arm 130 and into the channel 132. As shown in FIG. 30C, the method can further include positioning each of the input catheters 62 into one of the grooves 148 formed in the land 140 on the base 110. As further shown in FIG. 30C, the method can further include moving the free end 172 of the flap 106 about the hinge 174 from the first position $P_1$ (shown in FIGS. 30A and 30B) to the second positioned $P_2$ (shown in FIG. 30C) where the flap 106 is positioned over the medical article 60, and coupling securing means on the flap 106 to the base dressing 104 (and/or the bracket 102). As a result of the posts 120, the arm 130, and the flap 106, the medical article 60 is inhibited from movement in the lateral, longitudinal and vertical directions (e.g., relative to the bracket 102) when coupled to the system 100 as shown in FIG. 30C.

In embodiments in which the bracket includes more than one arm 130, the above methods can be modified by moving the input catheters 62A, 62B, 62 under each of the plurality of arms 130, e.g., sequentially. In addition, in embodiments that do not employ one or more of posts 120, arms 130, a flap 106 and/or indicia 108, the above methods can be modified to eliminate the steps relating to the omitted element. Furthermore, in embodiments employing more than one flap 106, the free end of each flap 106 can simply be moved from its respective first position to its respective second position (e.g., sequentially) to further secure the medical article 60A, 60B, 60 to the system 100.

Each embodiment shown in the figures is illustrated as a separate embodiment for clarity in illustrating a variety of features of the applicators of the present disclosure. However, it should be understood that any combination of elements and features of any of the embodiments illustrated in the figures and described herein can be employed in the applicators of the present disclosure.

The following embodiments are intended to be illustrative of the present disclosure and not limiting.

EMBODIMENTS

1. A bracket configured for use with a medical article, the bracket comprising:
    a base having a longitudinal axis and a first major surface;
    a post coupled to the base and extending upwardly from the base in a direction generally normal to the first major surface of the base, the post configured to abut an external surface of the medical article to inhibit at least longitudinal movement of the medical article when the medical article is coupled to the bracket; and
    an arm coupled to the base and extending generally parallel to the first major surface of the base, the arm spaced a distance from the first major surface of the base to define a channel under the arm, the channel dimensioned to receive at least a portion of the medical article, the arm including a fixed end and a free end such that the arm is cantilevered, the arm configured to inhibit movement of the medical article in at least a direction that is generally normal to the first major surface of the base when the medical article is coupled to the bracket,
    wherein the post and the arm are each fixed with respect to the base.

2. A method for coupling a medical article to a medical article securement system, the method comprising:
providing a medical article;
providing a medical article securement system comprising a bracket wherein the bracket comprises:
a base having a longitudinal axis and a first major surface,
a post extending upwardly from the base in a direction generally normal to the first major surface of the base, and
an arm extending generally parallel to the first major surface of the base, the arm spaced a distance from the first major surface of the base to define a channel under the arm, the channel dimensioned to receive at least a portion of the medical article, the arm including a fixed end and a free end such that the arm is cantilevered;
abutting an external surface of the medical article against the post; and
moving a portion of the medical article into the channel defined by the arm by positioning the portion of the medical article adjacent the free end of the arm, and sliding the portion of the medical article under the arm, into the channel.

3. The method of embodiment 2, wherein moving a portion of the medical article into the channel defined by the arm occurs substantially simultaneously with abutting an external surface of the medical article against the post.

4. The method of embodiment 2 or 3, wherein the channel is a first channel, wherein the post is one of a plurality of posts spaced a lateral distance apart to define a second channel therebetween, and further comprising positioning a portion of the medical article in the second channel.

5. The method of embodiment 4, wherein positioning a portion of the medical article in the second channel occurs substantially simultaneously with abutting an external surface of the medical article against the post.

6. The system of embodiment 1 or the method of any of embodiments 2-5, wherein the post is free of radially-extending projections.

7. The bracket of embodiment 1 or 6 or the method of any of embodiments 2-6, wherein the longitudinal axis of the base defines a longitudinal direction, and wherein the post is longer in the longitudinal direction at its upper end than at its lower end adjacent the base, such that a distal end of the post is tapered toward the base.

8. The bracket of any of embodiments 1, 6 and 7 or the method of any of embodiments 2-7, wherein a distal end of the post is configured to abut the external surface of the medical article.

9. The bracket of any of embodiments 1 and 6-8 or the method of any of embodiments 2-8, wherein the fixed end of the arm is located no further distally than a distal end of the post.

10. The bracket of any of embodiments 1 and 6-9 or the method of any of embodiments 2-9, wherein the arm is located proximally relative to the post.

11. The bracket of any of embodiments 1 and 6-10 or the method of any of embodiments 2-10, wherein the post provides a pedestal for the cantilevered arm.

12. The bracket of any of embodiments 1 and 6-11 or the method of any of embodiments 2-11, wherein the arm extends generally parallel with respect to the longitudinal axis of the base.

13. The bracket of any of embodiments 1 and 6-11 or the method of any of embodiments 2-11, wherein the arm extends generally laterally with respect to the longitudinal axis of the base.

14. The bracket of any of embodiments 1 and 6-11 or the method of any of embodiments 2-11, wherein the arm extends generally laterally with respect to the longitudinal axis of the base and has a lateral width that extends from its fixed end to its free end, and wherein the post is located within a width on the base that is defined by the lateral width of the arm.

15. The bracket of any of embodiments 1 and 6-14 or the method of any of embodiments 2-14, wherein the arm is located toward a distal end of the base.

16. The bracket of any of embodiments 1 and 6-15 or the method of any of embodiments 2-15, wherein the post and the arm are each directly coupled to the base.

17. The bracket of any of embodiments 1 and 6-16 or the method of any of embodiments 2-16, wherein the base, the post, and the arm are integrally formed.

18. The bracket of any of embodiments 1 and 6-17 or the method of any of embodiments 2-17, wherein the post is one of a plurality of posts, and wherein the plurality of posts are fixed with respect to the base.

19. The bracket of any of embodiments 1 and 6-18 or the method of any of embodiments 2-18, wherein the post is one of a plurality of posts, and wherein the plurality of posts together are configured to abut an external surface of the medical article to inhibit at least longitudinal movement of the medical article when the medical article is coupled to the bracket.

20. The bracket of any of embodiments 1 and 6-19 or the method of any of embodiments 2-19, wherein the medical article has a longitudinal axis that is oriented generally parallel to the longitudinal axis of the base when the medical article is coupled to the bracket.

21. The bracket of any of embodiments 1 and 6-20 or the method of any of embodiments 2-20, wherein the medical article includes a catheter system comprising a catheter hub and a catheter, and wherein the channel defined by the arm is dimensioned to receive the catheter.

22. The bracket or method of embodiment 21, wherein the post is configured to abut a proximal end of the catheter hub.

23. The bracket or method of embodiment 21 or 22, wherein the channel is a first channel, wherein the post is one of a plurality of posts, wherein each of the plurality of posts is separated a lateral distance from an adjacent post to define a second channel therebetween, wherein the second channel is oriented generally parallel to the longitudinal axis and is dimensioned to receive the catheter.

24. The bracket or method of any of embodiments 21-23, wherein the second channel is upwardly-opening.

25. The bracket or method of any of embodiments 21-24, wherein each post includes a distal end, and wherein the distal ends of the plurality of posts together define a longitudinal stop for the catheter hub to inhibit proximal movement of the catheter hub when the catheter system is coupled to the bracket.

26. The bracket of any of embodiments 1 and 6-25 or the method of any of embodiments 2-25, wherein the arm and the post are spaced a longitudinal distance apart.

27. The bracket of any of embodiments 1 and 6-26 or the method of any of embodiments 2-26, wherein the post further inhibits lateral movement of the medical article when the medical article is coupled to the bracket.

28. The bracket of any of embodiments 1 and 6-27 or the method of any of embodiments 2-27, wherein the channel is a first channel, wherein the post is one of a plurality of posts, and wherein each of the plurality of posts is separated a lateral distance from an adjacent post to define a second channel therebetween, the second channel oriented generally parallel to the longitudinal axis and dimensioned to receive at least a portion of the medical article.

29. The bracket or method of embodiment 28, wherein the first channel and the second channel are generally aligned.

30. The bracket or method of embodiment 28 or 29, wherein the plurality of posts includes two posts that are centered about a lateral width of the base.

31. The bracket or method of any of embodiments 28-30, wherein the plurality of posts further inhibit lateral movement of the medical article when the medical article is coupled to the bracket.

32. The bracket or method of any of embodiments 28-31, wherein the plurality of posts and the arm are arranged such that at least a portion of the medical article extends through the first channel and the second channel when the medical article is coupled to the bracket.

33. The bracket or method of any of embodiments 28-32, wherein the second channel is upwardly-opening.

34. The bracket or method of any of embodiments 28-33, wherein the second channel has a closed bottom end adjacent the first major surface of the base and an open upper end.

35. The bracket of any of embodiments 1 and 6-34 or the method of any of embodiments 2-34, wherein the post is configured such that at least a portion of the medical article is located laterally and longitudinally adjacent the post when the medical article is coupled to the bracket.

36. The bracket of any of embodiments 1 and 6-35 or the method of any of embodiments 2-35, wherein the arm and the post are arranged such that the medical article is generally centered with respect to a lateral width of the base when the medical article is coupled to the bracket.

37. The bracket of any of embodiments 1 and 6-36 or the method of any of embodiments 2-36, wherein the arm and the post are arranged such that at least a portion of the medical article extends adjacent the post and through the channel defined by the arm when the medical article is coupled to the bracket.

38. A bracket configured for use with a medical article having a proximal end, a distal end, and a longitudinal axis extending from the proximal end to the distal end, the bracket comprising:
 a base having a first major surface, a proximal end, a distal end, and a longitudinal axis extending from the proximal end to the distal end, wherein the longitudinal axis of the base is oriented generally parallel to the longitudinal axis of the medical article of the base when the medical article is coupled to the bracket;
 an arm coupled to the base and extending generally parallel to the first major surface of the base, the arm spaced a distance from the first major surface of the base to define a first channel under the arm, the first channel generally oriented generally parallel to the longitudinal axis of the base and dimensioned to receive at least a portion of the medical article, the arm including a fixed end and a free end such that the arm is cantilevered, the arm configured to inhibit movement of the medical article in at least a direction that is generally normal to the first major surface of the base when the medical article is coupled to the bracket; and
 a plurality of posts coupled to the base and extending upwardly from the base in a direction generally normal to the first major surface of the base, the plurality of posts together configured to abut an external surface on the medical article to inhibit at least longitudinal movement of the medical article when the medical article is coupled to the bracket, each of the plurality of posts being separated a lateral distance from an adjacent post to define a second channel therebetween, the second channel oriented generally along the longitudinal axis and dimensioned to receive at least a portion of the medical article.

39. The bracket of embodiment 38, wherein the arm and the plurality of posts and are fixed with respect to the base.

40. The bracket of embodiment 38 or 39, wherein at least one of the plurality of posts provides a pedestal for the cantilevered arm.

41. The bracket of any of embodiments 38-40, wherein the arm extends generally laterally with respect to the longitudinal axis of the base.

42. The bracket of embodiment 41, wherein the arm has a lateral width that extends from its fixed end to its free end, and wherein the plurality of posts are located within a width on the base that is defined by the lateral width of the arm.

43. The bracket of any of embodiments 38-42, wherein the arm is separated a longitudinal distance from the plurality of posts.

44. The bracket of any of embodiments 38-43, wherein the first channel and the second channel are generally aligned.

45. The bracket of any of embodiments 38-44, wherein the plurality of posts further inhibit lateral movement of the medical article when the medical article is coupled to the bracket.

46. The bracket of any of embodiments 38-45, wherein the plurality of posts includes two posts that are centered about a lateral width of the base.

47. The bracket of any of embodiments 38-46, wherein the plurality of posts further inhibit lateral movement of the medical article when the medical article is coupled to the bracket.

48. The bracket of any of embodiments 38-47, wherein the plurality of posts and the arm are arranged such that at least a portion of the medical article extends through the first channel and the second channel when the medical article is coupled to the bracket.

49. The bracket of any of embodiments 38-48, wherein the second channel has a closed bottom end adjacent the first major surface of the base and an open upper end.

50. The bracket of any of embodiments 38-49, wherein each of the plurality of posts is configured such that at least a portion of the medical article is located laterally and longitudinally adjacent the post when the medical article is coupled to the bracket.

51. The bracket of any of embodiments 38-50, wherein the arm and the plurality of posts are arranged such that the medical article is generally centered about the longitudinal axis of the base when the medical article is coupled to the bracket.

52. The bracket of any of embodiments 38-51, wherein the arm and the plurality of posts are arranged such that at least a portion of the medical article extends between adjacent posts and through the channel defined by the arm when the medical article is coupled to the bracket.

53. The bracket of any of embodiments 1 and 6-52 or the method of any of embodiments 2-37, wherein the base includes a land located adjacent the arm, such that at least a portion of the medical article can be threaded over the land and under the arm when the medical article is coupled to the bracket.

54. The bracket or method of embodiment 53, wherein at least a portion of the land is formed of a first material that is different than a remainder of the base.

55. The bracket or method of embodiment 54, wherein the first material is a friction control material.

56. The bracket or method of any of embodiments 53-55, wherein the arm and the land together inhibit vertical movement of the medical article.

57. The bracket or method of any of embodiments 53-56, wherein the arm is located between a first longitudinal end of the land and a second longitudinal end of the land.

58. The bracket or method of any of embodiments 53-57, wherein the land includes a first portion and a second portion, and wherein the arm is located between the first portion and the second portion of the land.

59. The bracket or method of embodiment 58, wherein the first portion and the second portion of the land define a recess therebetween that is located under the arm.

60. The bracket or method of embodiment 58 or 59, wherein at least one of the first portion and the second portion of the land includes an upper surface comprising at least one of a groove and a ridge.

61. The bracket or method of any of embodiments 53-60, wherein the first portion of the land has a first height, and wherein the second portion of the land has a second height different from the first height.

62. The bracket or method of any of embodiments 53-61, wherein the land includes an upper surface comprising at least one of a groove and a ridge.

63. The bracket of any of embodiments 1 and 6-62 or the method of any of embodiments 2-3 and 53-62, wherein the arm further inhibits lateral movement of the medical article when the medical article is coupled to the bracket.

64. The bracket of any of embodiments 1 and 6-63 or the method of any of embodiments 2-37 and 53-63, wherein the arm includes a pedestal that defines a vertical component of the arm and a horizontal projection that is cantilevered from the pedestal and defines a horizontal component of the arm, such that the projection is spaced a vertical distance from the first major surface of the base by the pedestal.

65. The bracket or method of embodiment 64, wherein the pedestal and the projection are oriented substantially perpendicularly with respect to one another.

66. The bracket or method of embodiment 64 or 65, wherein the pedestal provides a lateral stop to inhibit lateral movement of the medical article.

67. The bracket of any of embodiments 1 and 6-66 or the method of any of embodiments 2-37 and 53-66, wherein the arm is oriented substantially perpendicularly with respect to the longitudinal axis of the base.

68. The bracket of any of embodiments 1 and 6-67 or the method of any of embodiments 2-37 and 53-67, wherein the arm is one of a plurality of arms.

69. The bracket or method of embodiment 68, wherein each of the plurality of arms is separated a longitudinal distance from an adjacent arm.

70. The bracket or method of embodiment 68 or 69, wherein a first arm has its fixed end on a first lateral side of the base, and wherein a second arm has its fixed end on a second lateral side opposite the first lateral side, such that the first arm and the second arm oppose one another.

71. The bracket or method of any of embodiments 68-70, wherein the first arm and the second arm together inhibit lateral movement of the medical article.

72. The bracket of any of embodiments 1 and 6-71 or the method of any of embodiments 2-37 and 53-71, wherein the base includes an opening formed therethrough.

73. The bracket or method of embodiment 72, wherein the opening is located in overlapping relationship with the arm.

74. The bracket of any of embodiments 1 and 6-73 or the method of any of embodiments 2-37 and 53-73, wherein the base includes a plurality of perforations formed therethrough.

75. The bracket of any of embodiments 1 and 6-74 or the method of any of embodiments 2-37 and 53-74, wherein the first major surface of the base includes at least one of a groove and a ridge.

76. The bracket of any of embodiments 1 and 6-75 or the method of any of embodiments 2-37 and 53-75, wherein the first major surface of the base is configured to accommodate at least a portion of the medical article.

77. The bracket of any of embodiments 1 and 6-76 or the method of any of embodiments 2-37 and 53-76, wherein the first major surface of the base includes a complimentary shape to at least a portion of the medical article.

78. The bracket of any of embodiments 1 and 6-77 or the method of any of embodiments 2-37 and 53-77, wherein the base includes at least one groove formed in the first major surface to accommodate at least a portion of the medical article.

79. The bracket of any of embodiments 1 and 6-78 or the method of any of embodiments 2-37 and 53-78, wherein the bracket includes a first portion where the first major surface of the base is located at a first height and a second portion where the first major surface is located at a second height.

80. The bracket or method of embodiment 79, wherein the first major surface of the base has a varying height between the first portion and the second portion.

81. The bracket or method of embodiment 79, wherein the first major surface includes a step between the first portion and the second portion.

82. The bracket or method of embodiment 79 or 80, wherein the first major surface is ramped between the first portion and the second portion.

83. The bracket or method of any of embodiments 80-82, wherein the first height is greater than the second height 84. The bracket or method of any of embodiments 80-83, wherein the first portion includes the arm and a land located adjacent the arm.

85. The bracket of any of embodiments 1 and 6-84 or the method of any of embodiments 2-37 and 53-84, wherein the arm includes a retaining feature located adjacent its free end.
86. The bracket of any of embodiments 1 and 6-85 or the method of any of embodiments 2-37 and 53-85, wherein the base has a first longitudinal end, a second longitudinal end, and a length between the first longitudinal end and the second longitudinal end, and wherein the length is at least about 19 mm.
87. A medical article securement system comprising the bracket of any of embodiment 1 and 6-86, wherein the bracket is coupled to a base dressing having a first side and a second side opposite the first side, the second side comprising a skin-contact adhesive, wherein the base includes a second major surface opposite the first major surface, and wherein the second major surface of the base is coupled to the first side of the base dressing.
88. A medical article securement system comprising:
the bracket of any of embodiments 1 and 6-86; and
a flap including
a fixed end, and
a free end that is movable with respect to the bracket between a first position in which the flap is not positioned over the bracket, and a second position in which at least a portion of the flap is positioned over the bracket to further inhibit movement of the medical article relative to the bracket when the medical article is coupled to the system, wherein the fixed end of the flap is coupled to the bracket.
89. The system of embodiment 88, wherein the flap is configured to inhibit at least vertical movement of the medical article when the medical article is coupled to the system.
90. The system of embodiment 88 or 89, wherein the flap is further configured to inhibit lateral movement of the medical article when the medical article is coupled to the system.
91. The system of any of embodiments 88-90, wherein the flap is formed of at least one of a fabric, a woven fibrous web, a nonwoven fibrous web, a knit, a polymeric film, an elastomer, a combination thereof, or a laminate structure comprising any of the above.
92. The system of any of embodiments 88-91, wherein the flap is one of a plurality of flaps, and wherein the plurality of flaps together inhibit at least vertical movement of the medical article.
93. The system of embodiment 92, wherein each of the plurality of flaps is separated a longitudinal distance from an adjacent flap.
94. The system of embodiment 92 or 93, wherein at least two of the plurality of flaps overlap or cross one another.
95. The system of any of embodiments 88-94, wherein the flap includes a hinge about which the free end of the flap can pivot to move between the first position and the second position.
96. The system of any of embodiments 88-95, wherein the hinge is located adjacent an edge of the bracket.
97. The system of any of embodiments 88-96, wherein the flap is positioned in an overlapping relationship with the bracket when the free end of the flap is in the second position.
98. The system of any of embodiments 88-97, further comprising a base dressing having a first side and a second side opposite the first side, the second side comprising a skin-contact adhesive, wherein the bracket and the flap are coupled to the first side of the base dressing.
99. The system of embodiment 98, wherein the fixed end of the flap is coupled between the base dressing and the bracket.
100. The system of embodiment 98 or 99, wherein the fixed end of the flap is provided by the base dressing.
101. The system of any of embodiments 88-100, wherein at least the free end of the flap includes securing means.
102. The system of any of embodiments 88-101, wherein the flap includes a first side and a second side opposite the first side, wherein the first side is configured to face the medical article such that the first side of the free end of the flap faces the medical article when the free end of the flap is in the second position, wherein the second side is configured to face away from the bracket when the free end of the flap is in the second position, and wherein at least a portion of the first side of the flap includes securing means.
103. The system of embodiment 102, wherein the second side of the fixed end of the flap is coupled to the first major surface of the base of the bracket.
104. The system of any of embodiments 101-103, wherein the securing means includes at least one of an adhesive, a hook and loop fastener, or a combination thereof.
105. The system of any of embodiments 88-104, wherein the flap is dimensioned to be longer than the bracket in a direction in which the flap extends across the bracket when the free end of the flap is in the second position.
106. The system of any of embodiments 88-105, wherein the bracket includes a lateral width, wherein the flap is positioned to extend across the lateral width of the bracket when the free end of the flap is in the second position, and wherein the flap has a length that is greater than the lateral width of the bracket.
107. The bracket of any of embodiments 1 and 6-86, the method of any of embodiments 2-86, or the system of any of embodiments 88-106, further comprising indicia comprising a representation of a medical article, such that the indicia mimics the appearance of the medical article and provides a visual cue for coupling the medical article to the medical article securement system.
108. The bracket, method or system of embodiment 107, wherein the indicia defines an orientation of the medical article with respect to the bracket.
109. The bracket, method or system of embodiment 107 or 108, wherein the indicia is integrally formed with the bracket.
110. The bracket, method or system of embodiment 109, wherein the base of the bracket and the indicia are co-molded together, and wherein the indicia has at least one optical property that is different than a remainder of the base.
111. The bracket, method or system of embodiment 110, wherein the base and the indicia are co-injection molded.
112. The bracket, method or system of any of embodiments 107-111, wherein the medical article includes a catheter system comprising a catheter hub and a catheter, and wherein the indicia includes a representation of a catheter hub and a catheter.
113. The bracket, method or system of any of embodiments 107-112, wherein the indicia includes a pictorial representation of the medical article.

114. The bracket, method or system of any of embodiments 107-113, wherein the indicia includes a two-dimensional representation of the medical article.

115. The bracket, method or system of any of embodiments 107-114, wherein the indicia includes a representation of the outer contours of the medical article.

116. The bracket, method or system of any of embodiments 107-115, wherein the indicia includes a representation of the outer periphery of the medical article.

117. The bracket, method or system of any of embodiments 107-116, wherein the indicia is sized similarly to the medical article.

118. The bracket, method or system of any of embodiments 107-117, wherein the indicia includes printed graphics.

119. The bracket, method or system of any of embodiments 107-118, wherein the indicia includes an embossed surface.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A bracket configured for use with a medical article, the bracket comprising:
a base having a longitudinal axis and a first major surface;
a post coupled to the base and extending upwardly from the base in a direction generally normal to the first major surface of the base, the post configured to abut an external surface of the medical article without being passed through the medical article to inhibit at least longitudinal movement of the medical article when the medical article is coupled to the bracket; and
an arm coupled to the base and extending generally parallel to the first major surface of the base, the arm spaced a distance from the first major surface of the base to define a channel under the arm, the channel dimensioned to receive at least a portion of the medical article, the arm including a fixed end and a free end such that the arm is cantilevered, the arm configured to inhibit movement of the medical article in at least a direction that is generally normal to the first major surface of the base when the medical article is coupled to the bracket,
wherein the post and the arm are each fixed with respect to the base, wherein the arm defines a lateral width W that extends from the fixed end of the arm to the free end of the arm, and wherein the post is located within the lateral width W of the arm on the base.

2. The bracket of claim 1, wherein the post is free of radially-extending projections.

3. The bracket of claim 1, wherein the longitudinal axis of the base defines a longitudinal direction, and wherein the post is longer in the longitudinal direction at its upper end than at its lower end adjacent the base, such that a distal end of the post is tapered toward the base.

4. The bracket of claim 1, wherein a distal end of the post is configured to abut the external surface of the medical article.

5. The bracket of claim 1, wherein the fixed end of the arm is located no further distally than a distal end of the post.

6. The bracket of claim 1, wherein the arm is located proximally relative to the post.

7. The bracket of claim 1, wherein the post provides a pedestal for the cantilevered arm.

8. The bracket of claim 1, wherein the arm extends generally parallel with respect to the longitudinal axis of the base.

9. The bracket of claim 1, wherein the arm extends generally laterally with respect to the longitudinal axis of the base.

10. The bracket of claim 1, wherein the base, the post, and the arm are integrally formed.

11. The bracket of claim 1, wherein the medical article includes a catheter system comprising a catheter hub and a catheter, and wherein the channel defined by the arm is dimensioned to receive the catheter.

12. The bracket of claim 1, wherein the arm and the post are spaced a longitudinal distance apart.

13. The bracket of claim 1, wherein the channel is a first channel, wherein the post is one of a plurality of posts, and wherein each of the plurality of posts is separated a lateral distance from an adjacent post to define a second channel therebetween, the second channel oriented generally parallel to the longitudinal axis and dimensioned to receive at least a portion of the medical article.

14. A medical article securement system comprising the bracket of claim 1, wherein the bracket is coupled to a base dressing having a first side and a second side opposite the first side, the second side comprising a skin-contact adhesive, wherein the base includes a second major surface opposite the first major surface, and wherein the second major surface of the base is coupled to the first side of the base dressing.

15. A method for coupling a medical article to a medical article securement system, the method comprising:
providing a medical article;
providing a medical article securement system comprising a bracket wherein the bracket comprises:
a base having a longitudinal axis and a first major surface,
a post extending upwardly from the base in a direction generally normal to the first major surface of the base, and
an arm extending generally parallel to the first major surface of the base, the arm spaced a distance from the first major surface of the base to define a channel under the arm, the channel dimensioned to receive at least a portion of the medical article, the arm including a fixed end and a free end such that the arm is cantilevered, wherein the arm defines a lateral width W that extends from the fixed end of the arm to the free end of the arm, and wherein the post is located within the lateral width W of the arm on the base;
abutting an external surface of the medical article against the post without passing the post through the medical article; and
moving a portion of the medical article into the channel defined by the arm by positioning the portion of the medical article adjacent the free end of the arm, and sliding the portion of the medical article under the arm, into the channel.

16. The method of claim 15, wherein moving a portion of the medical article into the channel defined by the arm occurs substantially simultaneously with abutting an external surface of the medical article against the post.

17. The method of claim 15, wherein the channel is a first channel, wherein the post is one of a plurality of posts spaced a lateral distance apart to define a second channel therebetween, and further comprising positioning a portion of the medical article in the second channel.

18. The method of claim 17, wherein positioning a portion of the medical article in the second channel occurs substantially simultaneously with abutting an external surface of the medical article against the post.

19. A bracket configured for use with a medical article having a proximal end, a distal end, and a longitudinal axis extending from the proximal end to the distal end, the bracket comprising:
   a base having a first major surface, a proximal end, a distal end, and a longitudinal axis extending from the proximal end to the distal end, wherein the longitudinal axis of the base is oriented generally parallel to the longitudinal axis of the medical article of the base when the medical article is coupled to the bracket;
   an arm coupled to the base and extending generally parallel to the first major surface of the base, the arm spaced a distance from the first major surface of the base to define a first channel under the arm, the first channel generally oriented generally parallel to the longitudinal axis of the base and dimensioned to receive at least a portion of the medical article, the arm including a fixed end and a free end such that the arm is cantilevered, the arm configured to inhibit movement of the medical article in at least a direction that is generally normal to the first major surface of the base when the medical article is coupled to the bracket; and
   a plurality of posts coupled to the base and extending upwardly from the base in a direction generally normal to the first major surface of the base, the plurality of posts together configured to abut an external surface on the medical article without being passed through the medical article to inhibit at least longitudinal movement of the medical article when the medical article is coupled to the bracket, each of the plurality of posts being separated a lateral distance from an adjacent post to define a second channel therebetween, the second channel oriented generally along the longitudinal axis and dimensioned to receive at least a portion of the medical article,
   wherein the arm defines a lateral width W that extends from the fixed end of the arm to the free end of the arm, and wherein the post is located within the lateral width W of the arm on the base.

* * * * *